(12) United States Patent
Bird et al.

(10) Patent No.: US 7,514,570 B2
(45) Date of Patent: Apr. 7, 2009

(54) DERIVATIVES OF 3-HYDROXY-4-(CYCLYL-ALKYLAMINOALKYL)-5-PHENYL-1H-PYRAZOLE AS ANTAGONISTS OF THE GONADOTROPIN RELEASING HORMONE (GNRH) FOR USE IN THE TREATMENT OF SEX HORMONE RELATED CONDITIONS, SUCH AS PROSTATIC OF UTERINE CANCER

(75) Inventors: Thomas Geoffrey Colerick Bird, Reims (FR); Mickael Louis Pierre Maudet, Reims (FR); Matthias Ferdinand Herdemann, Reims (FR)

(73) Assignee: AstraZeneca AB, Sodertalje (SE)

( * ) Notice: Subject to any disclaimer, the term of this patent is extended or adjusted under 35 U.S.C. 154(b) by 360 days.

(21) Appl. No.: 10/524,977

(22) PCT Filed: Aug. 19, 2003

(86) PCT No.: PCT/GB03/03633

§ 371 (c)(1),
(2), (4) Date: Nov. 28, 2005

(87) PCT Pub. No.: WO2004/017961

PCT Pub. Date: Mar. 4, 2004

(65) Prior Publication Data

US 2006/0287379 A1    Dec. 21, 2006

(30) Foreign Application Priority Data

Aug. 21, 2002   (EP)   ................... 02292077

(51) Int. Cl.
  *C07D 403/02* (2006.01)
  *C07D 231/10* (2006.01)
  *A61K 31/4155* (2006.01)
(52) U.S. Cl. ................. 548/364.7; 548/364.4; 514/406; 514/407
(58) Field of Classification Search ............... 548/364.4, 548/364.7; 514/406, 407
  See application file for complete search history.

(56) References Cited

FOREIGN PATENT DOCUMENTS

| EP | 1468990 A1 | 10/2004 |
|---|---|---|
| JP | 10/287655 | 10/1998 |
| JP | 10 287655 (A) | 10/1998 |
| WO | WO 97/21435 A1 | 6/1997 |
| WO | WO 97/21703 A1 | 6/1997 |
| WO | WO 97/21704 A1 | 6/1997 |
| WO | WO 97/21707 A1 | 6/1997 |
| WO | WO 98/55116 A1 | 12/1998 |
| WO | WO 98/55119 A1 | 12/1998 |
| WO | WO 98/55123 A1 | 12/1998 |
| WO | WO 98/55470 A1 | 12/1998 |
| WO | WO 98/55479 A1 | 12/1998 |
| WO | WO 99/21553 A1 | 5/1999 |
| WO | WO 99/21557 A1 | 5/1999 |
| WO | WO 99/41251 A1 | 8/1999 |
| WO | WO 99/41252 A1 | 8/1999 |
| WO | WO 99/51231 A1 | 10/1999 |
| WO | WO 99/51232 A1 | 10/1999 |
| WO | WO 99/51233 A1 | 10/1999 |
| WO | WO 99/51234 A1 | 10/1999 |
| WO | WO 99/51595 A1 | 10/1999 |
| WO | WO 99/51596 A1 | 10/1999 |
| WO | WO 00/04013 A1 | 1/2000 |
| WO | 00/31063 | 6/2000 |
| WO | 00/31072 | 6/2000 |
| WO | WO 00/31063 A1 | 6/2000 |
| WO | WO 00/31072 A1 | 6/2000 |
| WO | WO 00/53178 A1 | 8/2000 |
| WO | WO 00/53179 A1 | 8/2000 |
| WO | WO 00/53180 A1 | 8/2000 |
| WO | WO 00/53181 A1 | 8/2000 |
| WO | WO 00/53185 A1 | 8/2000 |
| WO | WO 00/53602 A1 | 8/2000 |
| WO | 00/53602 | 9/2000 |
| WO | WO 00/69433 A1 | 11/2000 |
| WO | 02/48112 | 6/2002 |
| WO | WO 02/48112 A2 | 6/2002 |
| WO | WO 02/66459 A1 | 8/2002 |
| WO | WO 02/92565 A2 | 11/2002 |
| WO | 03/053927 | 7/2003 |
| WO | WO 03/53927 A1 | 7/2003 |

OTHER PUBLICATIONS

Mandred E. Wolff, Burger's Medicinal Chemistry and Drug Discovery, Fifth Edition, vol. 1: Principles and Practice, 1994, John Wiley and Sons, Inc., pp. 975-977.*
Vippagunta et al., Crystalline solids, 2001, Advanced Drug Delivery Reviews, 48, pp. 1 and 18.*
Database CA 'Online! Chemical Abstracts Service, Columbus, Ohio, US;O'Callaghan, C. N. : "Synthesis of ethyl 3-oxo-4-pyrazolidinecarboxylates" retrieved from STN Database accession No. 77 :61875 XP002261638 abstract & Journal of the Chemical Society, Perkin Transactions 1 : Organic and 610-Organic Chemistry (1972-1999) (1972), (11), 1416-19.
Database CA 'Online! Chemical Abstracts Service, Columbus, Ohio, US ; Mohareb, Rafat M. et al : "The reaction of 2-amino-3-cyano-4,5,6,7-tetrahydrobenzo-bthiophene with diethyl malonate : synthesis of coumarin, pyridine, and thiazole derivatives" retrieved from STN Database accession No. 135 :92599 XP002261639 abstract & Heteroatom Chemistry (2001), 12(3), 168-175.

(Continued)

*Primary Examiner*—Kamal A Saeed
*Assistant Examiner*—Kristin Bianchi

(57) ABSTRACT

The invention relates to a group of novel pyrazole compounds of Formula (I): wherein: $R^1$, $R^2$, $R^3$, M and $R^5$ are as defined in the specification, which are useful as gonadotrophin releasing hormone antagonists. The invention also relates to pharmaceutical formulations of said compounds, methods of treatment using said compounds and to processes for the preparation of said compounds.

17 Claims, No Drawings

OTHER PUBLICATIONS

Database CA 'Online! Chemical Abstracts Service, Columbus, Ohio, US ; Afridi, A. Sultan et al : "N-Oxides and related compounds . Part 56 . Preparation of NN'-linked bi(heteroaryls) from dehydroacetic acid and 2,6-dimethyl-4-pyrone" retrieved from STN Database accession No. 87 :201414 XP002261640 abstract & Journal of the Chemical Society, Perkin Transactions 1 : Organic and Bio-Organic Chemistry (1972-1999) (1977), (12), 1428-36.

Database CA 'Online! Chemical Abstracts Service, Columbus, Ohio, US; Mustafa, Ahmed et al : "Reactions of substituted coumarins, furocoumarins, and khellinonestyryl derivatives with hydrazine and phenylhydrazine" retrieved from STN Database accession No. 65 :20701 XPOO2261641 abstract & Justus Liebigs Annalen Der Chemie (1966), 692, 166-73.

O'Callaghan, C, N 'Synthesis of ethyl 3-oxo-4-pyrazolidine carboxylates.' Journal of the Chemical Society, Perkin Transactions 1: Organic and Bioorganic Chemistry, 1972, vol. 11, pp. 1416-1419.

Mohareb et al 'The reaction of 2-amino-3-cyano-4,5,6,7-tetrahydrobenzo[b]-thiophene with diethyl malonate: synthesis of coumarin, pyridine, and thiazole derivatives.' Heteroatom Chemistry, 2001, vol. 12(13), pp. 168-175.

Afridi et al 'Preparation of NN'-linked bi(heteroaryls) from dehydroacetic acid and 2,6-dimethyl-4-pyrone.' Journal of the Chemical Society, Perkin Transactions 1: Organic and Bioorganic Chemistry, 1977, vol. 12, pp. 1428-1436.

Mustafa et al 'Reactions of substituted coumarins, furocoumarins, and khellinonestyryl derivatives with hydrazine and phenylhydrazine.' Justus Liebigs Annalen der Chemie, 1966, vol. 692, pp. 166-173.

Ashton et al 'Substituted Indole-5-carboxamides and -acetamides as Potent Nonpeptide GnRH Receptor Antagonist.' Bioorganic & Medicinal Chemistry Letters 2001, vol. 11, pp. 1723-1726.

Ashton et al 'Potent Nonpeptide GnHR Receptor Antagonists Derived from Substituted Indole-5-carboxamides and -acetamides Bearing a Pyridine Side-Chain Terminus.' Bioorganic & Medicinal Chemistry Letters 2001, vol. 11, pp. 1727-1731.

Ashton et al 'Orally Bioavailable, Indole-Based Nonpeptide GnHR Receptor Antagonists with High Potancy and Functional Activity.' Bioorganic and medicinal Chemistry Letters 2001, vol. 11, pp. 2597-2602.

Chu et al 'Initial Structure-Activity Relationship of a Novel Class of Nonpeptidyl GnHR Receptor Antagonists: 2-Arylindoles.' Bioorganic and Medicinal Chemistry Letters 2001, vol. 11, pp. 509-513.

Chu et al 'SAR Studies of novel 5-Substituted 2-Arylindoles as Nonpeptidyl GnHR Receptor Antagonists.' Bioorganic and Medicinal Chemistry Letters 2001, vol. 11, pp. 515-517.

Freidinger, R, M. 'Nonpeptide ligands for peptide and protein receptors.' Current Opinion in Chemical Biology 1999, vol. 3, pp. 395-406.

Goulet, M, T. 'Gonadotropin Releasing Hormone Antagonists.' Annual Reports in Medicinal Chemistry 1995, vol. 30, pp. 169-178.

Lin, et al '2-(3,5-Dimethylphenyl)tryptamine Derivatives That Bind to the GnHR Receptor.' Bioorganic & Medicinal Chemistry Letters 2001, vol. 11, pp. 1073-1076.

Lin, et al 'Heterocyclic Derivatives of 2-(3,5-Dimethylphenyl)typtamine as GnHR Receptor Antagonists.' Bioorganic & Medicinal Chemistry Letters 2001, vol. 11, pp. 1077-1080.

Simoene, J, P. 'Synthesis of chiral β-methyl tryptamine-derived GnHR antagonists.' Tetrahedron Letters 2001, vol. 42, pp. 6459-6461.

Walsh et al 'A convergent synthesis of (S)-β-methyl-2-aryltryptamine based gonadotropin releasing hormone antagonists.' Tetrahedron, 2001, vol. 57, pp. 5233-5241.

Young et al '2-Arylindoles as Gonadotropin Releasing Hormone (GnHR) Antagonists: Optimization of the Tryptamine Side Chain.' Bioorganic & Medicinal Chemistry Letters, 2002, vol. 12, pp. 827-832.

Ujjainwalla, F 'Total synthesis of 6- and 7-azaindole derived GnHR antagonists.' Tetrahedron Letters, 2001, vol. 42, pp. 6441-6445.

Simeone et al. 'Modification of the Pyridine Moiety of Non-peptidyl Indole GnHR Receptor Antagonists.' Bioorganic & Medicinal Chemistry Letters, 2002, vol. 12, pp. 3329-3332.

Gibbs, J, B 'Pharmaceutical Research in Molecular Oncology.' Cell, 1994, vol. 79, pp. 193-198.

European Patent Office, Communication Pursuant to Article 96(2) EPC, for co-pending EP Patent Application No. 03 792 487.5-2101, Oct. 5, 2005.

\* cited by examiner

DERIVATIVES OF 3-HYDROXY-4-(CYCLYL-ALKYLAMINOALKYL)-5-PHENYL-1H-PYRAZOLE AS ANTAGONISTS OF THE GONADOTROPIN RELEASING HORMONE (GNRH) FOR USE IN THE TREATMENT OF SEX HORMONE RELATED CONDITIONS, SUCH AS PROSTATIC OF UTERINE CANCER

CROSS-REFERENCE TO RELATED APPLICATIONS

This application is a US National Stage under 35 U.S.C 371 of International Application No. PCT/GB2003/003633, filed Aug. 19, 2003, which claims priority under 35 U.S.C. § 119(a)-(d) to European Patent Application No. 02292077.1 filed on Aug. 21, 2002, the specification of which is incorporated by reference herein.

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185, WO 00/53602, WO 02/066477, WO 02/066478, WO 02/06645 and WO 02/092565.

It would be desirable to provide further compounds, such compounds being GnRH antagonists. Thus, according to the first aspect of the invention there is provided a compound of Formula (I),

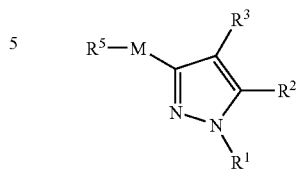

Formula (I)

wherein:

$R^1$ is selected from: hydrogen, optionally-substituted $C_{1-6}$alkyl, optionally substituted aryl or optionally-substituted aryl$C_{1-6}$alkyl;

$R^2$ is an optionally-substituted mono or bi-cyclic aromatic ring;

$R^3$ is selected from a group of Formula (IIa) to Formula (IIf):

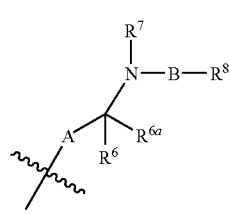

Formula (IIa)

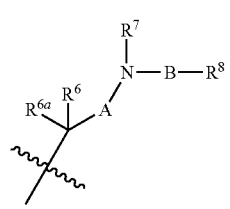

Formula (IIb)

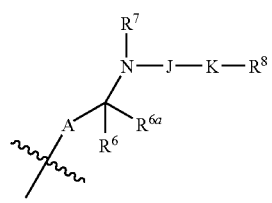

Formula (IIc)

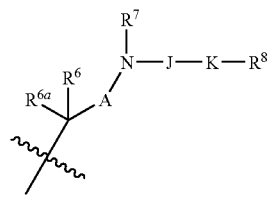

Formula (IId)

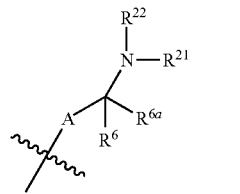

Formula (IIe)

-continued

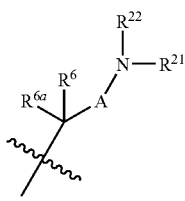

Formula (IIf)

$R^5$ is a group of Formula (III):

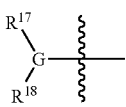

Formula (III)

$R^6$ and $R^{6a}$ are independently selected from hydrogen, fluoro, optionally substituted $C_{1-6}$alkyl, optionally-substituted aryl or optionally substituted aryl$C_{1-6}$alkyl, or $R^6$ and $R^{6a}$ taken together and the carbon atom to which they are attached form a carbocyclic ring of 3-7 atoms, or $R^6$ and $R^{6a}$ taken together and the carbon atom to which they are attached form a carbonyl group;

or when A is not a direct bond the group

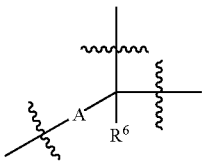

forms a carbocyclic ring of 3-7 carbon atoms or a heterocyclic ring containing one or more heteroatoms;

or the group

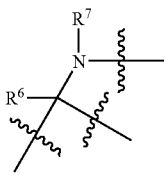

forms a heterocyclic ring containing 3-7 carbon atoms and one or more heteroatoms;

$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —C(NR$^9$R$^{10}$)=NH;

or when $R^3$ is a group of Formula (IIc) or (IId) $R^7$ is of the formula -J-K—R$^8$;

$R^8$ is selected from:
(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-6}$alkyl-S(O$_n$)—, —O—R$^b$, —NR$^b$R$^c$, —C(O)—R$^b$, —C(O)O—R$^b$, —CONR$^b$R$^c$, NH—C(O)—R$^b$ or —S(O$_n$)NR$^b$R$^c$,
where R$^b$ and R$^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;
(ii) nitro when B is a group of Formula (IV) and X is CH and p is 0;
(iii) $C_{3-7}$cycloalkyl, aryl or aryl$C_{1-6}$alkyl each of which is optionally substituted by R$^{12}$, R$^{13}$ and R$^{14}$;
(iv) -(Q)-aryl, -(Q)-heterocyclyl, -aryl-(Q)-aryl, each of which is optionally substituted by R$^{12}$, R$^{13}$ and R$^{14}$ wherein -(Q)- is selected from E, F or a direct bond;
(v) heterocyclyl or heterocyclyl$C_{1-6}$alkyl each of which is optionally substituted by up to 4 substituents independently selected from R$^{12}$, R$^{13}$ and R$^{14}$;
(vi) a group selected from R$^{12}$, R$^{13}$ and R$^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3-7 atoms, optionally substituted heterocyclyl, optionally substituted heterocyclyl$C_{1-6}$alkyl or $R^9$ and $R^{10}$ taken together can form an optionally substituted ring of 3-9 atoms or $R^9$ and $R^{10}$ taken together with the carbon atom to which they are attached form a carbonyl group;

$R^{11}$ is selected from: hydrogen, optionally substituted $C_{1-6}$alkyl, or N(R$^9$R$^{10}$);

$R^{12}$ is selected from: hydrogen, hydroxy, R$^{17}$R$^{18}$N(CH$_2$)$_{cc}$—, R$^{17}$R$^{18}$NC(O)(CH$_2$)$_{cc}$—, optionally substituted $C_{1-6}$alkyl-C(O)N(R$^9$)(CH$_2$)$_{cc}$—, optionally substituted $C_{1-6}$alkyl-SO$_2$N(R$^9$)—, optionally substituted aryl-SO$_2$N(R$^9$)—, $C_{1-3}$perfluoroalkyl-SO$_2$N(R$^9$)—; optionally substituted $C_{1-6}$alkyl-N(R$^9$)SO$_2$—, optionally substituted aryl-N(R$^9$)SO$_2$—, $C_{1-3}$perfluoroalkyl-N(R$^9$)SO$_2$—, optionally substituted $C_{1-6}$alkanoyl-N(R$^9$)SO$_2$—; optionally substituted aryl-C(O)N(R$^9$)SO$_2$—, optionally substituted $C_{1-6}$alkyl-S(O$_n$)—, optionally substituted aryl-S(O$_n$)—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, R$^9$O(CH$_2$)$_s$—, R$^9$(O)O(CH$_2$)$_s$—, R$^9$OC(O)(CH$_2$)$_s$—, R$^{16}$S(O$_n$)(CH$_2$)$_s$—, R$^9$R$^{10}$NC(O)(CH$_2$)$_s$— or halo;

$R^{15}$ is selected from: hydrogen, optionally substituted $C_{1-6}$alkyl, R$^{19}$OC(O)—, R$^9$R$^{10}$NC(O)—, R$^9$C(O)—, R$^9$S(O$_n$)—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula R$^{18a}$—C(R$^9$R$^{10}$)$_{0-1}$— wherein R$^{18a}$ is selected from: R$^{19}$OC(O)—, R$^9$R$^{10}$NC(O)—, R$^9$R$^{10}$N—, R$^9$C(O)—, R$^9$C(O)N(R$^{10}$)—, R$^9$R$^{10}$NC(O)—, R$^9$R$^{10}$NC(O)N(R$^{10}$)—, R$^9$SO$_2$N(R$^{10}$)—, R$^9$R$^{10}$NSO$_2$N(R$^{10}$)—, R$^9$C(O)O—, R$^9$OC(O)—, R$^9$R$^{10}$NC(O)O—, R$^9$O—, R$^9$S(O$_n$)—, R$^9$R$^{10}$NS(O$_n$)—, hydrogen, optionally substituted $C_{1-6}$alkyl, optionally substituted heterocyclyl;

or $R^{17}$ and $R^{18}$ when taken together form an optionally substituted carbocyclic ring of 3-7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{21}$ and $R^{22}$ are independently selected from hydrogen, optionally substituted $C_{1-6}$alkyl, optionally substituted $C_{3-7}$cycloalkyl, optionally substituted heterocyclyl, optionally substituted heterocyclyl$C_{1-6}$alkyl, optionally substituted $C_{3-6}$alkenyl, optionally substituted $C_{3-6}$alkynyl, —$(C_{1-5}$alkyl$)_{aa}$-S$(O_n)$—$(C_{1-5}$alkyl$)_{bb}$-; $R^9R^{10}$NC$_{2-6}$alkyl, $R^9$OC$_{2-6}$alkyl or $R^9R^{10}$NC(O)C$_{2-6}$alkyl, with the proviso that $R^9$ and $R^{10}$ independently or taken together are not optionally substituted aryl or optionally substituted aryl$C_{1-6}$alkyl; or $R^{21}$ and $R^{22}$ taken together form an optionally substituted non-aromatic heterocyclic ring;

A is selected from:
(i) a direct bond;
(ii) optionally-substituted $C_{1-5}$alkylene wherein the optional substituents are independently selected from: optionally-substituted $C_{1-6}$-alkyl optionally-substituted aryl or optionally substituted aryl$C_{1-6}$alkyl;
(iii) a carbocyclic ring of 3-7 atoms;
(iv) a carbonyl group or —C(O)—C($R^dR^d$)—, wherein $R^d$ is independently selected from hydrogen and $C_{1-2}$alkyl;

or when $R^3$ is a group of Formula (IIa) or (IIb), the group

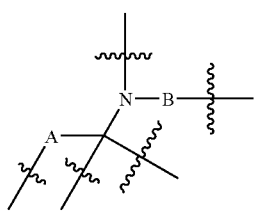

forms a heterocyclic ring containing 3-7 carbon atoms and one or more heteroatoms;

or when $R^3$ is a group of Formula (IIa), (IIb), (IIc) or (IId), the group

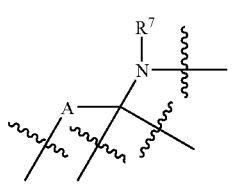

forms a heterocyclic ring containing 3-7 carbon atoms and one or more heteroatoms;

B is selected from:
(i) a direct bond;
(ii) a group of Formula (IV)

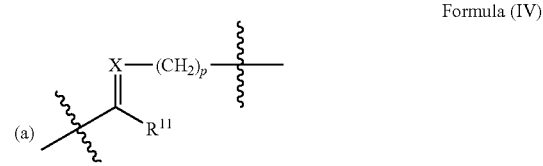

Formula (IV)

wherein:
X is selected from N or CH, wherein at position (a) Formula (IV) is attached to the nitrogen atom and the $(CH_2)_p$ group is attached to $R^8$; and
(iii) a group independently selected from: optionally substituted $C_{1-6}$alkylene, optionally substitute $C_{3-7}$cycloalkyl, optionally substituted $C_{3-6}$alkenylene, optionally substituted $C_{3-6}$alkynyl, $C_{1-6}$alkoxy, $(C_{1-5}$alkyl$)_{aa}$-S$(O_n)$—$(C_{1-5}$alkyl$)_{bb}$-, —$(C_{1-5}$alkyl$)_{aa}$-O—$(C_{1-5}$alkyl$)_{bb}$-, —$(C_{1-5}$alkyl$)_{aa}$-C(O)—$(C_{1-5}$alkyl$)_{bb}$- or $(C_{1-5}$alkyl$)_{aa}$-N$(R^{15})$—$(C_{1-5}$alkyl$)_{bb}$,
wherein $R^{15}$ and the $(C_{1-5}$alkyl$)_{aa}$ or $(C_{1-5}$alkyl$)_{bb}$ chain can be joined to form a ring, wherein the combined length of $(C_{1-5}$alkyl$)_{aa}$ and $(C_{1-5}$alkyl$)_{bb}$ is less than or equal to $C_5$alkyl;

or the group —B—$R^8$ represents a group of Formula (V)

Formula (V)

or the group

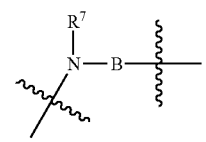

together forms an optionally substituted heterocyclic ring containing 4-7 carbons atoms;
or the group

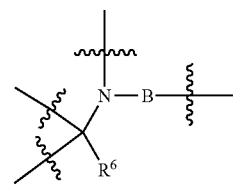

forms a heterocyclic ring containing 3-7 carbon atoms and one or more heteroatoms;

E is —O—, —S$(O_n)$, —C(O)—, —NR$^{15}$— or —C$(R^9R^{10})_q$;

F is -E$(CH_2)_r$—;

G is selected from: hydrogen, halo, N, O, S$(O_n)$, C(O), C$(R^9R^{10})_t$, optionally substituted $C_{2-6}$alkenylene, optionally substituted $C_{2-6}$alkynylene or a direct bond to $R^{18}$, J is a group of the formula: —(CH$_2$)$_s$-L-(CH$_2$)$_s$— wherein when s is greater than 0, the alkylene group is optionally substituted,
or the group

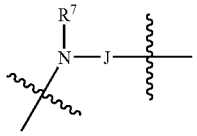

together forms an optionally substituted heterocyclic ring containing 4-7 carbons atoms;

K is selected from: a direct bond, —(CH$_2$)$_{s1}$—, —(CH$_2$)$_{s1}$—O—(CH$_2$)$_{s2}$—, —(CH$_2$)$_{s1}$—C(O)—(CH$_2$)$_{s2}$—, —(CH$_2$)$_{s1}$—S(O$_n$)—(CH$_2$)$_{s2}$—, —(CH$_2$)$_{s1}$—N(R$^{18}$)—(CH$_2$)$_{s2}$—, —(CH$_2$)$_{s1}$—C(O)N(R$^9$)—(CH$_2$)$_{s2}$—, —(CH$_2$)$_{s1}$—N(R$^9$)C(O)—(CH$_2$)$_{s2}$—, —(CH$_2$)$_{s1}$—N(R$^9$)C(O)N(R$^9$)—(CH$_2$)$_{s2}$—, —(CH$_2$)$_{s1}$—OC(O)—(CH$_2$)$_{s2}$—, —(CH$_2$)$_{s1}$—C(O)O—(CH$_2$)$_{s2}$—, —(CH$_2$)$_{s1}$—N(R$^9$)C(O)O—(CH$_2$)$_{s2}$—, —(CH$_2$)$_{s1}$—OC(O)N(R$^9$)—(CH$_2$)$_{s2}$—, —(CH$_2$)$_{s1}$—OS(O$_n$)—(CH$_2$)$_{s2}$—, or —(CH$_2$)$_{s1}$—S(O$_n$)—O—(CH$_2$)$_{s2}$—, —(CH$_2$)$_{s1}$—S(O)$_2$N(R$^9$)—(CH$_2$)$_{s2}$— or —(CH$_2$)$_{s1}$—N(R$^9$)S(O)$_2$—(CH$_2$)$_{s2}$—; wherein the —(CH$_2$)$_{s1}$— and —(CH$_2$)$_{s2}$— groups are independently optionally substituted by hydroxy or C$_{1-4}$alkyl;

L is selected from optionally substituted aryl or optionally substituted heterocyclyl;

M is selected from —(CH$_2$)$_{0-2}$—O— or C(O)NH—;

n is an integer from 0 to 2;
p is an integer from 0 to 4;
q is an integer from 0 to 4;
r is an integer from 0 to 4;
s is an integer from 0 to 4;
s1 and s2 are independently selected from an integer from 0 to 4, and s1+s2 is less than or equal to 4;
t is an integer between 0 and 4; and
aa and bb are independently 0 or 1;
cc is an integer between 0 to 2;

with the proviso that
(i) when G is hydrogen or halo, then R$^{17}$ and R$^{18}$ are both absent;
(ii) when G is O, S(O$_n$), C(O) or C(R$^{11}$R$^{12}$)$_t$ then G is substituted by a single group independently selected from the definition of R$^{17}$ or R$^{18}$ and when G is a direct bond to R$^{18}$ then G is substituted by a single group selected from R$^{18}$;
(iii) when R$^3$ is a group of Formula (IIb), B is a group of Formula (IV), R$^8$ is selected from group (i) or (ii) above, R$^{11}$ is a group of the formula N(R$^{10}$R$^{11}$) and R$^1$, R$^2$ and R$^5$ are as defined above then R$^4$ cannot be hydrogen;
(iv) R$^3$ cannot be unsubstituted pyridyl or unsubstituted pyrimidinyl; and
(v) when R$^3$ is pyrazolyl substituted by phenyl or pyrazolyl substituted by phenyl and acetyl, R$^5$-M is hydroxyl or acetyloxy, R$^2$ is unsubstituted phenyl, then R$^1$ cannot be hydrogen or acetyl;

or a salt, solvate or pro-drug thereof.

According to the further feature of the first aspect of the invention there is provided a compound of Formula (I) with the proviso that
(i) when G is hydrogen or halo, then R$^{17}$ and R$^{18}$ are both absent;
(ii) when G is O, S(O$_n$), C(O) or C(R$^{11}$R$^{12}$)$_t$ then G is substituted by a single group independently selected from the definition of R$^{17}$ or R$^{18}$ and when G is a direct bond to R$^{18}$ then G is substituted by a single group selected from R$^{18}$;
(iii) when R$^3$ is a group of Formula (IIb), B is a group of Formula (IV), R$^8$ is selected from group (i) or (ii) above, R$^{11}$ is a group of the formula N(R$^{10}$R$^{11}$) and R$^1$, R$^2$ and R$^5$ are as defined above then R$^4$ cannot be hydrogen; and
(iv) R$^3$ cannot be an unsubstituted or substituted aromatic heterocyclic ring, wherein the aromatic heterocyclic ring is attached directed to the pyrazole in Formula (I);
or a salt, solvate or pro-drug thereof.

According to the further feature of the first aspect of the invention there is provided a compound of Formula (Ia),

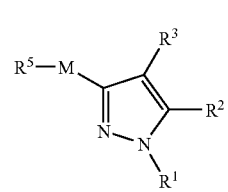

Formula (Ia)

wherein:

R$^1$ is selected from: hydrogen, optionally-substituted C$_{1-6}$alkyl, optionally substituted aryl or optionally-substituted arylC$_{1-6}$alkyl;

R$^2$ is an optionally-substituted mono or bi-cyclic aromatic ring;

R$^3$ is selected from a group of Formula (IIa) to Formula (IIf):

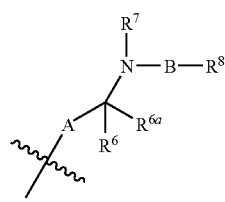

Formula (IIa)

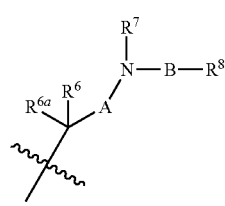

Formula (IIb)

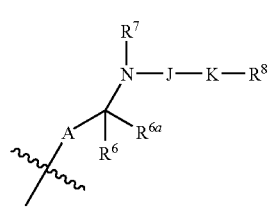

Formula (IIc)

-continued

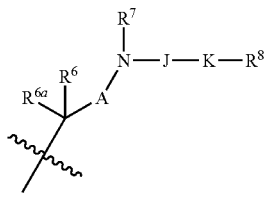

Formual (IId)

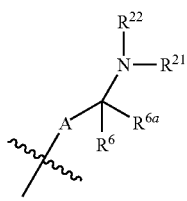

Formula (IIe)

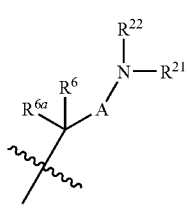

Formula (IIf)

$R^5$ is a group of Formula (III):

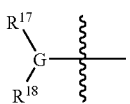

Formula (III)

$R^6$ and $R^{6a}$ are independently selected from hydrogen, optionally substituted $C_{1-6}$alkyl, optionally-substituted aryl or optionally substituted aryl$C_{1-6}$alkyl, or $R^6$ and $R^{6a}$ taken together and the carbon atom to which they are attached form a carbocyclic ring of 3-7 atoms, or $R^6$ and $R^{6a}$ taken together and the carbon atom to which they are attached form a carbonyl group;

or when A is not a direct bond the group

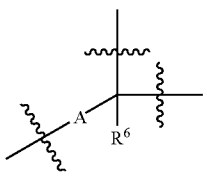

forms a carbocyclic ring of 3-7 carbon atoms or a heterocyclic ring containing one or more heteroatoms;

or the group

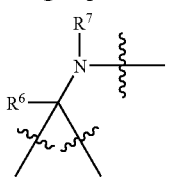

forms a heterocyclic ring containing 3-7 carbon atoms and one or more heteroatoms;

$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —C(NR$^9$R$^{10}$)=NH;

or when $R^3$ is a group of Formula (IIc) or (IId) $R^7$ is of the formula -J-K—$R^8$;

$R^8$ is selected from:
(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-6}$alkyl-S(O$_n$)—, —O—$R^b$, —NR$^b$R$^c$, —C(O)—$R^b$, —C(O)O—$R^b$, —CONR$^b$R$^c$ or NH—C(O)—$R^b$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N(C$_{1-4}$alkyl)-;
(ii) nitro when B is a group of Formula (IV) and X is CH and p is 0;
(iii) $C_{3-7}$cycloalkyl, aryl or aryl$C_{1-6}$-alkyl each of which is optionally substituted by $R^{12}$, $R^{13}$ and $R^{14}$;
(iv) -(Q)-aryl, -(Q)-heterocyclyl, -aryl-(Q)-aryl, each of which is optionally substituted by $R^{12}$, $R^{13}$ and $R^{14}$ wherein -(Q)- is selected from E, F or a direct bond;
(v) heterocyclyl or heterocyclyl$C_{1-6}$alkyl each of which is optionally substituted by $R^{12}$, $R^{13}$ and $R^{14}$;
(vi) a group selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3-7 atoms, optionally substituted heterocyclyl, optionally substituted heterocyclyl$C_{1-6}$alkyl or $R^9$ and $R^{10}$ taken together can form an optionally substituted ring of 3-9 atoms or $R^9$ and $R^{10}$ taken together with the carbon atom to which they are attached form a carbonyl group;

$R^{11}$ is selected from: hydrogen, optionally substituted $C_{1-6}$alkyl, or N(R$^9$R$^{10}$);

$R^{12}$ is selected from: hydrogen, hydroxy, $R^{17}R^{18}N$—, optionally substituted $C_{1-6}$alkyl-SO$_2$N(R$^9$)—, optionally substituted aryl-SO$_2$N(R$^9$)—, $C_{1-3}$perfluoroalkyl-SO$_2$N(R$^9$)—; optionally substituted $C_{1-6}$alkyl-N(R$^9$)SO$_2$—, optionally substituted aryl-N(R$^9$)SO$_2$—, $C_{1-3}$perfluoroalkyl-N(R$^9$)SO$_2$— optionally substituted $C_{1-6}$alkanoyl-N(R$^9$)SO$_2$—; optionally substituted aryl-C(O)N(R$^9$)SO$_2$, optionally substituted $C_{1-6}$alkyl-S(O$_n$)—, optionally substituted aryl-S(O$_n$)—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, optionally substituted $C_{1-6}$alkyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo;

$R^{15}$ is selected from: hydrogen, optionally substituted $C_{1-6}$alkyl, $R^{19}OC(O)$—, $R^9R^{10}NC(O)$—, $R^9C(O)$—, $R^9S(O_n)$—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula $R^{18a}$—C(R$^9$R$^{10}$)$_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, optionally substituted $C_{1-6}$alkyl, optionally substituted heterocyclyl;

or $R^{17}$ and $R^{18}$ when taken together form an optionally substituted carbocyclic ring of 3-7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{20}$ is selected from $R^{12}$ or $R^{13}$;

$R^{21}$ and $R^{22}$ are independently selected from hydrogen, optionally substituted $C_{1-6}$alkyl, optionally substituted $C_{3-7}$cycloalkyl, optionally substituted heterocyclyl, optionally substituted heterocyclyl$C_{1-6}$alkyl, optionally substituted $C_{3-6}$alkenyl, optionally substituted $C_{3-6}$alkynyl, —$(C_{1-5}$alkyl$)_{aa}$-S$(O_n)$—$(C_{1-5}$alkyl$)_{bb}$-; $R^9R^{10}NC_{2-6}$alkyl, $R^9OC_{2-6}$alkyl or $R^9R^{10}NC(O)C_{2-6}$alkyl, with the proviso that $R^9$ and $R^{10}$ independently or taken together are not optionally substituted aryl or optionally substituted aryl$C_{1-6}$alkyl; or $R^{21}$ and $R^{22}$ taken together form an optionally substituted non-aromatic heterocyclic ring;

A is selected from:
  (i) a direct bond;
  (ii) optionally-substituted $C_{1-5}$alkylene wherein the optional substituents are independently selected from: optionally-substituted $C_{1-6}$alkyl optionally-substituted aryl, optionally substituted aryl$C_{1-6}$alkyl or substituted
  (iii) a carbocyclic ring of 3-7 atoms;
  (iv) a carbonyl group;

or when $R^3$ is a group of Formula (IIa) or (IIb), the group

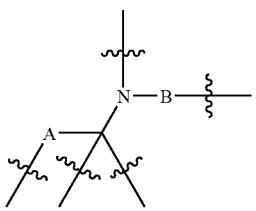

forms a heterocyclic ring containing 3-7 carbon atoms and one or more heteroatoms;

or when $R^3$ is a group of Formula (IIa), (IIb), (IIc) or (IId), the group

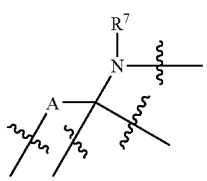

forms a heterocyclic ring containing 3-7 carbon atoms and one or more heteroatoms;

B is selected from:
  (i) a direct bond;
  (ii) a group of Formula (IV)

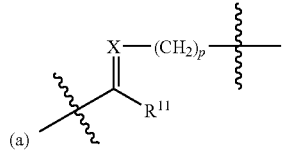

Formula (IV)

wherein:
X is selected from N or CH, wherein at position (a) Formula (IV) is attached to the nitrogen atom and the $(CH_2)p$ group is attached to $R^8$; and (iii) a group independently selected from: optionally substituted $C_{1-6}$alkylene, optionally substitute $C_{3-7}$cycloalkyl, optionally substituted $C_{3-6}$alkenylene, optionally substituted $C_{3-6}$alkyl, $C_{1-6}$alkoxy, $(C_{1-5}$alkyl$)_{aa}$-S$(O_n)$—$(C_{1-5}$alkyl$)_{bb}$-, $(C_{1-5}$alkyl$)_{aa}$-O—$(C_{1-5}$alkyl$)_{bb}$- or $(C_{1-5}$alkyl$)_{aa}$-N$(R^{15})$—$(C_{1-5}$alkyl$)_{bb}$, wherein $R^{15}$ and the $(C_{1-5}$alkyl$)_{aa}$ or $(C_{1-5}$alkyl$)_{bb}$ chain can be joined to form a ring;

or the group —B—$R^8$ represents a group of Formula (V)

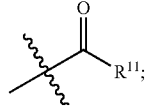

Formula (V)

or the group

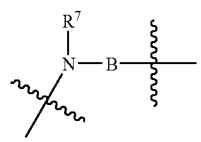

together forms a heterocyclic ring containing 5-7 carbons atoms;

or the group

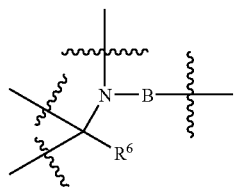

forms a heterocyclic ring containing 3-7 carbon atoms and one or more heteroatoms;

E is —O—, —S$(O_n)$, —C(O)—, —NR$^{15}$— or —C$(R^9R^{10})_q$;

F is -E(CH$_2)_r$—;

G is selected from: hydrogen, halo, N, O, S$(O_n)$, C(O), C$(R^9R^{10})_p$, optionally substituted $C_{2-6}$alkenylene, optionally substituted $C_{2-6}$alkynylene or a direct bond to $R^{18}$, J is a group of the formula: —$(CH_2)_s$-L-$(CH_2)_s$— wherein when s is greater than 0, the alkylene group is optionally substituted K is selected from: a direct bond, —O—(CH$_2$)$_s$—, —C(O)—(CH$_2$)$_s$—, —S(O$_n$)—(CH$_2$)$_s$—, —N(R$^{18}$)—(CH$_2$)$_s$—, —OC(O)—(CH$_2$)$_s$—, —C(O)O—(CH$_2$)$_s$—, —OS(O$_n$)—(CH$_2$)$_s$—, or —S(O$_n$)—O—(CH$_2$)$_s$—;

L is selected from optionally substituted aryl or optionally substituted heterocyclyl;

M is —(CH$_2$)$_{0-2}$—O—;

n is an integer between 0 and 2;
p is an integer between 0 and 4;
q is an integer between 0 and 4;
r is an integer between 0 and 4;
s is an integer between 0 and 4; and
t is an integer between 0 and 4;
with the proviso that
(i) when G is hydrogen or halo, then R$^{17}$ and R$^{18}$ are both absent;
(ii) when G is O, S(O$_n$), C(O) or C(R$^{11}$R$^{12}$)$_r$ then G is substituted by a single group independently selected from the definition of R$^{17}$ or R$^{18}$ and when G is a direct bond to R$^{18}$ then G is substituted by a single group selected from R$^{18}$; and or a salt, solvate or pro-drug thereof.

According to a further feature of the first aspect of the invention there is provided a pharmaceutical formulation comprising a compound of Formula (I) or Formula (Ia), or salt, pro-drug or solvate thereof, and a pharmaceutically acceptable diluent or carrier.

According to a further feature of the first aspect of the invention there is provided the following uses of a compound of Formula (I) or Formula (Ia), or salt, pro-drug or solvate thereof:

(a) the use in the manufacture of a medicament for antagonising gonadotropin releasing hormone activity;
(b) the use in the manufacture of a medicament for administration to a patient, for reducing the secretion of luteinizing hormone by the pituitary gland of the patient; and
(c) the use in the manufacture of a medicament for administration to a patient, for therapeutically treating and/or preventing a sex hormone related condition in the patient, preferably a sex hormone related condition selected from prostate cancer and pre-menopausal breast cancer.

According to a further aspect of the invention there is provided a method of antagonising gonadotropin releasing hormone activity in a patient, comprising administering a compound of Formula (I) or Formula (Ia), or salt, pro-drug or solvate thereof, to a patient.

Whilst pharmaceutically-acceptable salts of compounds of the invention are preferred, other non-pharmaceutically-acceptable salts of compounds of the invention may also be useful, for example in the preparation of pharmaceutically-acceptable salts of compounds of the invention.

Whilst the invention comprises compounds of the invention, and salts, pro-drugs or solvates thereof, in a further embodiment of the invention, the invention comprises compounds of the invention and salts thereof.

In the present specification, unless otherwise indicated, an alkyl, alkylene, alkenyl or alkynyl moiety may be linear or branched. The term "alkylene" refers to the group —CH$_2$—. Thus, C$_8$ alkylene for example is —(CH)$_8$—. For avoidance of doubt the term C$_0$alkyl within the group C$_{0-5}$alkyl is a direct bond.

The term 'propylene' refers to trimethylene and the branched alkyl chains —CH(CH$_3$)CH$_2$— and —CH$_2$—CH(CH$_3$)—. The straight chain propylene di-radical is preferred, i.e. —CH$_2$CH$_2$CH$_2$—. Specific propylene radicals refer to the particular structure, thus the term, propyl-2-ene refers to the group —CH$_2$—CH(CH$_3$)—. Similar notation is used for other divalent alkyl chains such as butylene.

The term '2-propenyl' refers to the group —CH$_2$—CH=CH—.

The term "aryl" refers to phenyl or naphthyl.

The term "carbamoyl" refers to the group —C(O)NH$_2$.

The term "halo" refers to fluoro, chloro, bromo or iodo.

The term "heterocyclyl" or "heterocyclic ring" refers to a 4-12 membered, preferably 5-10 membered aromatic mono or bicyclic ring or a 4-12 membered, preferably 5-10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl, benzodioxyl and dihydropyrimidinyl. This definition further comprises sulphur-containing rings wherein the sulphur atom has been oxidised to an S(O) or S(O2) group.

The term "aromatic ring" refers to a 5-10 membered aromatic mono or bicyclic ring optionally containing up to 5 heteroatoms independently selected from nitrogen, oxygen or sulphur. Examples of such "aromatic rings" include: phenyl, pyrrolyl, pyrazolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include phenyl, thienyl and pyridyl.

The symbol

denotes where the respective group is linked to the remainder of the molecule.

For the avoidance of doubt where two groups or integers appear within the same definition, for example, —(CH$_2$)$_s$-L-(CH$_2$)$_s$— or R$^9$R$^{10}$NSO$_2$N(R$^{10}$)—, then these can be the same of different.

For the avoidance of doubt, where several groups together form a ring, for example: 'the group

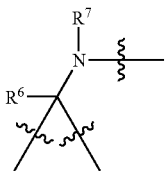

forms a heterocyclic ring containing 3-7 carbon atoms and one or more heteroatoms', then the groups shown cyclises to form a ring, i.e

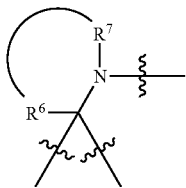

the component of which are defined by the definitions of the groups which form the ring, thus in the above example the ring would include a nitrogen atom. For example in Example 5 this group forms a piperazine ring.

The term $C_{1-3}$perfluoroalkyl refers to a $C_{1-3}$alkyl chain in which all hydrogens have been replaced with a fluorine atom. Examples of $C_{1-3}$perfluoroalkyl include trifluoromethyl, pentafluoroethyl and 1-trifluoromethyl-1,2,2,2-tetrafluoroethyl-. Preferably $C_{1-3}$perfluoroalkyl is trifluromethyl.

Examples of $C_{1-8}$alkyl include: methyl, ethyl, propyl, iso-propyl, butyl, iso-butyl, tert-butyl and 2-methyl-pentyl; example of $C_{1-8}$alkylene include: methylene, ethylene and 2-methyl-propylene; examples of $C_{1-6}$alkenyl include allyl (2-propenyl) and 2-butenyl, examples of $C_{1-6}$alkynyl 2-propynyl and 3-butynyl, examples of halo$C_{1-6}$alkyl include fluoroethyl, chloropropyl and bromobutyl, examples of hydroxy$C_{1-6}$alkyl include hydroxymethyl, hydroxyethyl and hydroxybutyl, examples of $C_{1-8}$alkoxy include methoxy, ethoxy and butyloxy; examples of $C_{1-4}$alkoxy$C_{1-4}$alkyl include methoxyethyl, propoxybutyl and propoxymethyl, examples of $C_{1-6}$alkanoyl incude formyl, ethanoyl, propanoyl or pentanoyl, examples of N—$C_{1-4}$alkylamino include N-methylamino and N-ethylamino; examples of N,N-di-$C_{1-4}$alkylamino include N,N-dimethylaminoethyl, N,N-di-methylaminopropyl and N,N-dipropylaminoethyl, examples of HO—$C_{2-4}$alkyl-NH include hydroxymethylamino hydroxyethylamino and hydroxypropyamino, examples of HO—$C_{2-4}$alkyl-N($C_{1-4}$alkyl) include N-methyl-hydroxymethylamino, N-ethyl-hydroxyethylamino, and N-propyl-hydroxypropyamino, examples of $C_{1-6}$alkyl-S($O_n$)-methylthio, methylsulphinyl, ethylsulphinyl, ethylsulphonyl and propylsulphonyl, include examples of aryl$C_{1-6}$alkyl include benzyl, phenethyl and phenylbutyl, examples of heterocyclyl$C_{1-6}$alkyl include pyrrolidin-1-yl ethyl, imidazolylethyl, pyridylmethyl and pyrimidinylethyl.

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

Preferred compounds of Formula (I), Formula (Ia) and Formula (Ib) are those wherein any one of the following apply.

Preferably $R^1$ is selected from hydrogen or optionally substituted $C_{1-6}$alkyl. More preferably $R^1$ represents hydrogen or unsubstituted $C_{1-6}$alkyl. Yet more preferably $R^1$ represents hydrogen, methyl, ethyl or tert-butyl. Most preferably $R^1$ represents hydrogen.

Preferably optional substituents on $R^1$ are independently selected from: optionally substituted $C_{1-4}$alkyl, optionally substituted $C_{2-6}$alkenyl, cyano, nitro, $C_{1-3}$perfluoroalkyl, $C_{1-3}$perfluoroalkoxy, optionally substituted aryl, optionally substituted aryl$C_{1-6}$alkyl, $R^9O(CH_2)_v$—; $R^9C(O)O(CH_2)_v$—, $R^9OC(O)(CH_2)_v$—, $R^{16}S(O_n)(CH_2)_v$—, $R^9R^{10}NC(O)(CH_2)_v$—, or halo wherein v is an integer between 0 and 4, and where 2 optional substituents are present together they can optionally form a $C_{3-7}$carbocyclic ring or a heterocyclic ring.

Preferably $R^2$ is an optionally substituted monocyclic aromatic ring structure. Most preferably $R^2$ represents optionally substituted phenyl.

Preferably optional substituents on $R^2$ are independently selected from: optionally substituted $C_{1-6}$-alkyl, optionally substituted $C_{2-6}$alkenyl, cyano, nitro, $C_{1-3}$perfluoroalkyl, $C_{1-3}$perfluoroalkoxy, optionally substituted aryl, optionally substituted aryl$C_{1-6}$-alkyl, $R^9O(CH_2)_p$—, $R^9C(O)O(CH_2)_w$—, $R^9OC(O)(CH_2)_w$—, $R^{16}S(O_n)(CH_2)_w$—, $R^9R^{10}NC(O)(CH_2)_w$—, $R^9R^{10}N$— or halo; wherein w is an integer between 0 and 4 and $R^9$ and $R^{10}$ are as defined above. Further preferably the optional substituents on $R^2$ are independently selected from cyano, $R^eR^fN$—, optionally substituted $C_{1-6}$alkyl (preferably, $C_{1-4}$alkyl, eg, methyl or ethyl), optionally substituted $C_{1-6}$alkoxy (preferably, $C_{1-4}$alkoxy, eg, methoxy, ethoxy or tert-butoxy) or halo (eg, F, Br or Cl) wherein $R^e$ and $R^f$ are independently selected from hydrogen, $C_{1-6}$alkyl or aryl. Yet further preferably optional substituents on $R^2$ are independently selected from methyl, ethyl, methoxy, ethoxy, tert-butoxy, F or Cl. Most preferably optional substituents on $R^2$ are independently selected from methyl, F or Cl. Preferably $R^2$ bears 1, 2 or 3 substituents.

Most preferably $R^2$ represents

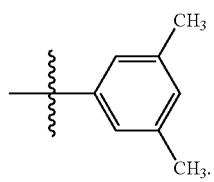

Preferably $R^3$ is selected from a group of Formula (IIa) Formula (IIb), Formula (IIc) or Formula (IId). Further preferably $R^3$ is selected from Formula (IIa) or Formula (IIb). Most preferably $R^3$ is a group of Formula (IIb).

Preferably the group of Formula (III):

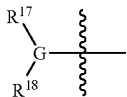

Formula (III)

is selected from a group of Formula III-a; III-b; III-c; III-d; III-e; III-f, III-g, III-h, III-i, or III-j, III-k or III-l;

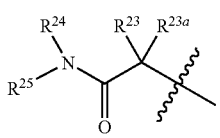

III-a

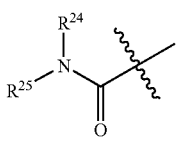

III-b

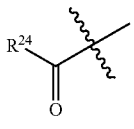

III-c

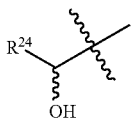

III-d

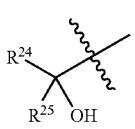

III-e

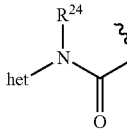

III-f

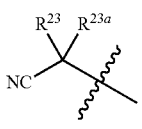

III-g

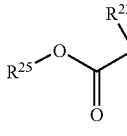

III-h

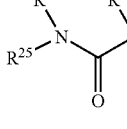

III-i

-continued

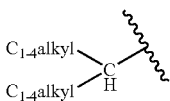

III-j

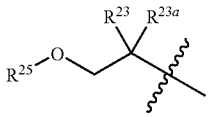

III-k

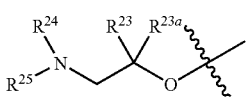

III-l wherein:
het represents an optionally substituted 3- to 8-membered heterocyclic ring containing from 1 to 4 heteroatoms independently selected from O, N and S;
$R^{23}$ and $R^{23a}$ are independently selected from:
(i) hydrogen or optionally substituted $C_{1-8}$alkyl; or
(ii) $R^{23}$ and $R^{23a}$ together with the carbon to which they are attached form an optionally substituted 3 to 7-membered cycloalkyl ring;
$R^{24}$ and $R^{25}$ are selected from:
(i) $R^{24}$ selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{25}$ is selected from hydrogen; optionally substituted $C_{1-8}$alkyl and optionally substituted aryl;
(ii) wherein the group of Formula (III) represents a group of Formula III-a, III-b or III-i, then the group $NR^{24}(—R^{25})$ represents an optionally substituted 3- to 8-membered heterocyclic ring optionally containing from 1 to 3 further heteroatoms independently selected from O, N and S; or
(iii) wherein the group of Formula (III) represents structure III-e,

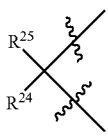

represents an optionally substituted 3- to 8-membered heterocyclic ring optionally containing from 1 to 4 heteroatoms independently selected from O, N and S;
More preferably the group of Formula (III) is selected from a group of Formula III-a, III-g, III-h, III-i, III-j, III-k or III-l:

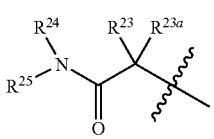

III-a

-continued

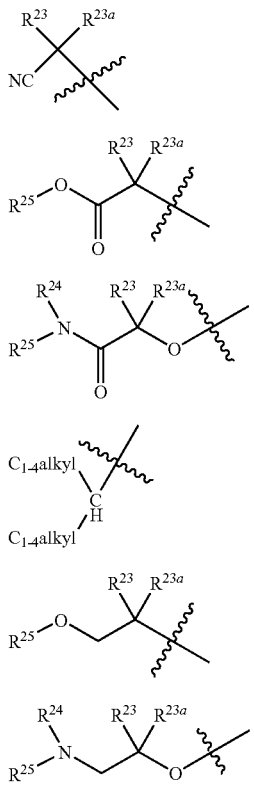

wherein R$^{23}$, R$^{23a}$, R$^{24}$ and R$^{25}$ are as defined above.

Further preferably the group of Formula (III) is selected from one of the following groups:

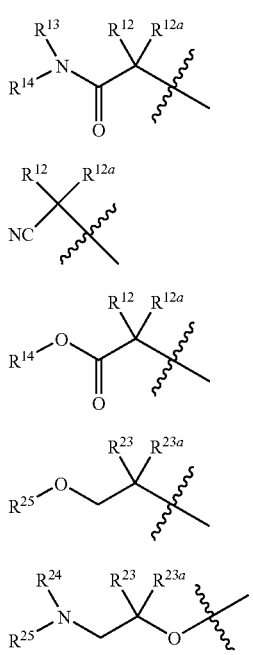

wherein R$^{23}$, R$^{23a}$, R$^{24}$ and R$^{25}$ are as defined above.

Yet further preferably the group of Formula (III) is selected from one of the following groups:

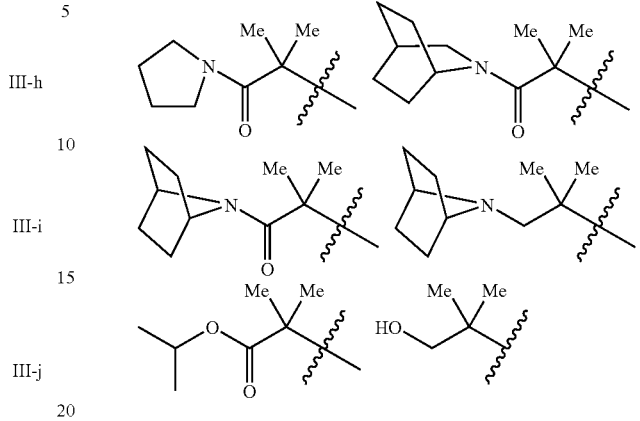

wherein Me represents methyl.

Yet further preferably the group of Formula (III) is selected from one of the following groups:

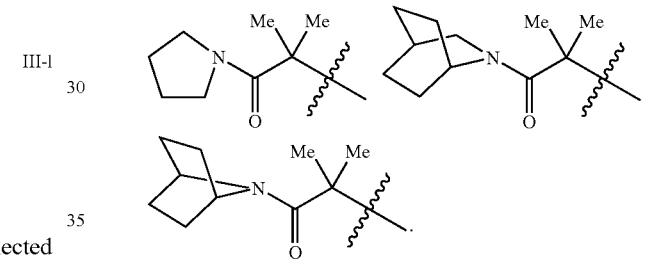

Most preferably the group of Formula (III) is:

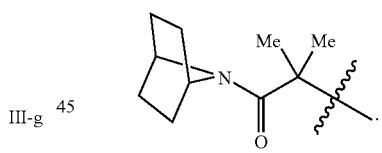

Preferably R$^6$ and R$^{6a}$ are independently selected from hydrogen, fluoro, optionally substituted C$_{1-6}$alkyl or R$^6$ and R$^{6a}$ taken together and the carbon atom to which they are attached form a carbocyclic ring of 3-7 atoms More preferably R$^6$ and R$^{6a}$ are independently selected from hydrogen, unsubstituted C$_{1-6}$alkyl or R$^6$ and R$^{6a}$ taken together and the carbon atom to which they are attached form a carbocyclic ring of 3-7 atoms. Yet more preferably R$^6$ and R$^{6a}$ are independently selected from hydrogen, methyl or R$^6$ and R$^{6a}$ taken together and the carbon atom to which they are attached form cyclopropyl. Most preferably R$^6$ is hydrogen and R$^{6a}$ is methyl.

Preferably R$^7$ is selected from: hydrogen or C$_{1-4}$alkyl. More preferably R$^7$ is hydrogen or methyl. Most preferably R$^7$ is hydrogen.

When R$^8$ is heterocyclyl then R$^8$ is preferably selected from one of the following groups:

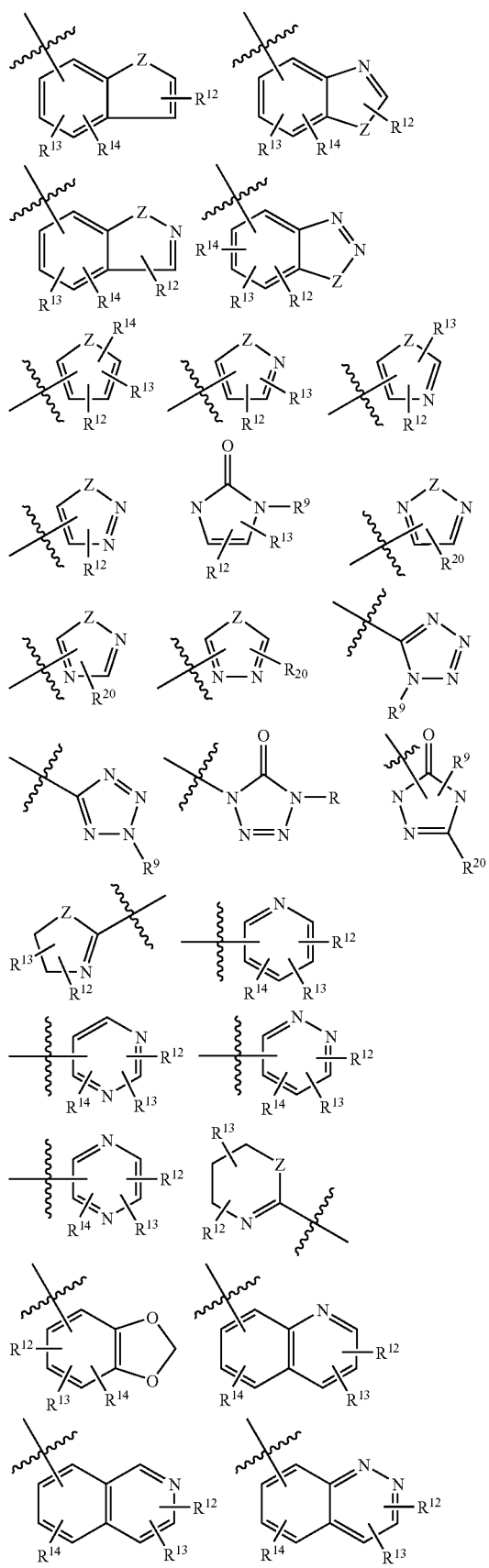
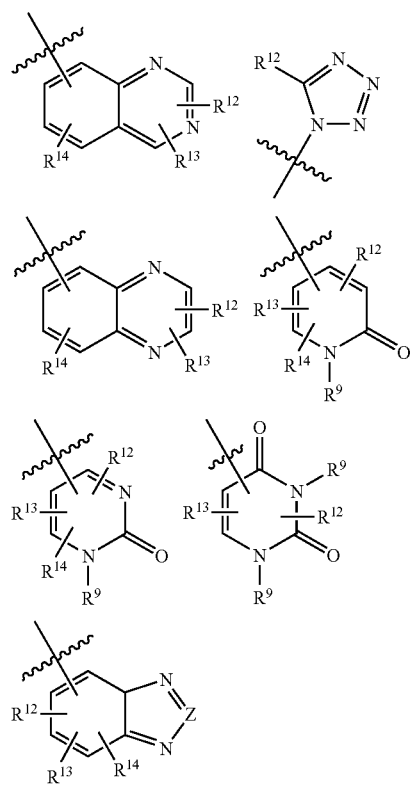
wherein Z is selected from: O, S or N(R$^9$), R$^{20}$ is selected form any group within the definitions of R$^{12}$ and R$^{13}$, and R$^9$, R$^{12}$, R$^{13}$ and R$^{14}$ are as defined above.
In a further embodiment of the invention when R$^8$ is heterocyclyl then R$^8$ is preferably selected from one of the following groups:
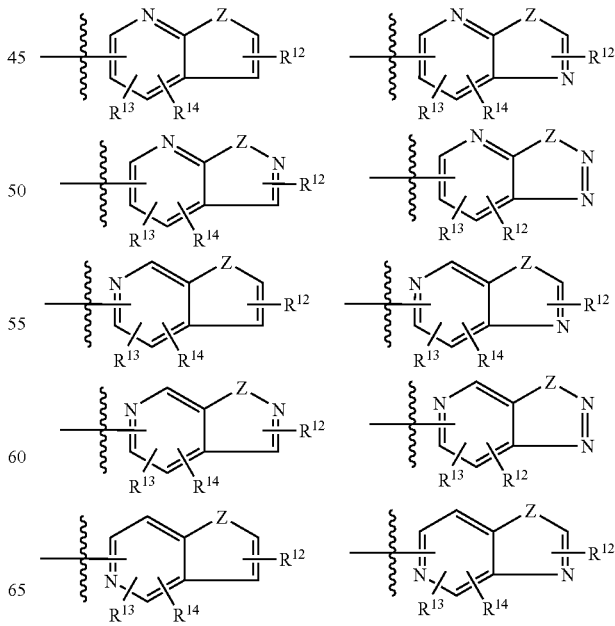

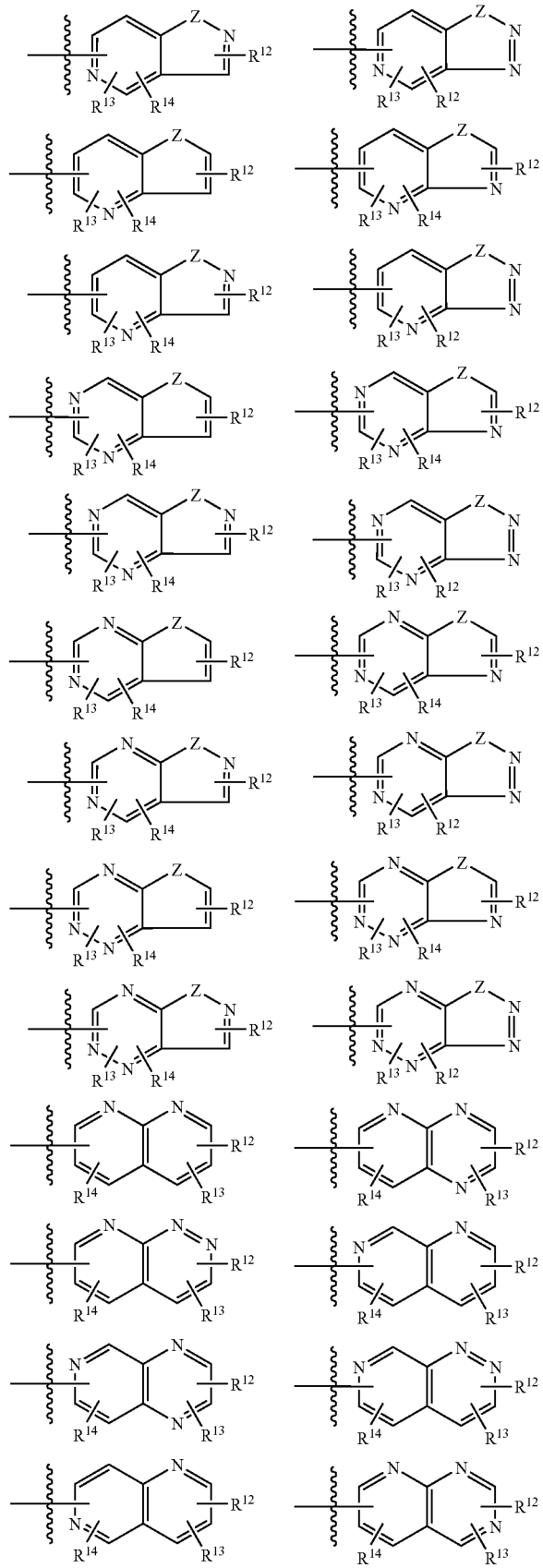
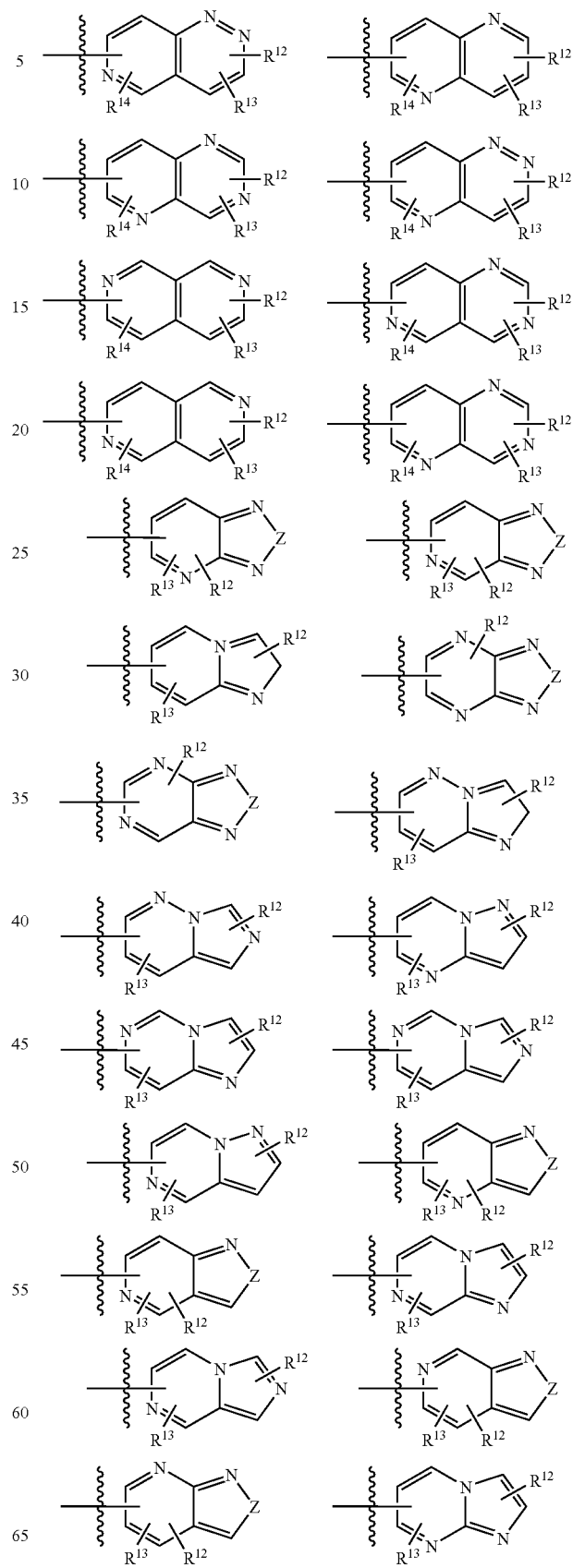

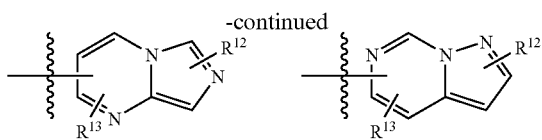

wherein Z is selected from: O, S or N(R$^9$) and R$^9$, R$^{12}$ and R$^{13}$ are as defined above.

When R$^8$ is aryl or aryl-(C)-aryl optionally substituted by R$^{12}$, R$^{13}$ and R$^{14}$, R$^8$ is preferably selected one of the following groups:

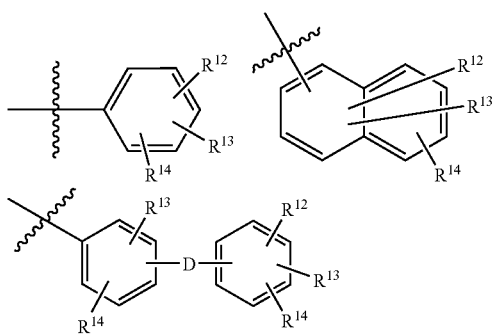

wherein D is selected from group E, group F or a direct bond;
Preferably R$^8$ is selected from
(i) hydrogen, C$_{1-6}$alkyl, C$_{2-6}$alkenyl, haloC$_{1-6}$alkyl, hydroxy, cyano, C$_{1-6}$alkylS(O$_n$)—, —O—R$^b$, C$_{1-4}$alkoxyC$_{1-4}$alkyl, —C(O)—R$^b$, C(O)O—R$^b$, —NH—C(O)—R$^b$, N,N-di-C$_{1-4}$alkylamino, S(O$_n$)NR$^b$R$^c$ where R$^b$ and R$^c$ are independently selected from hydrogen and C$_{1-6}$alkyl, and n is 0, 1 or 2;
(ii) -(Q)-aryl, optionally substituted by up to 3 groups selected from R$^{12}$, R$^{13}$ and R$^{14}$;
(iii) C$_{4-7}$heterocyclyl, optionally substituted by up to 3 groups selected from R$^{12}$, R$^{13}$ and R$^{14}$, more preferably selected from: azirinyl, azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetraydrotriazinyl, dihydrotriazinyl, tetrahydrofuranyl, dioxolanyl, tetrahydropyranyl, dioxanyl, trioxanyl, tetrahydrotienyl, 1-oxotetrahydrothienyl, 1,1-dioxotetrahydrothienyl tetrahydrothiopyran, 1-oxotetrahydrothiopyran, 1,1-dioxotetrahydrothiopyran, dithianyl, trithianyl, morpholinyl, oxathiolanyl, oxathianyl, thiomorpholinyl, thiazinanyl, 1-oxo-thiomorpholinyl, 1,1-dioxothiomorpholinyl, thiazolidinyl, pyrrolyl, imidazolyl, triazolyl, pyridyl, pyrimidinyl, pyrazinyl, pyridazinyl, triazinyl, thiazolyl, thiadiazolyl, thiadiazinyl, oxazolyl, isoxazolyl, oxadiazolyl, furazanyl, octahydropyrrolopyrrolyl, octahydropyrrolopyrrolyl, benzotriazolyl, dihydrobenzotriazolyl, indolyl, indolinyl, benzimidazolyl, 2,3-dihydrobenzimidazoly, benzotriazolyl 2,3-dihydro benzotriazolyl quinolinyl, isoquinolinyl, cinnolinyl, phthalazinyl, quinazolinyl, quinozalinyl, naphthyridinyl, pteridinyl, benzodioxolyl, tetrahydrodioxolopyrrolyl, 1,5-dioxa-9-azaspiro[5.5]undecanyl or 8-oxa-3-azabicyclooctanyl; each of which is optionally substituted by up to 3 groups selected from R$^{12}$, R$^{13}$ and R$^{14}$ or
(iv) C$_{3-7}$carbocyclyl; optionally substituted by up to 3 groups selected from R$^{12}$, R$^{13}$ and R$^{14}$;

Further preferably R$^8$ is selected from
(i) hydrogen, C$_{1-6}$alkyl, C$_{2-6}$alkenyl, haloC$_{1-6}$alkyl, hydroxy, cyano, C$_{1-6}$alkylS(O$_n$)—, —O—R$^b$, C$_{1-4}$alkoxyC$_{1-4}$alkyl, —C(O)—R$^b$, C(O)O—R$^b$, —NH—C(O)—R$^b$, N,N-di-C$_{1-4}$alkylamino, —S(O$_n$)NR$^b$R$^c$ where R$^b$ and R$^c$ are independently selected from hydrogen and C$_{1-6}$alkyl, and n is 0, 1 or 2;
preferably selected from: hydrogen, methyl, isopropyl, t-butyl, 1-methylethyl, allyl, fluoroethyl, hydroxy, cyano, ethylsulphonyl, methoxy, 1-methyl-2-methoxyethyl, acetyl, t-butoxycarbonyl, acetylamino, dimethylamino, diethylamino, (1-methylethyl) amino, isopropylamino or aminosulphonyl;
(ii) -(Q)-aryl, wherein aryl is optionally substituted by up to 3 groups selected from R$^{12}$, R$^{13}$ and R$^{14}$;
(iii) azetidinyl, furanyl, tetrahydrofuranyl, tetrahydropyranyl, pyrrolidinyl, piperidinyl, piperazinyl, hexahydropyrimidinyl, morpholinyl, tetrahydrothienyl, 1,1-dioxotetrahydrothienyl, thiomorpholinyl, 1-oxo-thiomorpholinyl, 1,1-dioxo-thiomorpholinyl, imidazolyl, triazolyl, thienyl, thiazolyl, isoxazolyl, pyridyl, pyrimidinyl, pyrazinyl, tetrahydro-3aH-[1,3]dioxolo[4,5-c]pyrrolyl, 1,5-dioxa-9-azaspiro[5.5]undecanyl, 8-oxa-3-azabicyclo[3.2.1]octanyl, benzodioxolyl, 2,3-dihydrobenzotriazolyl, 1,2-dihydroquinolinyl or octahydropyrrolo[3,4-c]pyrrolyl; each of which is optionally substituted by up to 3 groups selected from R$^{12}$, R$^{13}$ and R$^{14}$; or
(iv) C$_{3-7}$carbocyclyl, optionally substituted by up to 3 groups selected from R$^{12}$, R$^{13}$ and R$^{14}$;

Yet further preferably R$^8$ is selected from
(i) phenyl optionally substituted by up to 3 groups selected from R$^{12}$, R$^{13}$ and R$^{14}$ or naphthyl;
(ii) furanyl, tetrahydropyranyl, pyrrolidinyl, piperazinyl, morpholinyl, 1,1-dioxo-thiomorpholinyl, thienyl, triazolyl, pyridyl, pyrimidinyl, pyrazinyl, tetrahydro-3aH-[1,3]dioxolo[4,5-c]pyrrolyl, benzodioxolyl, 1,2-dihydroquinolinyl or 2,3-dihydrobenzotriazolyl; each of which is optionally substituted by up to 3 groups selected from R$^{12}$, R$^{13}$ and R$^{14}$; or
(iii) C$_{3-7}$carbocyclyl (preferably cyclohexyl or cylopentyl, more preferably cyclohexyl) optionally substituted by up to 3 groups selected from R$^{12}$, R$^{13}$ and R$^{14}$;

Further preferably R$^8$ is selected from: phenyl, thienyl, pyridyl and benzodioxlyl optionally substituted by up to 3 groups selected from R$^{12}$, R$^{13}$ and R$^{14}$.

Most preferably R$^8$ is 1,3 benzodioxolyl.

In another embodiment of the invention R$^8$ is selected from piperidinyl or piperazinyl, azetidinyl, imidazolyl and thiazolyl, each of which is optionally substituted by up to 3 groups selected from R$^{12}$, R$^{13}$ and R$^{14}$.

In a further embodiment of the invention preferably R$^8$ is selected from hydrogen, cyano, C$_{1-4}$alkyl (more preferably methyl), C$_{2-6}$alkynyl (more prefeably 2-propynyl), hydroxyC$_{1-6}$alkyl (more preferably hydroxyethyl), C$_{1-4}$alkoxyC$_{1-4}$alkyl (more preferably methoxyethyl), haloC$_{1-6}$alkyl (more preferably fluoroethyl), C$_{1-4}$alkanoyl (more preferably formyl), C$_{1-4}$alkoxycarbonyl (more preferably butyloxycarbonyl), N,N-di-C$_{1-4}$alkylamino (more preferably N,N-dimethylaminoethyl and N,N-dimethylaminopropyl), C$_{1-6}$alkyl-S(O$_n$)— (more preferably ethylsulphonyl), cyclopentyl, phenyl, benzyl, cyanophenyl, pyrrolidinyl, pyrrolidinylethyl, imidazolyl, imidazolyC$_{1-6}$alkyl (more preferably imidazolylethyl), thiazolyl, pyridyl, pyridylC$_{1-6}$alkyl (more preferably pyridylmethyl) or pyrimidyl wherein a phenyl or heterocyclyl ring is optionally substituted by C$_{1-4}$alkyl or halo.

When R$^9$ and/or R$^{10}$ is a component of group G, R$^9$ and R$^{10}$ are preferably independently selected from hydrogen, optionally substituted C$_{1-6}$alkyl, optionally substituted aryl, optionally substituted arylC$_{1-6}$alkyl or R$^9$ and R$^{10}$ forms C$_{3-7}$cycloalkyl or heterocyclyl. Further preferably hydrogen or C$_{1-4}$alkyl. Most preferably hydrogen or methyl. Most preferably both R$^9$ and R$^{10}$ are methyl.

When R$^9$ and/or R$^{10}$ is a component of group R$^{18}$, R$^9$ and R$^{10}$ are preferably independently selected from hydrogen, optionally substituted C$_{1-6}$alkyl, optionally substituted aryl, optionally substituted arylC$_{1-6}$alkyl or R$^9$ and R$^{10}$ forms C$_{3-7}$cycloalkyl or heterocyclyl. Further preferably when R$^9$ is a component of group R$^{18}$, R$^9$ is preferably heterocyclyl. Most preferably pyrrolidinyl, 7-azabicyclo[2.2.1]hept-7-yl or. 3-azabicyclo[3.2.2]nonyl.

Preferably R$^{17}$ is hydrogen, hydroxy, cyano or is absent. Most preferably R$^{17}$ is absent.

Preferably R$^{18}$ is selected from hydrogen, R$^9$N(R$^{10}$)C(O)—, R$^9$C(O)—, R$^9$OC(O) or R$^{18a}$—C(R$^9$R$^{10}$)— wherein R$^{18a}$ is R$^9$N(R$^{10}$)C(O)—. Further preferably R$^9$C(O)—. Most preferably R$^9$C(O)— wherein R$^9$ is heterocyclyl.

Preferably A is selected from a direct bond, optionally substituted C$_{1-5}$alkylene, carbonyl or —C(O)—C(R$^d$R$^d$)—, wherein R$^d$ is independently selected from a direct bond hydrogen and C$_{1-2}$alkyl. Further preferably A is selected from C$_{1-5}$alkylene optionally substituted with C$_{1-4}$alkyl, carbonyl or carbonylmethyl. Yet further preferably A is a direct bond methylene. Most preferably methylene.

Preferably B is selected from optionally substituted C$_{1-6}$alkylene, optionally substituted C$_{3-6}$alkenylene, —(C$_{1-5}$alkyl)$_{aa}$-O—(C$_{1-5}$alkyl)$_{bb}$-, —(C$_{1-5}$alkyl)$_{aa}$-C(O)—(C$_{1-5}$alkyl)$_{bb}$-, —(CH$_2$)$_{s1}$—C(O)N(R$^9$)—(CH$_2$)$_{s2}$—, or the group

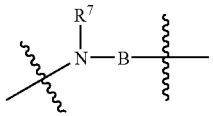

forms an optionally substituted C$_{4-7}$ heterocyclic ring, wherein aa and bb are independently 0 to 1 and, wherein the combined length of (C$_{1-5}$alkyl)$_{aa}$ and (C$_{1-5}$alkyl)$_{bb}$ is less than or equal to C$_5$alkyl.

More preferably B is C$_{1-6}$alkylene, C$_{3-6}$alkenylene, —(C$_{1-5}$alkyl)$_{aa}$-O—(C$_{1-5}$alkyl)$_{bb}$-, —(C$_{1-5}$alkyl)$_{aa}$-C(O)—(C$_{1-5}$alkyl)$_{bb}$-, —(CH$_2$)$_{s1}$—C(O)N(R$^9$)—, or the group

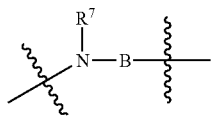

forms an optionally substituted saturated C$_{4-7}$ heterocyclic ring, wherein aa and bb are independently 0 or 1 and wherein the combined length of (C$_{1-5}$alkyl)$_{aa}$, (C$_{1-5}$alkyl)$_{bb}$ is less than or equal to C$_5$alkyl and wherein C$_{1-6}$alkylene is optionally substituted by hydroxy.

Further preferably B is unsubstituted C$_{1-6}$alkylene, C$_{3-6}$alkenylene —(C$_{1-5}$alkyl)$_{aa}$-O—(C$_{1-5}$alkyl)$_{bb}$-, —(C$_{1-5}$alkyl)$_{aa}$-C(O)— or the group

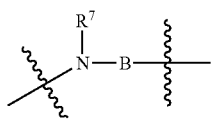

forms an optionally substituted saturated C$_{4-7}$ heterocyclic ring selected from: azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetraydrotriazinyl, dihydrotriazinyl, morpholinyl, thiomorpholinyl, thiazinanyl, thiazolidinyl, 1,5-dioxa-9-azaspiro[5.5]undecanyl or octahydropyrrolopyrrolyl, wherein the optional substituents are selected from. cyano, hydroxy, oxo, C$_{1-4}$alkyl, C$_{1-4}$alkoxy, C$_{1-4}$alkanoyl, R$^9$OC(O)(CH$_2$)$_w$—, R$^9$R$^{10}$NC(O)(CH$_2$)$_w$— or halo, wherein w is an integer between 0 and 4 and R$^9$ and R$^{10}$ are as defined above. Further preferably the optional substituents are selected from: cyano, hydroxy, oxo, C$_{1-4}$alkyl, C$_{1-4}$alkoxy and C$_{1-4}$alkanoyl, aa and bb are independently 0 or 1, wherein the combined length of (C$_{1-5}$alkyl)$_{aa}$ and (C$_{1-5}$alkyl)$_{bb}$ is less than or equal to C$_5$alkyl and wherein C$_{1-6}$alkylene is optionally substituted by hydroxy.

Yet further preferably B is selected from: methylene, ethylene, propylene, propyl-2-ene, butylene, pentylene, 2-propenyl, propoxy, ethoxyethyl, methylcarbonyl or methylcarbonylamino.

or the group

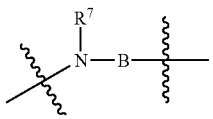

forms an C$_{4-7}$ heterocyclic ring selected from: pyrrolidinyl, piperidinyl, or piperazinyl, wherein the optional substituents are selected from oxo.

Most preferably B is selected from ethylene or butylene.

In another embodiment of the invention preferably B is selected from optionally substituted C$_{1-6}$alkylene or the group

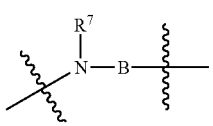

forms a C$_{5-7}$ heterocyclic ring. Preferably unsubstituted C$_{-6}$alkylene or a C$_{5-7}$ heterocyclic saturated ring. Most preferably methylene, ethylene, propylene, butylene or piperazinyl.

Peferably G is a direct bond, —O— or —C(R$^9$R$^{10}$)—. More preferably —C(R$^9$R$^{10}$)—. Most preferably —C(CH$_3$)$_2$—.

Preferably M is —CH$_2$—O—.

When R$^3$ is selected from a group of Formula (IIc) or Formula (IId) then the group

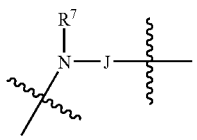

preferably forms an optionally substituted heterocyclic ring containing 4-7 carbons atoms.

More preferably the group

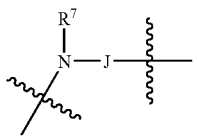

forms an optionally substituted saturated $C_{4-7}$ heteocyclic ring.

Further preferably the group

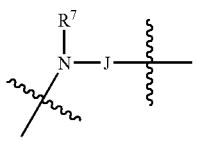

forms an optionally substituted saturated $C_{4-7}$ heteocyclic ring selected from: azetidinyl, pyrrolidinyl, pyrazolinyl, pyrazolidinyl, imidazolinyl, imidazolidinyl, piperidinyl, piperazinyl, hexahydropyrimidinyl, hexahydropyridazinyl, hexahydrotriazinyl, tetraydrotriazinyl, dihydrotriazinyl, morpholinyl, thiomorpholinyl, thiazinanyl, thiazolidinyl or octahydropyrrolopyrrolyl, wherein the optional substituents are selected from oxo.

Further preferably the group

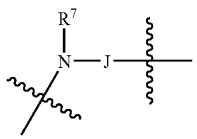

forms an optionally substituted saturated $C_{4-7}$ heteocyclic ring selected from: pyrrolidinyl, piperidinyl or piperazinyl, wherein the optional substituents are selected from oxo.

Most preferably the group

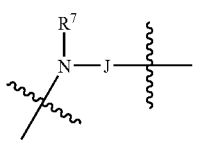

forms an optionally substituted saturated $C_{4-7}$ heteocyclic ring selected from: piperazinyl.

Preferably K is selected from: $-(CH_2)_s-$, $-(CH_2)_s-O-(CH_2)_s-$, $-(CH_2)_s-C(O)-(CH_2)_s-$, $-(CH_2)_s-N(R^{18})-(CH_2)_s-$, $-(CH_2)_s-C(O)N(R^{18})-(CH_2)-$, $-(CH_2)_s-N(R^{18})C(O)-(CH_2)_s-$, $-(CH_2)_s-S(O)_2N(R^{18})-(CH_2)_s-$, or $-(CH_2)_s-NHS(O)_2-(CH_2)_s-$, wherein s is independently selected from 0, 1, 2, 3 or 4, $R^{18}$ is selected from hydrogen or $C_{1-4}$alkyl (preferably hydrogen) and the $-(CH_2)_s-$ group is optionally substituted by hydroxy or $C_{1-4}$alkyl.

More preferably K is selected from: $-(CH_2)_s-$, $-(CH_2)$, $-O-(CH_2)_s-$, $-(CH_2)_s-C(O)-$, $-C(O)(CH_2)_s-$, $-(CH_2)_s-N(R^8)-$, $-(CH_2)_s-C(O)N(R^{18})-$, $-(CH_2)_s-N(R^{18})C(O)-(CH_2)_s-$, $-(CH_2)_s-S(O)_2N(R^{18})-$ or $-(CH_2)_s-NHS(O)_2-$, wherein s is independently selected from 0, 1, 2, 3 or 4, $R^{18}$ is selected from hydrogen or $C_{1-4}$alkyl (preferably hydrogen or methyl) and the $-(CH_2)_s-$ group is optionally substituted by hydroxy or $C_{1-4}$alkyl.

More preferably K is selected from: methylene, ethylene, propylene, butylene, oxy, 2-hydroxypropylene, carbonyl, methylcarbonyl, ethylcarbonyl, (methyl)methylcarbonyl, (ethyl)methylcarbonyl, carbonylmethylene, carbonylethylene, ethoxyethylene, amino, 2-hydroxypropylamino, carbonylamino, methylcarbonylamino, N-methyl-methylcarbonylamino, aminocarbonyl, methylaminocarbonyl, methylaminocarbonylmethyl, propylsulphonylamino or methylaminosulphonyl.

Further preferably K is selected from: methylene, ethylene, propylene, butylene carbonyl, methylcarbonyl or N-methyl-methylcarbonylamino.

Most preferably K is selected from: methylcarbonyl and N-methylmehtylcarbonylamino.

Preferably optional substituents on heterocyclyl groups in $R^8$, $R^9$, $R^{10}$, $R^{18}$ and $R^{19}$ or on heterocyclyl groups formed when $R^{17}$ and $R^{18}$ together form a heterocyclic ring are selected from: optionally substituted $C_{1-6}$alkyl, $C_{1-6}$alkoxy, $C_{1-6}$alkanoyl, optionally substituted $C_{2-6}$alkenyl, cyano, nitro, $C_{1-3}$perfluoroalkyl, $C_{1-3}$perfluoroalkoxy, optionally substituted aryl, optionally substituted aryl$C_{1-6}$alkyl, $R^9O(CH_2)_p-$, $R^9C(O)O(CH_2)_w-$, $R^9OC(O)(CH_2)_w-$, $R^{16}S(O_n)(CH_2)_w-$, $R^9R^{10}NC(O)(CH_2)_w-$ or halo; wherein w is an integer between 0 and 4 and p, $R^9$, $R^{10}$ and $R^{16}$ are as defined above.

More preferably optional substituents on $R^8$ are selected from: cyano, hydroxy, oxo, nitro, halo, trifluromethyl, $C_{1-4}$alkyl, $C_{1-4}$alkoxy, $C_{1-4}$alkanoyl, $R^9OC(O)(CH_2)_w-$, $R^9R^{10}N(CH_2)_w-$, $R^9R^{10}NC(O)(CH_2)_w-$, $R^9R^{10}NC(O)(CH_2)_w-$, $R^9R^{10}NC(O)N(R^9)(CH_2)_w-$, $R^9OC(O)N(R^9)(CH_2)_w-$, or halo, wherein w is an integer between 0 and 4 and $R^9$ and $R^{10}$ are selected from: hydrogen, $C_{1-4}$alkyl, $C_{1-4}$alkylsulphonyl and $C_{3-7}$carbocyclyl.

Further preferably optional substituents on $R^8$ are selected from: cyano, hydroxy, oxo, amino, N,N-di$C_{1-4}$alkyamino, N,N-di$C_{1-4}$alkyaminoC$_{1-4}$alkyl, N'—$C_{1-4}$alkylureido, N—$C_{1-4}$alkylsulphonylamino, N,N-di-$C_{1-4}$alkylsulphonylamino, nitro, halo, trifluoromethyl, $C_{1-4}$alkyl, $C_{1-4}$alkoxy, $C_{1-4}$alkanoyl, C1-4alkoxycarbonylamino and $C_{3-7}$carbocyclylcarbonylamino.

More preferably optional substituents on $R^8$ are selected from: cyano, oxo, methyl, t-butyl, methoxy, acetyl, amino, N,N-diethylamino, N'-isopropylureido, N'-cyclohexylureido, N-methylsulphonylamino, N,N-dimethylsulphonylamino, nitro, chloro, fluoro, trifluoromethyl, isopropoxycarbonylamino and cyclopentylcarbonylamino.

Most preferably optional substituents on $R^8$ are selected from: methoxy, fluoro, methylsulphonylamino and isopropoxycarbonylamino.

In a further embodiment of the invention optional substituents on $R^8$ are selected from: $C_{1-4}$alkoxy, fluoro, $C_{1-4}$alkylsulphonylamino, $C_{1-4}$alkanoylamino, $C_{1-4}$alkylureido and $C_{1-4}$alkoxycarbonylamino.

In a further embodiment of the invention when $R^8$ is phenyl then $R^8$ is preferably substituted and when $R^8$ is a heterocyclic ring $R^8$ is preferably unsubstituted.

Preferably the optional substituents on alkyl, alkenyl, alkyl, cycloalkyl and aryl groups are independently selected from $C_{1-6}$alkyl, $C_{1-6}$alkoxy, $C_{3-7}$cycloalkyl, optionally substituted aryl, optionally substituted aryl$C_{1-6}$alkyl, hydroxy, oxo, cyano, $C_{1-6}$alkoxy, halo (preferably fluoro), $R^{16}S(O_n)$ $(CH_2)_w$—, $R^9OC(O)$—, optionally substituted aryl$C_{1-3}$ alkoxy wherein $R^9$ is as defined above.

Preferably the optional substituents on optionally substituted aryl and aryl$C_{1-6}$alkyl groups are selected from: optionally substituted $C_{1-6}$alkyl, optionally substituted $C_{2-6}$alkenyl, cyano, nitro, halo (preferably fluoro), $C_{1-3}$perfluoroalkyl, $C_{1-3}$perfluoroalkoxy, optionally substituted aryl, optionally substituted aryl$C_{1-6}$alkyl, $R^9O(CH_2)_p$—, $R^9C(O)O$ $(CH_2)_w$—, $R^9OC(O)(CH_2)_w$—, $R^{16}S(O_n)(CH_2)_w$—, $R^9R^{10}NC(O)(CH_2)_w$— or halo; wherein w is an integer between 0 and 4 and n, $R^9$ and $R^{10}$ are as defined above.

In preferences for heterocyclyl in $R^8$ the nitrogen atoms contained in $R^8$ heteroaromatic rings exist either as drawn or, where chemically allowed, in their oxidised (N→O, N—OH) state.

Where optional substitution is mentioned at various places the optional substituents also comprise the following definition which refers to one, two, three or more optional substituents. Unless otherwise indicated above (i.e., where a list of optional substituents is specifically listed within a definition), each substituent can be independently selected from $C_{1-8}$alkyl (eg, $C_{2-6}$alkyl, and most preferably methyl, ethyl or tert-butyl); $C_{3-8}$cycloalkoxy, preferably cyclopropoxy, cyclobutoxy or cyclopentoxy; $C_{1-6}$alkoxy, preferably methoxy or $C_{2-4}$alkoxy; halo, preferably Cl or F; $Hal_3C$—, $Hal_2CH_2$—, $HalCH_2$—, $Hal_3CO$—, $Hal_2CHO$ or $Hal CH_2O$, wherein Hal represents halo (preferably F); $R^gCH_2O$—, $R^hC(O)NR$—, $R^hSO_2N(R)$— or $R^g$—$R^hN$—, wherein $R^g$ and $R^h$ independently represent hydrogen or $C_{1-8}$alkyl (preferably methyl or $C_{2-6}$alkyl or $C_{2-4}$alkyl), or $R^g$—$R^hN$— represents an optionally substituted $C_{3-8}$, preferably $C_{3-6}$, heterocyclic ring optionally containing from 1 to 3 further heteroatoms independently selected from O, N and S; hydrogen; or $R^kC(O)O$— or $R^kC(O)$—, $R^k$ representing hydrogen, optionally substituted phenyl or $C_{1-6}$alkyl (preferably methyl, ethyl, isopropyl or tert-butyl). For optional substitution of the heterocyclic ring represented by $R^g$—$R^hN$—, at least one (eg, one, two or three) substituents may be provided independently selected from $C_{1-6}$alkyl (eg, $C_{2-4}$alkyl, more preferably methyl); phenyl; $CF_3O$—; $F_2CHO$—; $C_{1-8}$alkoxy, preferably methoxy, ethoxy or $C_{3-6}$alkoxy; $C_{1-8}$alkoxyC(O), preferably methoxycarbonyl, ethoxycarbonyl, tert-butoxycarbonyl or $C_{3-6}$alkoxyC(O); phenoxycarbonyl; phenoxy; $C_{1-8}$alkanoyl, preferably acetyl, ethanoyl or $C_{3-6}$alkyanoyl; carboxy; $C_{1-8}$alkylS(O_{nn})$ wherein nn is an integer between 0 and 2, preferably methylthio, ethylthio, $C_{3-6}$alkylthio, methylsulphinyl, ethylsulphinyl, $C_{3-6}$alkylsulphinyl, methylsulphonyl, ethylsulphonyl or $C_{3-6}$alkylsulphonyl; hydroxy; halo (eg, F, Cl or Br); $R'''R''N$— where $R'''$ and $R''$ are independently hydrogen or $C_{1-6}$alkyl (preferably $C_{2-4}$alkyl, more preferably methyl, most preferably $R'''$=$R''$=methyl); and nitro.

According to a further aspect of the invention there is provided a compound of Formula (Ib)

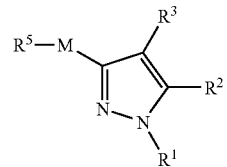

Formula (Ib)

wherein:

$R^1$ represents hydrogen or unsubstituted $C_{1-6}$alkyl;

$R^2$ represents optionally substituted phenyl;

$R^3$ is selected from a group of Formula (IIa) to Formula (IId):

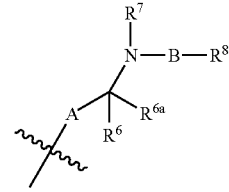

Formula (IIa)

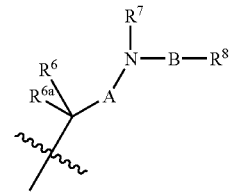

Formula (IIb)

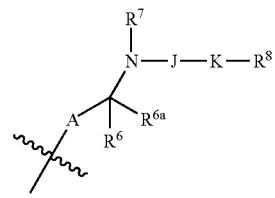

Formula (IIc)

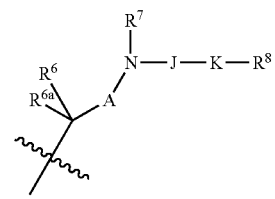

Formula (IId)

$R^5$ is selected from a one of a group of Formula III-a to III-l:

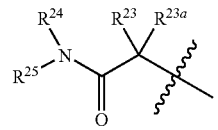

III-a

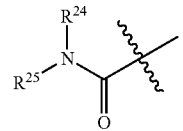

III-b

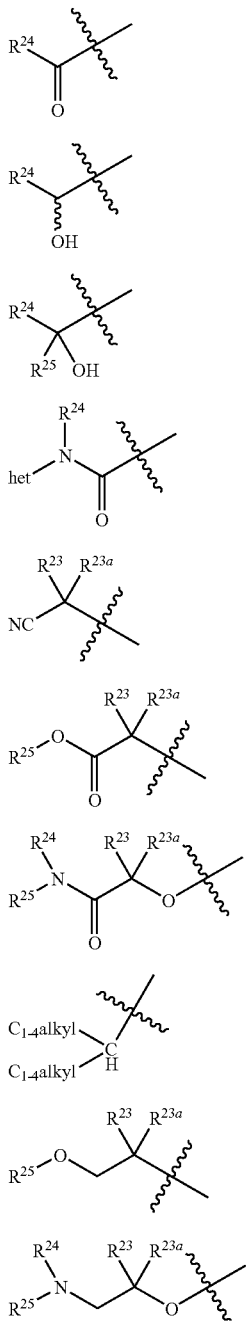

-continued

III-c

III-d

III-e

III-f

III-g

III-h

III-i

III-j

III-k

III-l wherein:
het represents an optionally substituted 3- to 8-membered heterocyclic ring containing from 1 to 4 heteroatoms independently selected from O, N and S;
$R^{23}$ and $R^{23a}$ are independently selected from:
(i) hydrogen or optionally substituted $C_{1-8}$alkyl; or
(ii) $R^{23}$ and $R^{23a}$ together with the carbon to which they are attached form an optionally substituted 3 to 7-membered cycloalkyl ring;
$R^{24}$ and $R^{25}$ are selected from:
(i) $R^{24}$ selected from hydrogen; optionally substituted $C_{1-8}$alkyl; optionally substituted aryl; —$R^d$—Ar, where $R^d$ represents $C_{1-8}$alkylene and Ar represents optionally substituted aryl; and optionally substituted 3- to 8-membered heterocyclic ring optionally containing from 1 to 3 further heteroatoms independently selected from O, N and S; and $R^{25}$ is selected from hydrogen; optionally substituted $C_{1-8}$alkyl and optionally substituted aryl;

(ii) wherein the group of Formula (III) represents a group of Formula III-a, III-b or III-i, then the group $NR^{24}(—R^{25})$ represents an optionally substituted 3- to 8-membered heterocyclic ring optionally containing from 1 to 3 further heteroatoms independently selected from O, N and S; or (iii) wherein the group of Formula (III) represents structure III-e, represents an optionally substituted 3- to 8-membered heterocyclic ring optionally containing from 1 to 4 heteroatoms independently selected from O, N and S;

$R^6$ and $R^{6a}$ are independently selected from hydrogen, fluoro or optionally substituted $C_{1-6}$alkyl.

$R^7$ is selected from: hydrogen or $C_{1-4}$alkyl;

$R^8$ is selected from
(i) hydrogen, $C_{1-6}$alkyl, $C_{2-6}$alkenyl, halo$C_{1-6}$alkyl, hydroxy, cyano, $C_{1-6}$alkylS($O_n$)—, —O—$R^b$, $C_{1-4}$alkoxy$C_{1-4}$alkyl, —C(O)—$R^b$, C(O)O—$R^b$, —NH—C(O)—$R^b$, N,N-di-$C_{1-4}$alkylamino or —S($O_n$)N$R^bR^c$ where $R^b$ and $R^c$ are independently selected from hydrogen and $C_{1-6}$alkyl, and n is 0, 1 or 2;
(ii) -aryl, optionally substituted by up to 4 substituents selected from $R^{12}$, $R^{13}$ and $R^{14}$;
(iii) $C_{4-7}$ heterocyclyl, optionally substituted by up to 4 substituents selected from $R^{12}$, $R^{13}$ and $R^{14}$; or
(iv) $C_{3-7}$carbocyclyl, optionally substituted by up to 4 substituents selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3-7 atoms, optionally substituted heterocyclyl, optionally substituted heterocyclyl$C_{1-6}$alkyl or $R^9$ and $R^{10}$ taken together can form an optionally substituted ring of 3-9 atoms or $R^9$ and $R^{10}$ taken together with the carbon atom to which they are attached form a carbonyl group;

$R^{12}$ is selected from: hydrogen, hydroxy, $R^{17}R^{18}N$ $(CH_2)_{cc}$—, $R^{17}R^{18}NC(O)(CH_2)_{cc}$—, optionally substituted $C_{1-6}$alkyl-C(O)N($R^9$)$(CH_2)_{cc}$—, optionally substituted $C_{1-6}$alkyl-SO$_2$N($R^9$)—, optionally substituted aryl-SO$_2$N($R^9$)—, $C_{1-3}$perfluoroalkyl-SO$_2$N($R^9$)—; optionally substituted $C_{1-6}$alkyl-N($R^9$)SO$_2$—, optionally substituted aryl-N($R^9$SO$_2$—, $C_{1-3}$perfluoroalkyl-N($R^9$)SO$_2$— optionally substituted $C_{1-6}$-alkanoyl-N($R^9$) SO$_2$—; optionally substituted aryl-C(O)N($R^9$)SO$_2$—, optionally substituted $C_{1-6}$alkyl-S($O_n$)—, optionally substituted aryl-S($O_n$)—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl$C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo; A is selected from optionally substituted $C_{1-5}$alkylene, carbonyl or —C(O)—C($R^dR^d$)—, wherein $R^d$ is independently selected from hydrogen and $C_{1-2}$alkyl;

$R^{17}$ is independently selected from: hydrogen, hydroxy, cyano or optionally substituted $C_{1-6}$alkyl;

$R^{18}$ is a group of formula $R^{18a}$—C($R^9R^{10}$)$_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, hydrogen, optionally substituted $C_{1-6}$alkyl, optionally substituted heterocyclyl;

or $R^{17}$ and $R^{18}$ when taken together form an optionally substituted carbocyclic ring of 3-7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

B is selected from optionally substituted $C_{1-6}$alkylene or the group

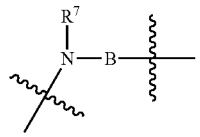

forms an optionally substituted $C_{4-7}$ heterocyclic ring, wherein the optional substituents are selected from $R^{12}$, $R^{13}$ and $R^{14}$;

the group

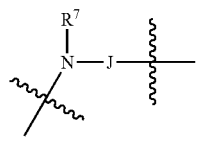

preferably forms an optionally substituted heterocyclic ring containing 4-7 carbons atoms, wherein the optional substituents are selected from $R^{12}$, $R^{13}$ and $R^{14}$;

K is selected from: a direct bond, —(CH$_2$)$_{s1}$—, —(CH$_2$)$_{s2}$—O—(CH$_2$)$_s$—, —(CH$_2$)$_{s1}$—C(O)—(CH$_2$)$_{s2}$—, —(CH$_2$)$_{s1}$—S(O$_n$)—(CH$_2$)$_{s2}$—, —(CH$_2$)$_{s1}$—N(R$^{18}$)—(CH$_2$)$_{s2}$—, —(CH$_2$)$_{s1}$—C(O)N(R$^9$)—(CH$_2$)$_{s2}$—, —(CH$_2$)$_{s1}$—N(R$^9$)C(O)(CH$_2$)$_{s2}$—, —(CH$_2$)$_{s1}$—N(R$^9$)C(O)N(R$^9$)—(CH$_2$)$_{s2}$—, —(CH$_2$)$_{s1}$—OC(O)—(CH$_2$)$_{s2}$—, —(CH$_2$)$_{s1}$—C(O)O—(CH$_2$)$_{s2}$—, —(CH$_2$)$_{s1}$—N(R$^9$)C(O)O—(CH$_2$)$_{s2}$—, —(CH$_2$)$_{s1}$—OC(O)N(R$^9$)(CH$_2$)$_{s2}$, —(CH$_2$)$_{s1}$—OS(O$_n$)(CH$_2$)$_{s2}$, or —(CH$_2$)$_{s1}$—S(O$_n$)—O—(CH$_2$)$_{s2}$—, —(CH$_2$)$_{s1}$—S(O)$_2$N(R$^9$)—(CH$_2$)$_{s2}$—, —(CH$_2$)$_{s1}$—N(R$^9$)S(O)$_2$—(CH$_2$)$_{s2}$—; wherein the —(CH$_2$)$_{s1}$— and —(CH$_2$)$_{s2}$— groups are independently optionally substituted by hydroxy, fluoro, cyano, carbamoyl, $C_{1-4}$alkyl and $C_{1-4}$alkoxy, n is an integer from 0 to 2;

s1 and s2 are independently selected from an integer from 0 to 4, and s1+s2 is less than or equal to 4;

or a salt, pro-drug or solvate thereof.

According to a further aspect of the invention there is provided a compound of Formula (Ic)

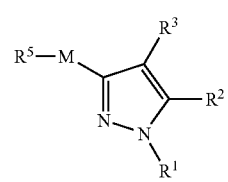

Formula (Ic)

wherein $R^3$ is selected from a group of Formula (IIa) or Formula (IIb):

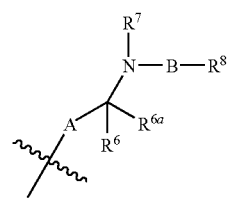

Formula (IIa)

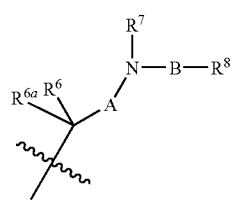

Formula (IIb)

and $R^1$, $R^2$, $R^5$, $R^6$, $R^{6a}$, $R^7$, $R^8$, A, B and M are as defined above;

or salt, solvate or pro-drug thereof.

A further preferred group of compounds of the invention comprises a compound of Formula (Ic), wherein:

A is optionally substituted $C_{1-5}$alkylene;

B is selected from optionally substituted $C_{1-6}$alkylene or the group

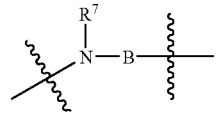

forms a ring containing $C_{5-7}$ heterocyclic ring;

M is —CH$_2$—O—;

$R^1$ is hydrogen or $C_{1-4}$alkyl;

$R^6$ and $R^{6a}$, are independently selected from hydrogen and optionally substituted $C_{1-4}$alkyl;

$R^7$ is selected from: hydrogen or $C_{1-4}$alkyl;

$R^8$ is selected from hydrogen, cyano, $C_{1-6}$alkyl, halo$C_{1-6}$alkyl, $C_{2-6}$alkynyl, $C_{1-6}$alkanoyl, $C_{1-4}$alkoxy$C_{1-4}$alkyl, $C_{1-6}$alkoxycarbonyl, N,N-di-$C_{1-4}$alkylamino, aryl, aryl$C_{1-6}$alkyl, $C_{3-7}$cycloalkyl, $C_{3-7}$cycloalkyl$C_{1-6}$alkyl, heterocyclyl, heterocyclyl$C_{1-6}$alkyl, or heterocyclylcarbonyl$C_{1-4}$alkyl wherein aryl and heterocyclyl rings are optionally substituted by cyano and $C_{1-4}$alkyl; and $R^2$ and $R^5$; are as defined above or salt, solvate or pro-drug thereof.

A further preferred group of compounds of the invention comprises a compound of Formula (Ic), wherein:

A is optionally substituted $C_{1-5}$alkylene;

B is selected from optionally substituted $C_{1-6}$alkylene or the group

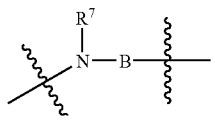

forms a ring containing $C_{5-7}$ heterocyclic ring;

$R^1$ is hydrogen or $C_{1-4}$alkyl, preferably hydrogen;

$R^2$ is an optionally substituted monocyclic aromatic ring structure, preferably optionally substituted phenyl, most preferably 3,5-dimethylphen-1-yl;

$R^5$ is a group of Formula (III) wherein the group of Formula (III) is selected from a group of Formula III-a; III-b; III-c; III-d; III-e; III-f, III-g, III-h, III-I, III-j, III-k and III-l;

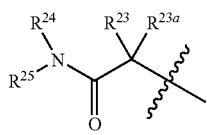
III-a

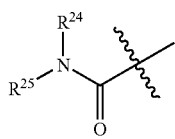
III-b

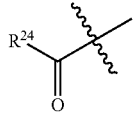
III-c

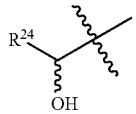
III-d

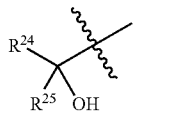
III-e

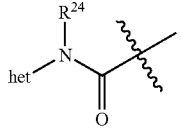
III-f

-continued

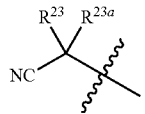
III-g

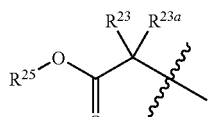
III-h

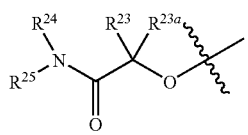
III-i

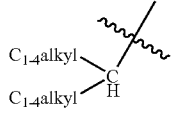
III-j

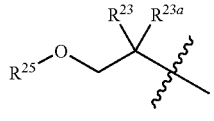
III-k

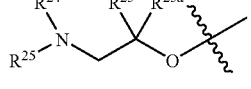
III-l wherein $R^{23}$, $R^{23a}$, $R^{24}$ and $R^{25}$ are as defined above, preferably the group of Formula (III) is selected from (III-a), (III-g) and (III-h);

$R^6$ and $R^{6a}$, are independently selected from hydrogen and optionally substituted $C_{1-4}$alkyl;

$R^7$ is selected from: hydrogen or $C_{1-4}$alkyl;

$R^8$ is selected from hydrogen, cyano, $C_{1-6}$alkyl, halo$C_{1-6}$alkyl, $C_{2-6}$alkynyl, $C_{1-6}$alkanoyl, $C_{1-4}$alkoxy$C_{1-4}$alkyl, $C_{1-6}$alkoxycarbonyl, N,N-di-$C_{1-4}$alkylamino, aryl, aryl$C_{1-6}$alkyl, $C_{3-7}$cycloalkyl, $C_{3-7}$cycloalkyl$C_{1-6}$alkyl, heterocyclyl, heterocyclyl$C_{1-6}$alkyl, or heterocyclylcarbonyl$C_{1-4}$alkyl wherein aryl and heterocyclyl rings are optionally substituted by cyano and $C_{1-4}$alkyl; and $R^2$, and $R^5$; are as defined above or salt, solvate or pro-drug thereof.

A further preferred group of compounds of the invention comprises a compound of Formula (Id):

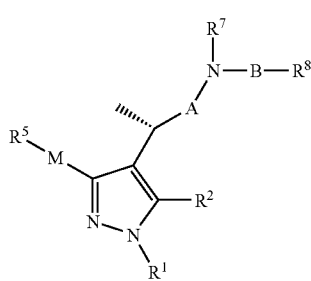

Formula (Id)

Wherein $R^1$, $R^2$, $R^5$; $R^7$, $R^8$, A, B and M are as defined above or salt, solvate or pro-drug thereof.

A yet further preferred group of compounds of the invention comprises a compound of Formula (Ib), (Ic) or (Id) wherein:

$R^5$ is a group of Formula (III) wherein the group of Formula (III) is a group of formula IIIa:

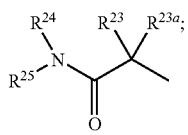

wherein $R^{23}$, $R^{23a}$, $R^{24}$ and $R^{25}$ are as defined above;

or a salt, pro-drug or solvate thereof.

According to a further aspect of the invention there is provided a compound of Formula (I) or Formula (Ia), or salt, solvate or pro-drug thereof, wherein $R^3$ is selected from a group of Formula (IIc) or Formula (IId) and $R^1$, $R^2$ and $R^5$ are as defined above.

According to a further aspect of the invention there is provided a compound of Formula (I) or Formula (Ia), or salt, solvate or pro-drug thereof, wherein $R^3$ is selected from a group of Formula (IIe) or Formula (IIf) and $R^1$, $R^2$ and $R^5$ are as defined above.

According to a further aspect of the invention there is provided a compound of Formula (I) or Formula (Ia), or salt, solvate or pro-drug thereof, wherein $R^3$ is selected from a group of Formula (IIa), Formula (IIc) or Formula (IIe) and $R^1$, $R^2$ and $R^5$ are as defined above.

According to a further aspect of the invention there is provided a compound of Formula (I) or Formula (Ia), or salt, solvate or prodrug thereof, wherein $R^3$ is selected from a group of Formula (IIb), Formula (IId) or Formula (IIf) and $R^1$, $R^2$ and $R^5$ are as defined above.

Particularly preferred compounds according to the present invention are wherein the compound is selected from:

2-[3-(2,2-dimethyl-3-oxo-3-{azabicyclo[2.2.1]heptan-7-yl}propoxy)-5-3,5-dimethylphenyl)-1H-pyrazol-4-yl]-N-[2-(1,3-benzodioxol-5-yl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylbutyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[4-(4-methoxyphenyl)butyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-phenylethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(43-trifluoromethylphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-fluorophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(3-fluorophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(3-methoxyphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-methoxyphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(3,4-difluorophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-isopropylureidophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-{cyclopentylcarbonylamino}phenyl)ethyl]-(2S)-propylamine;

[2-(4-methylsulphonylaminophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-{isopropoxycarbonylamino}phenyl)ethyl]-(2S) propylamine;

2-[3-(2,2-diethyl-3-oxo-3-{azabicyclo[2.2.1]heptan-7-yl}propoxy)-5-(3,5-dimethylphenyl)-1H-pyrazol-4-yl]-N-[2-(4-{cyclohexylureido}phenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(1-methyl-2-oxo-1,2-dihydroquinolin-6-yl)ethyl]-(2S)propylamine;

3-[2,2-dimethyl-3-oxo-3-(azabicyclo[2.2.2]oct-2-yl)propoxy]-5-(3,5-dimethylphenyl)-1H-pyrazol-4-yl]-N-[2-(3-methoxyphenyl)ethyl]-(2S)-propylamine; and 2-[3-(2,2-dimethyl-3-oxo-3-{azabicyclo[2.2.2]oct-2-yl}propoxy)-5-(3,5-dimethylphenyl)-1H-pyrazol-4-yl]-N-[2-(1,3-benzodioxol-5-yl)ethyl]-(2S)-propylamine;

or a salt, pro-drug or solvate thereof.

More particularly preferred compounds according to the present invention are wherein the compound is selected from:

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(1,3-benzodioxol-5-yl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylbutyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[4-(4-methoxyphenyl)butyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(43-trifluoromethylphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-fluorophenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(3-methoxyphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-methoxyphenyl)ethyl]-(2S)-propylamine;

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-methylsulphonylaminophenyl)ethyl]-(2S)-propylamine; and 2-[3-(2,2-dimethyl-3-oxo-3-{azabicyclo[2.2.2]oct-2-yl}propoxy)-5-(3,5-dimethylphenyl)-1H-pyrazol-4-yl]-N-[2-(1,3-benzodioxol-5-yl)ethyl]-(2S)propylamine;

or a salt, pro-drug or solvate thereof.

Most preferred compounds according to the present invention are wherein the compound is selected from:

2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(1,3-benzodioxol-5-yl)ethyl]-(2S)-propylamine; and 2-[3-(2,2-dimethyl-3-oxo-3-{azabicyclo[2.2.2]oct-2-yl}propoxy)-5-(3,5-dimethylphenyl)-1H-pyrazol-4-yl]-N-[2-(1,3-benzodioxol-5-yl)ethyl]-(2S)-propylamine;

or a salt, pro-drug or solvate thereof.

In another embodiment of the invention preferred compounds according to the present invention are wherein the compound is selected from:

2-[3-(2,2-dimethyl-3-oxo-3-pyrrolidin-1-ylpropoxy)-5-(3,5-dimethylphenyl)-1H-pyrazol-4-yl]-N-(2-pyridin-4-yl-ethyl)ethanamine;

2-[3-(2,2-dimethyl-3-oxo-3-pyrrolidin-1-ylpropoxy)-5-(3,5-dimethylphenyl)-1H-pyrazol-4-yl]-N-(2-pyridin-4-ylbutyl)ethanamine;

2-[3-(2,2-dimethyl-3-oxo-3-(7-azabicyclo[2.2.1]hept-7-yl)propoxy)-5-(3,5-dimethylphenyl)-1H-pyrazol-4-yl]-N-(2-pyridin-4-ylethyl)ethanamine; and 2-[3-(2,2-dimethyl-3-oxo-3-(7-azabicyclo[2.2.1]hept-7-yl)propoxy)-5-(3,5-dimethylphenyl)-1H-pyrazol-4-yl]-N-(2-pyridin-4-ylbutyl)ethanamine;

or a salt, pro-drug or solvate thereof.

The compounds of Formula (I) may be administered in the form of a pro-drug which is broken down in the human or animal body to give a compound of the Formula (I). Examples of pro-drugs include in-vivo hydrolysable esters of a compound of the Formula (I). Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309-396, edited by K Widder, et al. (Academic Press, 1985);

b) A Textbook of Drug Design and Development, edited by Krogsgaard-Larsen and H. Bundgaard, Chapter 5 "Design and Application of Prodrugs", by He Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula (I) containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters, for example 5-methyl-1,3-dioxolen-2-onylmethyl; and $C_{1-6}$alkoxycarbonyloxyethyl esters.

An in-vivo hydrolysable ester of a compound of the Formula (I) containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethyl-propionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of Formula (I) can be prepared by a process comprising a step selected from (a) to (h) as follows, these processes are provided as a further feature of the invention:—

(a) Reaction of a compound of formula XXXII with a compound of formula $L^2$-$R^{5'}$ to form a compound of Formula (I),

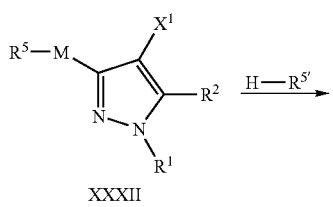

XXXII

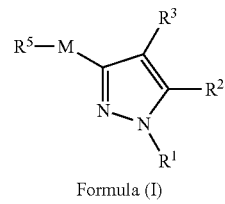

Formula (I)

wherein $X^1$ is selected from

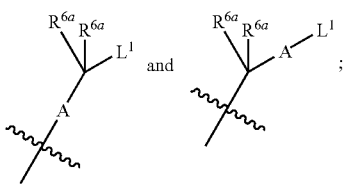

$L^1$ is a displaceable group; and

H—$R^{5'}$ is selected from:

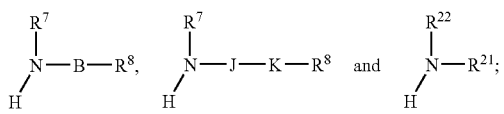

(b) Reaction of a compound of formula XXXIII with a compound of formula H—R$^{5''}$ to form a compound of Formula (I),

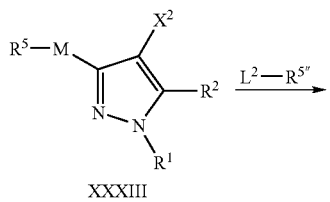

XXXIII

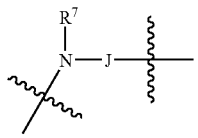

Formula (I)

wherein X$^2$ is selected from:

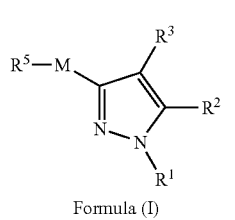

L$^2$ is a displaceable group and R$^{7a}$ is selected from the definition of R$^7$ or R$^{22}$ above, and
L$^2$-R$^{5''}$ is selected from: L$^2$-B—R$^8$, L$^2$-J-K—R$^8$ and L$^2$-R$^{21}$ (c) For compounds of Formula (I) wherein R$^3$ is a group of Formula (IIa), (IIb), (IIc) or (IId) and R$^7$ is other than part of a heterocyclic ring or hydrogen, reaction of a compound of Formula (I) wherein R$^3$ is a group of Formula (IIa), (IIb), (IIc) or (IId) and R$^7$ is hydrogen with a group of formula L$^3$-R$^{7a}$, wherein R$^{7a}$ is as defined above for R$^7$ with the exclusion of hydrogen and L$^3$ is a displaceable group;

(d) For compounds of Formula (I) wherein R$^3$ is a group of Formula (IIe) or (IIf) and R$^{21}$ is other than hydrogen, reaction of a compound of Formula (I) wherein R$^3$ is a group of Formula (IIe) or (IIf) and R$^{21}$ is hydrogen with a group of formula L$^4$-R$^{21a}$, wherein R$^{21a}$ is as defined above for R$^{21}$ with the exclusion of hydrogen and L$^4$ is a displaceable group;

(e) For compounds of Formula (I) wherein R$^3$ is a group of Formula (IIe) or (IIf) and R$^{22}$ is other than hydrogen, reaction of a compound of Formula (I) wherein R$^3$ is a group of Formula (IIe) or (IIf) and R$^{22}$ is hydrogen with a group of formula L$^5$-R$^{22a}$, wherein R$^{22a}$ is as defined above for R$^{22}$ with the exclusion of hydrogen and L$^5$ is a displaceable group;

(f) For compounds of Formula (I) wherein R$^3$ is a group of Formula (IIc) or (IId) and the group

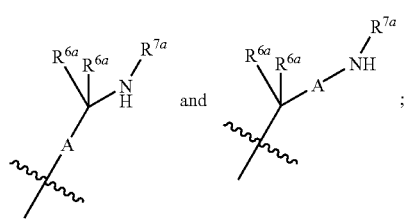

together forms an optionally substituted nitrogen-containing heterocyclic ring containing 47 carbons atoms, reaction of a compound of Formula XXXIVa or XXXIVb, with a compound of Formula L$^6$-K—R$^8$, wherein L$^6$ is a displaceable group

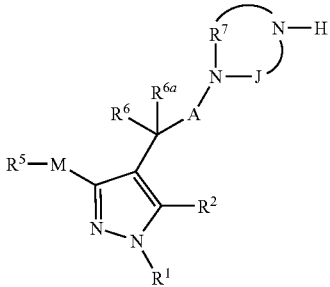

XXXIVa

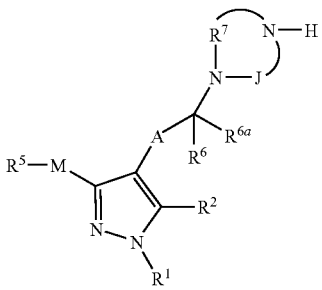

XXXIVb (g) For compounds of Formula (I) wherein R$^3$ is a group of Formula (IIc) or (IId), reaction of a compound of Formula XXXVa or XXXVb, with a compound of Formula L$^7$-K''—R$^8$, wherein L$^7$ is a displaceable group, and wherein the groups K' and K'' comprise groups which when reacted together form K,

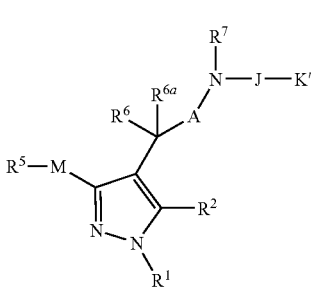

XXXVa

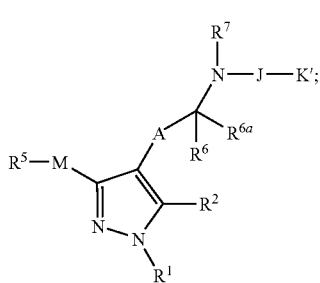

(h) reaction of a compound of Formula XXXVI with an electrophillic compound of the formula $L^8$-$R^5$, wherein $L^8$ is a displaceable group

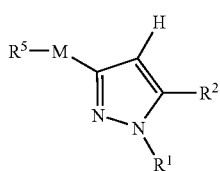

and thereafter if necessary:
i) converting a compound of the Formula (I) into another compound of the Formula (I);
ii) removing any protecting groups;
iii) forming a salt, pro-drug or solvate.

Specific reaction conditions for the above reations are as follows:

Process a) Compounds of formula XXXII and H—$R^{5'}$ can be coupled together in the presence of an organic base (such as DIPEA [di-isopropylethylamine]) or an inorganic base (such as potassium carbonate) base, in a suitable solvent such as DMA or DMF, at a temperature from room temperature and 120° C. Suitable displaceable groups include: a halide, such as chloro, or a methane sulphonate or toluene sulphonate;

Process b) Compounds of XXXIII and $L^2$-$R^{5'''}$ can be coupled together in the presence of an organic base (such as DIPEA) or an inorganic base (such as potassium carbonate), in a suitable solvent such as DMA or DMF, at a temperature from room temperature to 120° C. Suitable displaceable groups include: a halide, such as chloro, or a methane sulphonate or toluene sulphonate, alternatively if $L^2$ is a hydroxy group then the $L^2$-$R^{5'}$; can be reacted with a compound of formula XXXIII under Mitsunobu reaction conditions;

Process c, d, e and f) Reaction conditions to facilitate these reactions can be using (i) alkylation reaction conditions or (ii) acylation reaction conditions: Examples of said conditions include:
  (i) alkylation reaction conditions—the presence of an organic base (such as DIPEA) or an inorganic base (such as potassium carbonate), in a suitable solvent such as DMF, DMA, DCM, at a temperature from room temperature to 120° C. Suitable displaceable groups include: a halide, such as chloro, methane sulphonate or toluene sulphonate;
  (ii) acylation reaction conditions—presence of organic base, such as triethylamine, temperature 0° C. to 50-60° C. in a suitable solvent such as DCM. Suitable displaceable groups include an acylchloride or an acid anhydride, Process g) The skilled man would be familiar with a variety of reaction conditions and values for K' and K", which when reacted together would form the group K, examples of said conditions and values for K' and K" include:
  (i.) For compounds of Formula (I) where K is —$(CH_2)_{s1}$—$N(R^9)C(O)$—$(CH_2)_{s2}$— these can be prepared by reacting a compound where K' is —$(CH_2)_{s1}$—$N(R^9)H$ with a carboxylic acid for formula HOOC—$(CH_2)_{s2}$—$R^8$ to form the amide. Coupling of amino groups with carboxylic acids are well known in the art and can be facilitated by a number of chemical reactions using an appropriate coupling reagent. For example a carbodiimide coupling reaction can be performed with EDCl in the presence of DMAP in a suitable solvent such as DCM, chloroform or DMF at room temperature;
  (ii.) For compounds of Formula (I) where K is —$(CH_2)_{s1}$—$C(O)N(R^9)$—$(CH_2)_{s2}$— these can be prepared by reacting a compound where K' is —$(CH_2)_{s1}$—COOH with an amine of the $HN(R^9)$—$(CH_2)_{s2}$—$R^8$ to form the amide. Methodology is identical to processes described in (i) above in this section;
  (iii.) For compounds of Formula (I) where K is —$(CH_2)_{s1}$—$N(R^9)C(O)O$—$(CH_2)_{s2}$— these can be prepared by reacting a compound where K' is —$(CH_2)_{s1}$—$N(R^9)H$ with a chloroformate of formula ClC(O)O—$(CH_2)_{s2}R^8$ in a suitable solvent, such as DCM or chloroform, in the presence of a base, such as N-methylmorpholine, pyridine or triethylamine, at a temperature between −10° C. and 0° C.;
  (iv.) For compounds of Formula (I) where K is —$(CH_2)_{s1}$—$OC(O)N(R^9)$—$(CH_2)_{s2}$— these can be prepared by reacting a compound where K' is —$(CH_2)_{s1}$—OC(O)Cl with a compound of formula $HN(R^9)$—$(CH_2)_{s2}$—$R^8$. Methodology is identical to processes described in (iii) above in this section;
  (v.) For compounds of Formula (I) where K is —$(CH_2)_{s1}$—$N(R^9)S(O_2)$—$(CH_2)_{s2}$— these can be prepared by reacting a compound where K' is —$(CH_2)_{s1}$—$N(R^9)H$ with a sulphonyl chloride of formula $ClS(O_2)$—$(CH_2)_{s2}$—$R^8$ in the presence of a base, such as triethylamine or pyridine, in a suitable solvent such as chloroform or DCM at a temperature between 0° C. and room temperature;
  (vi.) For compounds of Formula (I) where K is —$(CH_2)_{s1}$—$S(O_2)N(R^9)$—$(CH_2)_{s2}$— these can be prepared by reacting a compound where K' is —$(CH_2)_{s1}$—S(O2)Cl with a compound of $HN(R^9)$—$(CH_2)_{s2}$—$R^8$. Methodology is identical to processes described in (v) above in this section
  (vii.) For compounds of Formula (I) where K is —$(CH_2)_{s1}$—$N(R^9)$—$(CH_2)_{s2}$— these can be prepared by reacting a compound where K' is —$(CH_2)_{s1}$-$L^{11}$ with a compound of formula $HN(R^9)$—$(CH_2)_{s2}$—$R^8$, wherein $L^{11}$ is a displaceable group. This reaction can be performed in the presence of an organic base (such as DIPEA) or an inorganic base (such as potassium carbonate), in a suitable solvent such as DMA or DMF, at a temperature from room temperature to 120° C. Suitable displaceable groups include: a halide, such as chloro, or a methane sulphonate or toluene sulphonate. Compounds can also be prepared by reacting a compound wherein K' is —$(CH_2)_{s1}$—$N(R^9)H$ with a compound of formula $L^{11}$-$(CH_2)_{s2}$—$R^8$, under identical conditions.

(viii.) For compounds of Formula (I) where K is —$(CH_2)_{s1}$—O—$(CH_2)_{s2}$— these can be prepared by reacting a compound where K' is —$(CH_2)_{s1}$—OH with a compound of formula $L^{12}$-$(CH_2)_{s2}$—$R^8$, wherein $L^{12}$ is a displaceable group. This reaction can be performed in the presence of an organic base (such as potassium t-butoxide) or an inorganic base (such as sodium hydride), in a suitable solvent such as DMA or DMF, at a temperature from room temperature and 120° C. Suitable displaceable groups include: a halide, such as bromo, or a methane sulphonate or toluene sulphonate. Compounds can also be prepared by reacting a compound wherein K' is —$(CH_2)_{s1}$-$L^{12}$ with a compound of formula HO—$(CH_2)_{s2}$—$R^8$, under identical conditions.

(ix.) For compounds of Formula (I) where K is —$(CH_2)_{s1}$—C(O)—$(CH_2)_{s2}$— these can be prepared by reacting a compound where K' is —$(CH_2)_{s1}$—C(O)-$L^{13}$ with a Grignard reagent of formula $BrMg(CH_2)_{s2}$—$R^8$, wherein $L^{13}$ is a displaceable group. This reaction can be performed in a non-polar solvent such as THF or diethylether at a temperature between room temperature and the boiling point of the solvent. Suitable displaceable groups include: a halide, such as bromo, or a methane sulphonate or toluene sulphonate. Compounds can also be prepared by reacting a compound wherein K' is —$(CH_2)_{s1}$—MgBr with a compound of formula $L^{13}$-C(O)—$(CH_2)_{s2}$—$R^8$, under identical conditions.

Process h) reaction of a compound of Formula XXXVI with a compound of the formula $L^8$-$R^5$, can be performed under Friedel Craft conditions, for example in the presence of diethylaluminium chloride in a suitable solvent, such as DCM, in an inert atmosphere such as nitrogen, at a temperature between room temperature and the boiling point of the solvent or under Mannich conditions, for example, formaldehyde and a primary or secondary amine in acetic acid, in an inert atmosphere such as nitrogen at a temperature between room temperature and 100° C. It will be appreciated by those skilled in the art that in the processes of the present invention certain functional groups such as hydroxyl or amino groups in the starting reagents or intermediate compounds may need to be protected by protecting groups. Thus, the preparation of the compounds of Formula (I) may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

Experimental

General Reaction Schemes

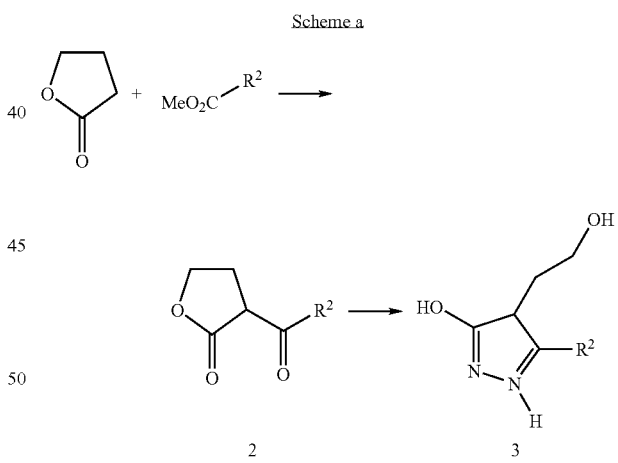

Pyrazoles, such as 3 can be synthesised in two steps (Scheme a):

(1) by the reaction of a lactone with the appropriate ester using a Claisen condensation to form a compound of formula 2, under conditions of an inert atmosphere, such as argon, at a temperature of about 0° C. in a suitable solvent such as TBH.

(2) followed by cyclization of a compound of formula 2 with hydrazine to form the pyrazole 3, at a room temperature in a suitable solvent such as ethanol.

Scheme b

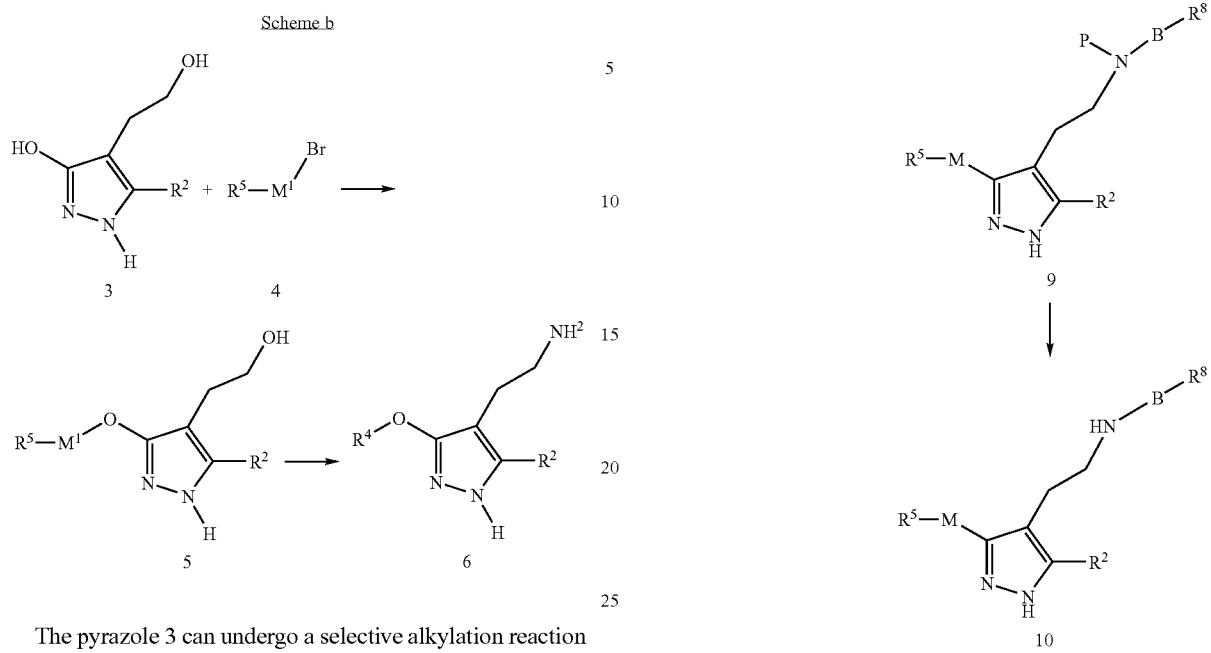

The pyrazole 3 can undergo a selective alkylation reaction with a compound of formula 4, under conditions of an inert atmosphere, such as argon, in the presence of a suitable base, such as potassium carbonate in the a suitable solvent such as DMA at a temperature of about 90° C., to form a compound of formula 5. Then the amine 6 can be prepared from a compound of formula 5 and phthalimide using a Mitsunobu reaction with an activating agent such as diethyldiazocarboxylate (DEAD), diisopropyldiazocarboxylate or the like with triphenylphosphine, tri-butylphosphine and the like, in an inert solvent such as benzene, toluene, tetrahydrofuran or mixtures thereof, followec by deprotection with hydrazine to give the (Scheme b).

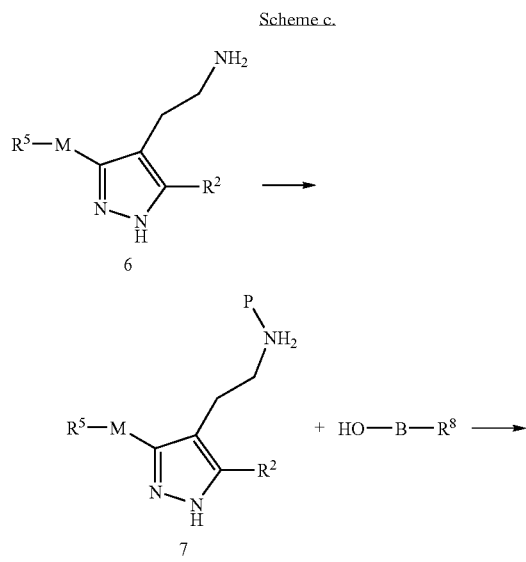

A suitable pyrazole 6 can be converted to a compound of formula 10 by incorporation of a suitable protecting group (P) to form a compound of formula 7, followed by a Mitsunobu reaction with a suitable alcohol 8 to form a compound of formula 9, followed by deprotection.

EXAMPLES

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

(vii) isolute™ refers to silica ($SiO_2$) based columns with irregular particles with an average size of 50 μm with nominal 60 Å porosity [Source: Jones Chromatography, Ltd., Glamorgan, Wales, United Kingdom].

Abbreviations
boc t-butoxycarbonyl
DCC 1,3-dicyclohexylcarbodiimide

DEAD diethylazodicarboxylate
DMA dimethylacetamide
DMAP 4-dimethylaminopyridine
DMSO dimethyl sulphoxide
DMF dimethylformamide
DNS 2,4-dinitrobenzenesulphonyl
EDC 1-(3-dimethylaminopropyl)-3-ethylcarbodiimide hydrochloride
HOBt 1-hydroxybenzotriazole
LHMDS lithium bis(trimethylsilyl)amide
THF tetrahydrofuran Example 1

2-[3-(2,2-dimethyl-3-oxo-3-pyrrolidin-1-ylpropoxy)-5-(3,5-dimethylphenyl)-1H-pyrazol-4-yl]-N-(2-pyridin-4-ylethyl)ethanamine

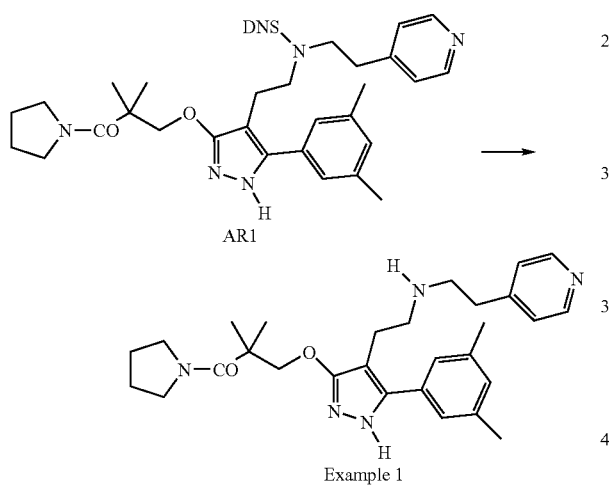

A solution of AR1 (123 mg; 0.17 mmol) in CH₂Cl₂ (3 ml) was treated dropwise with propylamine (140 ul; 1.7 mmol). The mixture was stirred at room temperature for 1 h and then purified directly by flash chromatography eluting with increasingly polar mixtures of EtOAc/CH₂Cl₂ (50 to 100% EtOAc) and then MeOH/CH₂Cl₂ (0 to 10% MeOH) to give Example 1 as a beige solid (83 mg).

Yield: 100%

¹H NMR spectrum (DMSO d₆): 1.27 (s, 6H); 1.75 (m, 4H); 2.3 (s, 6H); 2.55-2.95 (m, 8H); 3.5 (m, 4H); 4.18 (s, 2H); 7.03 (s, 1H); 7.10 (s, 2H); 7.2 (d, 2H); 8.44 (d, 2H); 11.9 (s br, 1H).

MS-ESI: 490 [M+H]⁺

The starting material AR1 was prepared as follows:—

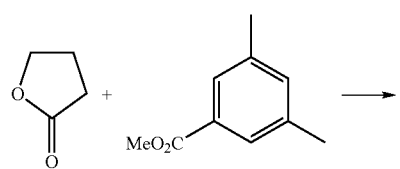

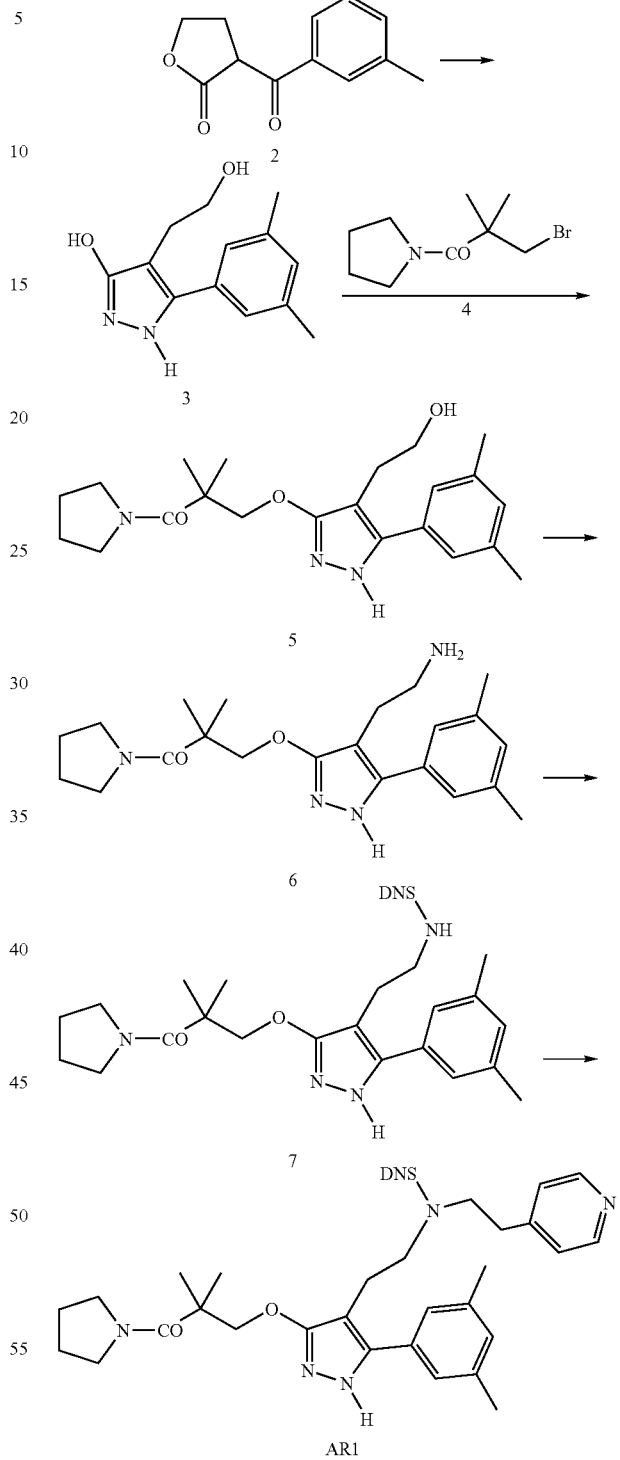

A solution of methyl 3,5-dimethylbenzoate (25 g; 152 mmol) and butyrolactone (40 ml; 520 mmol) in THF (300 ml) under argon was cooled to 0° C. and treated dropwise with LHMDS (200 ml; 200 mmol; 1M in hexanes). The mixture was stirred and allowed to warm to room temperature overnight. The THF was evaporated. The residue was taken up in Et₂O and the organic phase was washed with sat. aq. NaHCO₃, brine and dried over MgSO₄. The residue was purified by flash chromatography eluting with increasingly polar mixtures of EtOAc/hexanes (20 to 40% EtOAc) to give an oil which slowly crystallised to give 2 as a white solid (9.2 g). During the chromatography, the starting material methyl 3,5-dimethylbenzoate (12.4 g) was recovered.

Yield: 55% based on recovered methyl 3,5-dimethylbenzoate.

$^1$H NMR spectrum (CDCl$_3$): 2.39 (s, 6H); 2.5 (m, 1H); 2.82 (m, 1H); 4.41 (m, 1H); 4.51 (m, 2H); 7.25 (s, 1H); 7.65 (s, 2H).

MS-ESI: 219 [M+H]$^+$

Compound 2 (7.43 g; 34 mmol) was dissolved in EtOH (200 ml) and hydrazine hydrate (17.2 ml; 354 mmol) was added. The mixture was stirred for 30 min. The solvent was evaporated and the residue was triturated with pentane to give 3 as a white solid (7.05 g).

Yield: 90%

$^1$H NMR spectrum (DMSO d$_6$): 2.32 (s, 6H); 2.58 (t, 2H); 3.50 (t, 2H); 4.8 (br s, 1H); 7.01 (s, 1H); 7.14 (s, 2H); 9.5 (br s, 1H).

MS-ESI: 233 [M+H]$^+$

A mixture of 3 (4.26 g; 18.4 mmol) and 4 (4.51 g; 19.3 mmol) in DMA (40 ml) under argon was treated with K$_2$CO$_3$ (5.07 g; 36.7 mmol). The mixture was stirred and heated at 90° C. for 2 h. The mixture was poured into sat. aq. NaHCO$_3$, extracted with EtOAc and the organic phase was washed with water, brine and dried over MgSO$_4$. The residue was purified by flash chromatography eluting with increasingly polar mixtures of EtOAc/CH$_2$Cl$_2$ (0 to 100% EtOAc) to give the alcohol 5 as a pale yellow oil (6.56 g).

Yield: 93%

$^1$H NMR spectrum (DMSO d$_6$): 1.30 (s, 6H); 1.8 (m, 4H); 2.33 (s, 6H); 2.55 (m, 2H); 3.32 (m, 2H); 3.5 (m, 4H); 4.17 (s, 2H); 4.62 (t, 1H); 7.04 (s, 1H); 7.16 (s, 2H); 11.9 (br s, 1H).

MS-ESI: 386 [M+H]$^+$

A mixture of 5 (3.85 g; 10 mmol), phthalimide (1.62 g; 11 mmol) and triphenylphosphine (10.5 g; 40 mmol) in THF (100 ml) at 0° C. under argon was treated with DEAD (6.33 ml; 40 mmol). The mixture was stirred at this temperature for 1 h when water was added. The mixture was extracted with Et$_2$O and the organic phase was washed with water, brine and dried over MgSO$_4$.

Evaporation gave a crude solid which, without further purification, was immediately taken up in EtOH (50 ml) and treated with hydrazine hydrate (5 ml; 100 mmol). The mixture was stirred for 1.5 h and then the EtOH was partially evaporated. Addition of CH$_2$Cl$_2$ caused precipitation of phthalhydrazide which was filtered and rinsed with CH$_2$Cl$_2$. The filtrate was evaporated and the residue was purified by flash chromatography eluting with increasingly polar mixtures of EtOAc/CH$_2$Cl$_2$ (0 to 100% EtOAc) and then MeOH/CH$_2$Cl$_2$ (0 to 8% MeOH) to give 6 as a beige solid (2.34 g).

Yield: 61%

$^1$H NMR spectrum (DMSO d$_6$): 1.30 (s, 6H); 1.79 (m, 4H); 2.33 (s, 6H); 2.52 (m, 2H); 2.67 (t, 2H); 3.5 (m, 4H); 4.18 (s, 2H); 7.03 (s, 1H); 7.14 (s, 2H); 8.95 (br s, 1H).

MS-ESI: 385 [M+H]$^+$

A solution of 6 (200 mg; 0.52 mmol) in CH$_2$Cl$_2$ (5 ml) was treated with diisopropylethylamine (135 ul; 0.78 mmol) and cooled to 0° C. A solution of 2,4-dinitrobenzenesulphonyl chloride (153 mg; 0.57 mmol) in CH$_2$Cl$_2$ (1 ml) was added dropwise and the mixture was allowed to warm to room temperature for 30 min. The mixture was purified directly by flash chromatography eluting with increasingly polar mixtures of EtOAc/CH$_1$Cl$_2$ (0 to 50% EtOAc) to give 7 as a cream solid (224 mg).

Yield: 70%

$^1$H NMR spectrum (DMSO d$_6$): 1.24 (s, 6H); 1.75 (m, 4H); 2.29 (s, 6H); 2.57 (m, 2H); 3.11 (m, 2H); 3.5 (m, 4H); 4.15 (s, 2H); 7.0 (s, 1H); 7.03 (s, 2H); 8.14 (d, 1H); 8.56 (q, 1H); 8.6 (br s, 1H); 8.83 (d, 1H).

MS-ESI: 615 [M+H]$^+$

A mixture of 7 (170 mg; 0.27 mmol), 4-(2-hydroxyethyl)-pyridine (38 mg; 0.3 mmol) and triphenylphosphine (283 mg; 1.08 mmol) in THF (10 ml) at 0° C. under argon was treated with DEAD (170 ul; 1.08 mmol). The mixture was allowed to warm to room temperature for 30 min. when water was added. The mixture was extracted with EtOAc and the organic phase was washed with water, brine and dried over MgSO$_4$. The residue was purified by flash chromatography eluting with increasingly polar mixtures of EtOAc/CH$_2$Cl, (0 to 100% EtOAc) AR1 as a white solid (123 mg).

Yield: 63%

$^1$H NMR spectrum (DMSO d$_6$): 1.27 (s, 6H); 1.7 (m, 4H); 2.28 (s, 6H); 2.69 (t, 2H); 2.83 (t, 2H); 3.4 (m, 4H); 3.48 (t, 2H); 3.56 (t, 2H); 4.21 (s, 2H); 7.01 (s, 1H); 7.08 (s, 2H); 7.19 (d, 2H); 8.15 (d, 1H); 8.41 (d, 2H); 8.42 (q, 1H); 8.89 (d, 1H).

MS-ESI: 720 [M+H]$^+$

Starting material 4 was prepared as follows:—

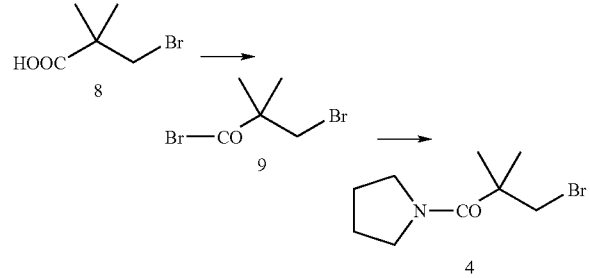

A mixture of 8 (14.48 g; 80 mmol) and oxalyl bromide (43.2 g; 200 mmol) containing one drop of DMF was heated at 50° C. for 2 h and then cooled. The excess of oxalyl bromide was evaporated and the residue azeotroped with toluene to give crude 9 which was taken up directly in CH$_2$Cl$_2$ (25 ml) and cooled to 0° C. Diisopropylethylamine (14 ml; 80 mmol) was added followed by a solution of pyrrolidine (3.3 ml; 40 mmol) in CH$_2$Cl$_2$ (30 ml). The mixture was allowed to warm to room temperature overnight and was diluted with CH$_2$Cl$_2$, washed with aq. HCl (2N), aq. NaOH (1N), water, brine and dried over MgSO4. The residue was purified by flash chromatography eluting with increasingly polar mixtures of EtOAc/CH$_2$Cl$_2$ (5 to 10% EtOAc) to give 4 as a white solid (6.5 g).

Yield: 70%

$^1$H NMR spectrum (DMSO d$_6$): 1.39 (s, 6H); 1.9 (m, 4H); 3.57 (m, 4H); 3.62 (s, 2H)

MS-ESI: 235 [M+H]$^+$

Examples 1.1-1.5

The following examples were prepared in a similar manner to Example 1,

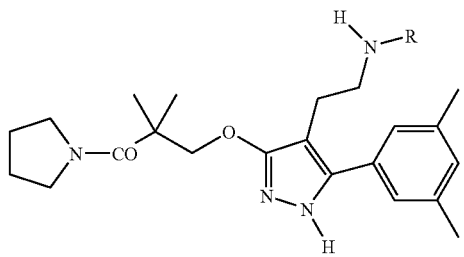

the table shows the R group relating to the above structure, the reaction conditions and characteristics for each example, corresponding to the description of the preparation of Example 1 given above:—

Example 1.1

| R | AR2 mg; mmol | CH$_2$Cl$_2$ ml | Propylamine μl; mmol | Prod. Form | Mass mg; Yield | MS-ESI |
|---|---|---|---|---|---|---|
| 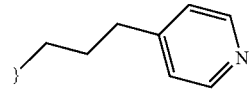 | 210; 0.28 | 5 | 235; 2.86 | White solid | 111; 77% | 504 [M + H]$^+$ |

Chromato.-EtOAc and then MeOH/CH$_2$Cl$_2$ (0 to 10% MeOH)
$^1$H NMR spectrum (DMSO d$_6$): 1.27(s, 6H); 1.75(m, 4H); 2.31(s, 6H); 2.57-2.63(m, 6H); 2.75(m, 2H); 3.3-3.7(m, 4H); 4.18(s, 2H); 7.03(s, 1H); 7.11(s, 2H); 7.2(d, 2H); 8.44(d, 2H); 11.9(s br, 1H).

Example 1.2

| R | AR3 mg; mmol | CH$_2$Cl$_2$ ml | Propylamine μl; mmol | Prod. Form | Mass mg; Yield | MS-ESI |
|---|---|---|---|---|---|---|
| 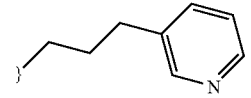 | 120; 0.16 | 3 | 135; 163 | White solid | 60; 73% | 504 [M + H]$^+$ |

Chromato.-Ammonia in MeOH(7 N)/(CH$_2$Cl$_2$ (0 to 10% ammonia in MeOH)
$^1$H NMR spectrum (DMSO d$_6$): 1.27(s, 6H); 1.6-1.9(m, 6H); 2.3(s, 6H); 2.55-2.64(m, 6H); 2.7(m, 2H); 3.3-3.6(m, 4H); 4.17(s, 2H); 7.02(s, 1H); 7.12(s, 2H); 7.29(dd, 1H); 7.58(d, 1H); 8.39(d, 1H); 11.9(s br, 1H).

Examples 1.3-1.5 were prepared by a robot. The last two steps were carried out sequentially without isolation of the intermediates AR4, AR5 or AR6.

Example 1.3

| R | AR4 mg; mmol | CH$_2$Cl$_2$ ml | Ammonia in MeOH(7 N) ml | Prod. Form | Mass mg; Yield | MS-ESI |
|---|---|---|---|---|---|---|
| 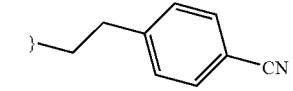 | nd*; 0.23 | 5 | 0.5 | oil | 18; 15% | 514 [M + H]$^+$ |

Chromato.-LC/MS H$_2$O/MeCN buffered with ammonium carbonate at pH 8.9 (0 to 100% H$_2$O)
$^1$H NMR spectrum (DMSO d$_6$): 1.26(s, 6H); 1.74(m, 4H); 2.3(s, 6H); 2.55-2.8(m, 8H); 3.4(m, 4H); 4.16(s, 2H); 7.02(s, 1H); 7.10(s, 2H); 7.36(d, 2H); 7.71 (d, 2H); 11.9(s br, 1H).

Example 1.4

| R | AR5 mg; mmol | CH$_2$Cl$_2$ ml | Ammonia in MeOH(7 N) ml | Prod. Form | Mass mg; Yield | MS-ESI |
|---|---|---|---|---|---|---|
| 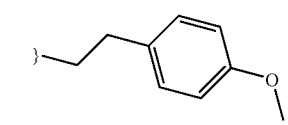 | nd*; 0.23 | 5 | 0.5 | oil | 15; 12% | 519 [M + H]$^+$ |

Chromato.-LC/MS H$_2$O/MeCN buffered with ammonium carbonate at pH 8.9 (0 to 100% H$_2$O)
$^1$H NMR spectrum (DMSO d$_6$): 1.27(s, 6H); 1.74(m, 4H); 2.30(s, 6H); 2.5-2.75(m, 8H); 3.5(m, 4H); 3.71(s, 3H); 4.16(s, 2H); 6.81(d, 2H); 7.02(s, 1H); 7.05 (d, 2H); 7.11(s, 2H); 11.9(s br, 1H).

Example 1.5

| R | AR6 mg; mmol | CH₂Cl₂ ml | Ammonia in MeOH(7 N) ml | Prod. Form | Mass mg; Yield | MS-ESI |
|---|---|---|---|---|---|---|
| ![structure] | nd*; 0.23 | 5 | 0.5 | oil | 23; 18% | 549 [M + H]⁺ |

*nd = not determined
Chromato.-LC/MS H₂O/MeCN buffered with ammonium carbonate at pH 8.9 (0 to 100% H₂O)
$^1$H NMR spectrum (DMSO $d_6$): 1.27(s, 6H); 1.77(m, 4H); 2.3(s, 6H); 2.55-2.7(m, 8H); 3.5(m, 4H); 3.68(s, 3H); 3.9(t, 2H); 4.16(s, 2H); 6.81(m, 4H); 7.01(s, 1H); 7.12(s, 2H); 11.9(s br, 1H).

Intermediates for Examples 1-1-1.5, AR2-AR6 Respectively

Starting materials AR2-AR6 were prepared as follows, the table showing the reaction conditions and characteristics for each example, corresponding to the description of AR1 given above:—

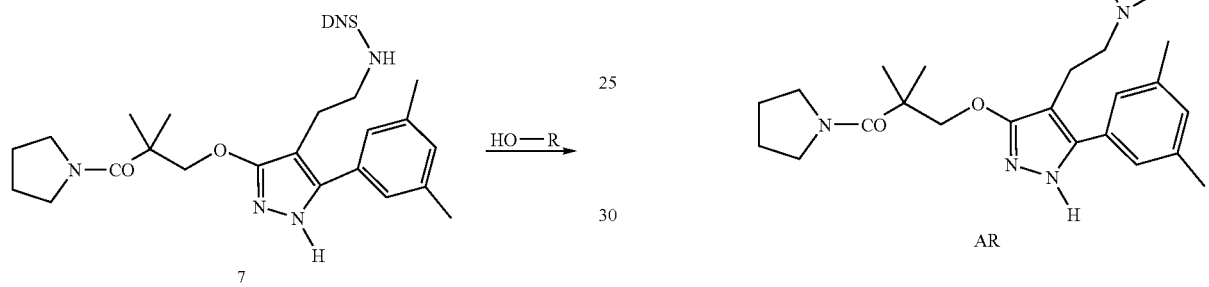

AR2

| R | 7 mg; mmol | Alcohol mg; mmol | PPh3 mg; mmol | THF ml | DEAD μl; mmol | Prod. Form | Mass mg; Yield % | MS-ESI |
|---|---|---|---|---|---|---|---|---|
| ![pyridyl] | 200; 0.32 | 55; 0.4 | 340; 1.3 | 10 | 205; 1.3 | Yellow solid | 216; 90% | 734 [M + H]⁺ |

Chromato.-EtOAc/CH₂Cl₂ (0 to 100% EtOAc)
$^1$H NMR spectrum (DMSO $d_6$): 1.22(s, 6H); 1.6-1.8(m, 4H); 1.84(m, 2H); 2.28(s, 6H); 2.55(m, 2H); 2.69(m, 2H); 3.3-3.5(m, 8H); 4.18(s, 2H); 7.00(s, 1H); 7.07(s, 2H); 7.19(d, 2H); 8.17(d, 1H); 8.43(d, 2H); 8.47(dd, 1H); 8.92(d, 1H); 11.9(s br, 1H).

AR3

| R | 7 mg; mmol | Alcohol mg; mmol | PPh3 mg; mmol | THF ml | DEAD μl; mmol | Prod. Form | Mass mg; Yield % | MS-ESI |
|---|---|---|---|---|---|---|---|---|
| ![pyridyl] | 200; 0.32 | 55; 0.4 | 340; 1.3 | 5 | 205; 1.3 | Yellow solid | 122; 51% | 734 [M + H]⁺ |

Chromato.-EtOAc/CH₂Cl₂ (0 to 100% EtOAc)
$^1$H NMR spectrum (DMSO $d_6$): 1.22(s, 6H); 1.5-1.9(m, 4H); 1.84(m, 2H); 2.28(s, 6H); 2.55(m, 2H); 2.68(m, 2H); 3.3-3.5(m, 8H); 4.18(s, 2H); 7.00(s, 1H); 7.07(s, 2H); 7.28(dd, 1H); 7.58(d, 1H); 8.17(d, 1H); 8.40(m, 2H); 8.47(dd, 1H); 8.92(d, 1H); 11.9(s br, 1H).

AR4

| R | 7 mg; mmol | Alcohol mg; mmol | PPh3 mg; mmol | THF ml | DTAD mg; mmol | Prod. Form | Mass mg; Yield % | MS-ESI |
|---|---|---|---|---|---|---|---|---|
| 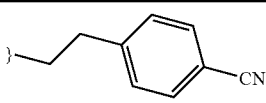 | 145; 0.23 | 38; 0.26 | 360; 1.38 | 1 | 205; 0.9 | nd* | nd* | nd* |

*not determined: Intermediate used directly in last step of robot run without isolation or purification.

AR5

| R | 7 mg; mmol | Alcohol mg; mmol | PPh3 mg; mmol | THF ml | DTAD mg; mmol | Prod. Form | Mass mg; Yield % | MS-ESI |
|---|---|---|---|---|---|---|---|---|
| 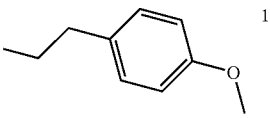 | 145; 0.23 | 40; 0.26 | 360; 1.38 | 1 | 205; 0.9 | nd* | nd* | nd* |

AR6

| R | 7 mg; mmol | Alcohol mg; mmol | PPh3 mg; mmol | THF ml | DTAD mg; mmol | Prod. Form | Mass mg; Yield % | MS-ESI |
|---|---|---|---|---|---|---|---|---|
| 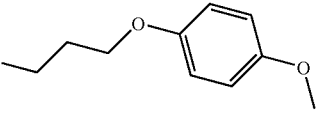 | 145; 0.23 | 47; 0.26 | 360; 1.38 | 1 | 205; 0.9 | nd* | nd* | nd* |

Example 2

2-[3-(2,2-dimethyl-3-oxo-3-{pyrrolidin-1-yl}propoxy)-5-(3,5-dimethylphenyl)-1H-pyrazol-4-yl]-N-(4-pyridin-4-ylbutyl)ethanamine

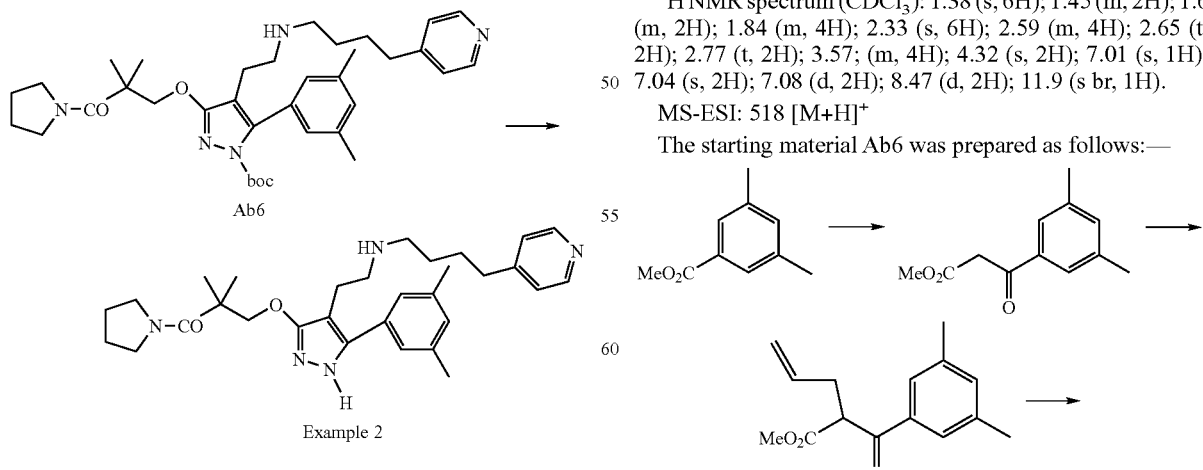

Dry, gaseous HCl was bubbled through a solution of Ab6 (180 mg; 0.29 mmol) in $CH_2Cl_2$ (30 ml) until no Ab6 remained. The mixture was treated with iced sat. aq. $NaHCO_3$, extracted with $CH_2Cl_2$ and the organic phase was washed with water, brine and dried over $MgSO_4$. The residue was purified by flash chromatography eluting with increasingly polar mixtures of ammonia in MeOH(7N)/$CH_2Cl_2$ (0 to 10% ammonia in MeOH) to give Example 2 (114 mg).

Yield: 76%

$^1$H NMR spectrum ($CDCl_3$): 1.38 (s, 6H); 1.45 (m, 2H); 1.6 (m, 2H); 1.84 (m, 4H); 2.33 (s, 6H); 2.59 (m, 4H); 2.65 (t, 2H); 2.77 (t, 2H); 3.57; (m, 4H); 4.32 (s, 2H); 7.01 (s, 1H); 7.04 (s, 2H); 7.08 (d, 2H); 8.47 (d, 2H); 11.9 (s br, 1H).

MS-ESI: 518 $[M+H]^+$

The starting material Ab6 was prepared as follows:—

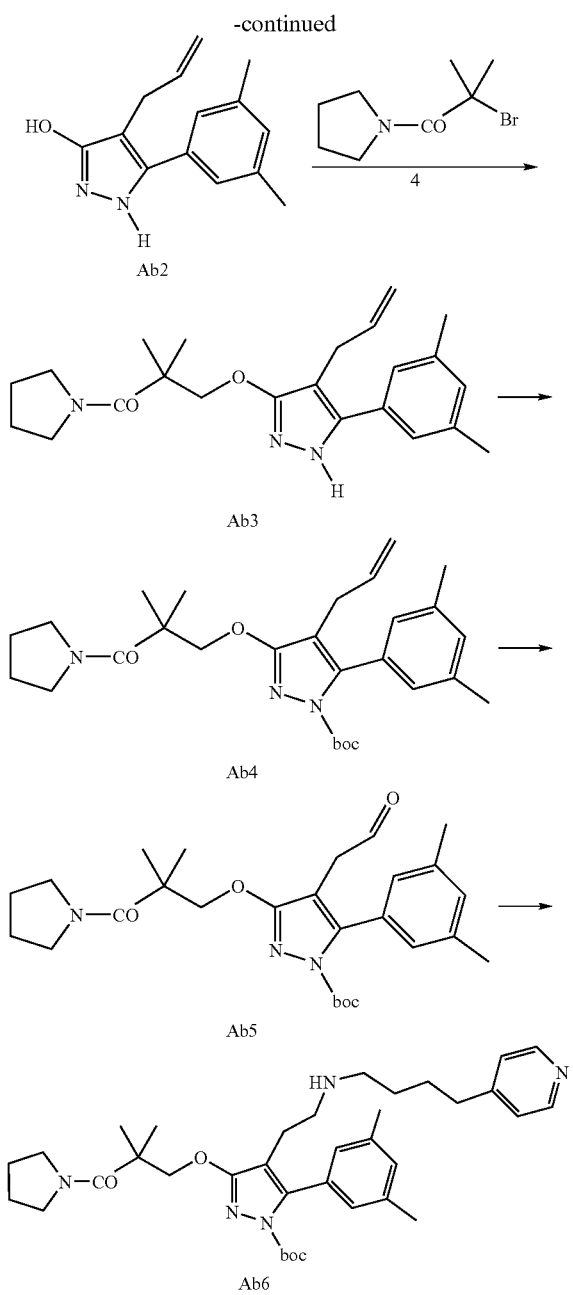

A solution of methyl 3,5-dimethylbenzoate (50 g; 300 mmol) in DME (80 ml) was added to a suspension of NaH (26.8 g; 60% in oil; 670 mmol) in DME (80 ml) under argon. The mixture was heated to reflux and a solution of methyl acetate (45 g; 610 mmol) in DME (40 ml) added dropwise. The mixture was heated for a further 4 h under reflux. The mixture was cooled and the excess of NaH destroyed by the dropwise addition of MeOH (40 ml). The mixture was poured into dilute HCl (2N), extracted with Et$_2$O and the organic phase was washed with water, brine and dried over MgSO$_4$. The residue was purified by flash chromatography eluting with Et$_2$O/hexanes (10% Et$_2$O) to give methyl 4-(3',5'-dimethylphenyl)acetoacetate as a yellow oil (31 g).

Yield: 50%

$^1$H NMR spectrum (CDCl$_3$): This compound exists as a 4/1 mixture of keto (k) and enol (e) forms: 2.36 (s, 6H)(e); 2.38 (s, 6H)(k); 3.76 (s, 3H)(k); 3.81 (s, 3H)(e); 4.03 (s, 2H)(k); 5.65 (s, 1H)(e); 7.11 (s, 1H)(e); 7.27 (s, 1H)(k); 7.4 (s, 2H)(e); 7.56 (s, 2H)(k); 12.48 (s, 1H)(e).

MS-ESI: 207 [M+H]$^+$

NaH (2.44 g; 60% in oil; 61 mmol) was added in small portions to a solution of methyl 4-(3',5'-dimethylphenyl)acetoacetate (9.66 g; 46.9 mmol) in DMF (50 ml) at 0° C. under argon. The mixture was stirred and allowed to warm to room temperature for 30 min. A solution of allyl bromide (4.05 ml; 46.9 mmol) in DMF (5 ml) was added dropwise and the mixture stirred for a further 2 h. The mixture was poured into H$_2$O, extracted with Et$_2$O and the organic phase was washed with water, brine and dried over MgSO$_4$. The residue was purified by flash chromatography eluting with Et$_2$O/hexanes (0 to 15% Et$_2$O) to give Ab1 as a pale yellow oil (8.3 g).

Yield: 72%

$^1$H NMR spectrum (CDCl$_3$): 2.39 (s, 6H); 2.76 (m, 2H); 3.70 (s, 3H); 4.43 (t, 1H); 5.08 (m, 1H); 5.15 (m, 1H); 5.82 (m, 1H); 7.24 (s, 1H); 7.60 (s, 2H).

MS-ESI: 247 [M+H]$^+$

A solution of Ab1 (3.4 g; 13 mmol) in EtOH (30 ml) was treated with hydrazine hydrate (3.9 ml; 78 mmol) and heated under reflux for 3 h. The EtOH was evaporated and the residue triturated with Et$_2$O. The precipitate was filtered, washed with H$_2$O and dried to give Ab2 as a white powder (2.8 g).

Yield: 95%

$^1$H NMR spectrum (CDCl$_3$+TFAD): 2.42 (s, 6H); 3.32 (d, 2H); 5.11 (d, 1H); 5.19 (d, 1H); 5.97 (m, 1H); 7.16 (s, 2H); 7.24 (s, 1H); 10.95 (s br 1H).

MS-ESI: 229 [M+H]$^+$

A mixture of Ab2 (2.1 g; 9.2 mmol) and 4 (2.15 g; 9.2 mmol) in DMA (30 ml) under argon was treated with K$_2$CO$_3$ (2.54 g; 18.4 mmol). The mixture was stirred and heated at 80° C. for 2 h. The mixture was poured into sat. aq. NaHCO$_3$, extracted with EtOAc and the organic phase was washed with water, brine and dried over MgSO$_4$. The residue was purified by flash chromatography eluting with increasingly polar mixtures of EtOAc/CH$_2$Cl$_2$ (50 to 100% EtOAc) to give Ab3 as a pale yellow solid (2.8 g).

Yield: 80%

$^1$H NMR spectrum (CDCl$_3$): 1.35 (s, 6H); 1.8 (m, 4H); 2.32 (s, 6H); 3.14 (m, 2H); 3.55 (m, 4H); 4.18 (s, 2H); 4.97 (m, 2H); 5.89 (m, 1H); 7.02 (s, 1H); 7.03 (s, 2H); 8.9 (br s, 1H).

MS-ESI: 382 [M+H]$^+$

A mixture of Ab3 (2.59 g; 6.8 mmol) and (BOC)$_2$O (7.4 g; 34 mmol) in CH$_3$CN (80 ml) was treated with Et$_3$N (1.9 ml; 13.6 mmol). The mixture was heated at 80° C. for 3 h. The solvent was evaporated, the mixture was poured into sat. aq. NaHCO$_3$, extracted with Et$_2$O and the organic phase was washed with water, brine and dried over MgSO$_4$. The residue was purified by flash chromatography eluting with increasingly polar mixtures of EtOAc/CH$_2$Cl$_2$ (0 to 25% EtOAc) to give Ab4 as a white solid (2.51 g).

Yield: 76%

$^1$H NMR spectrum (CDCl$_3$): 1.18 (s, 9H); 1.34 (s, 6H); 1.8 (m, 4H); 2.3 (s, 6H); 2.85 (m, 2H); 3.54 (m, 4H); 4.43 (s, 2H); 4.87 (m, 2H); 5.73 (m, 1H); 6.8 (s, 2H); 6.98 (s, 1H).

MS-ESI: 482 [M+H]$^+$

4-Methyl-morpholoine-N-oxide (1.6 ml; 60% solution in H$_2$O) was added to a solution of Ab4 (2.21 g; 4.6 mmol) in THF (100 ml) and H$_2$O (30 ml). The mixture was cooled to 0° C. and a solution of OsO$_4$ (92 mg; 0.36 mmol) in t-BuOH (1.8 ml) was added dropwise. The mixture was allowed to warm to room temperature for 6 h. The reaction was quenched by the addition of aq. Na$_2$S$_2$O$_5$ (1.75 g) in H$_2$O (50 ml). The THF was evaporated and the mixture extracted with EtOAc. The organic phase was washed with water, brine and dried over MgSO$_4$. The residue (2.21 g) was taken up in THF (100 ml) and H$_2$O (30 ml) and treated with NaIO$_4$. The mixture was stirred overnight. The THF was evaporated and the mixture extracted with EtOAc. The organic phase was washed with water, brine and dried over MgSO$_4$. The residue was purified by flash chromatography eluting with increasingly polar mixtures of EtOAc/CH$_2$Cl$_2$ (0 to 50% EtOAc) to give Ab5 as a buff solid (1.63 g).

Yield: 73%

$^1$H NMR spectrum (CDCl$_3$): 1.21 (s, 9H); 1.34 (s, 6H); 1.9 (m, 4H); 2.32 (s, 6H); 3.23 (d, 2H); 3.55 (m, 4H); 4.47 (s, 2H); 6.8 (s, 2H); 7.01 (s, 1H); 9.56 (d, 1H).

MS-ESI: 484 [M+H]$^+$

A solution of Ab5 (360 mg; 0.74 mmol) and 4-(4-aminobutyl)-pyridine (123 mg; 0.82 mmol) in MeOH (6 ml) was treated with NaBH$_3$CN (52 mg; 0.82 mmol). The mixture was cooled to 0° C. and acetic acid (45 µl; 0.82 mmol) was added. The mixture was allowed to warm to room temperature for 2 h and evaporated. The residue was treated with aq. K$_2$CO$_3$ (10%) and the mixture extracted with EtOAc. The organic phase was washed with water, brine and dried over MgSO$_4$. The residue was purified by flash chromatography eluting with EtOAc and then increasingly polar mixtures of MeOH/CH$_2$Cl$_2$ (0 to 5% MeOH) to give Ab6 as an oil (180 mg).

Yield: 40%

$^1$H NMR spectrum (CDCl$_3$): 1.20 (s, 9H); 1.37 (s, 6H); 1.61 (m, 2H); 1.87 (m, 6H); 2.31 (s, 6H); 2.48 (m, 2H); 2.62 (m, 4H); 2.76 (m, 2H); 3.57 (m, 4H); 4.45 (s, 2H); 6.8 (s, 2H); 7.0 (s, 1H); 7.08 (d, 2H); 8.47 (d, 2H).

MS-ESI: 618 [M+H]$^+$

Example 3

2-[3-(2,2-dimethyl-3-oxo-3-{azabicyclo[2.2.1]heptan-7-yl}propoxy)-5-(3,5-dimethylphenyl)-1H-pyrazol-4-yl]-N-(4-pyridin-4-ylbutyl)-ethanamine

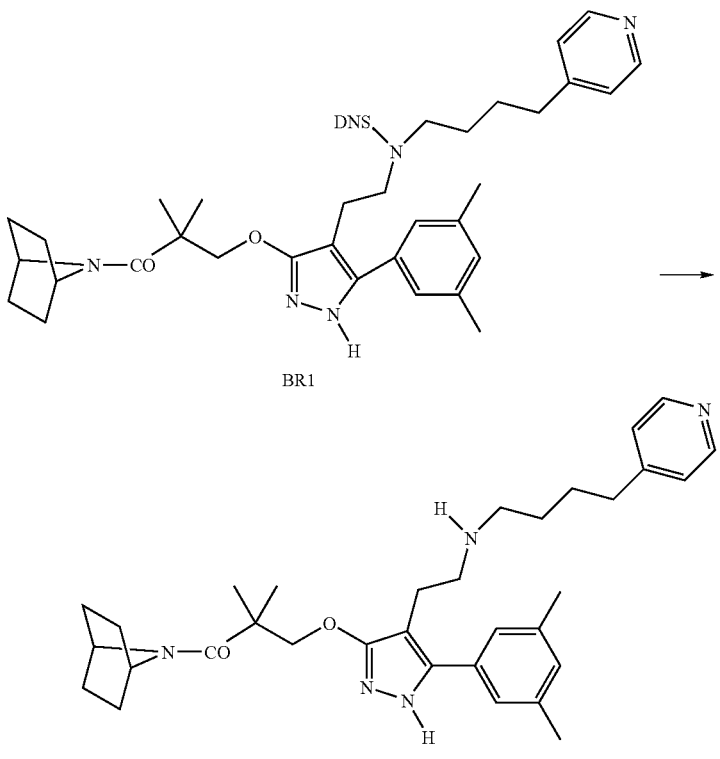

A solution of BR1 (322 mg; 0.41 mmol) in CH$_2$Cl$_2$ (5 ml) was treated dropwise with propylamine (340 µl; 4.1 mmol). The mixture was stirred at room temperature for 1 h and then purified directly by flash chromatography eluting with increasingly polar mixtures of MeOH/CH$_2$Cl$_2$ (0 to 10% MeOH) to give Example 3 as a white solid (219 mg).

Yield: 98%

$^1$H NMR spectrum (DMSO d$_6$): 1.25 (s, 6H); 1.43 (m, 6H); 1.61 (m, 6H); 2.3 (s, 6H); 2.59 (m, 4H); 2.65 (m, 2H); 2.75 (m, 2H); 4.16 (s, 2H); 4.57 (s, 2H); 7.02 (s, 1H); 7.11 (s, 2H); 7.21 (d, 2H); 8.44 (m, 2H); 11.8 (s br 1H).

MS-ESI: 544 [M+H]$^+$

Starting material BR1 was prepared as follows:—

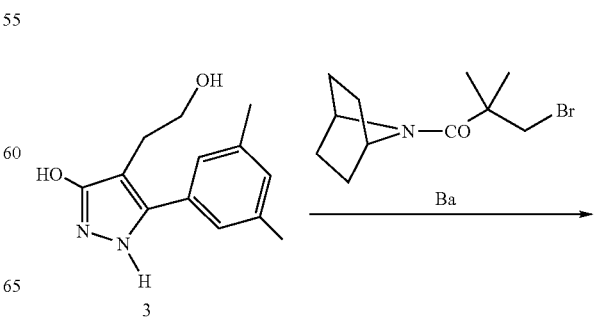

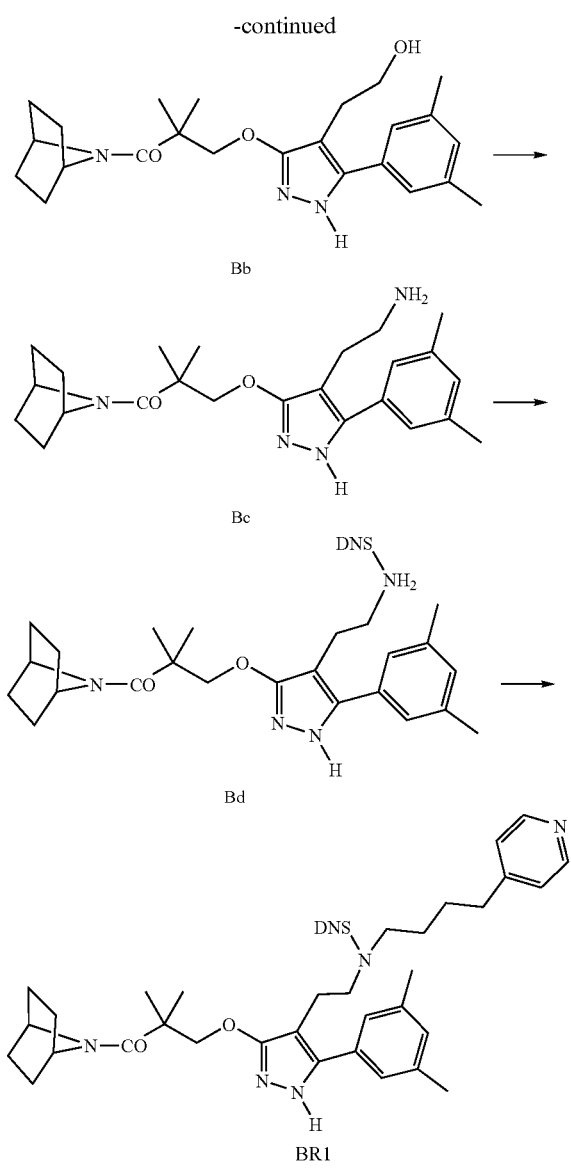

A mixture of 3 (4.64 g; 20 mmol) and Ba (5.72 g; 22 mmol) in DMA (50 ml) under argon was treated with K₂CO₃ (5.52 g; 40 mmol). The mixture was stirred and heated at 70° C. for 6 h. The mixture was poured into sat. aq. NaHCO₃, extracted with EtOAc and the organic phase was washed with water, brine and dried over MgSO₄. The residue was purified by flash chromatography eluting with increasingly polar mixtures of EtOAc/CH₂Cl₂ (0 to 50% EtOAc) to give the alcohol Bb as a pale yellow oil (7.58 g).

Yield: 92%

¹H NMR spectrum (DMSO d₆): 1.25 (s, 6H); 1.42 (m, 4H); 1.62 (m, 4H); 2.31 (s, 6H); 2.53 (m, 2H); 3.46 (m, 2H); 4.14 (s, 2H); 4.58 (s, 2H); 4.61 (t, 1H); 7.02 (s, 1H); 7.14 (s, 2H); 11.9 (br s, 1H).

MS-ESI: 412 [M+H]⁺

A mixture of Bb (3.29 g; 8 mmol), phthalimide (2.35 g; 16 mmol) and triphenylphosphine (12.5 g; 48 mmol) in THF (50 ml) was cooled to −20° C. under argon and treated dropwise with DEAD (7.6 ml; 48 mmol). The mixture was allowed to warm to 10° C. for 1 h when water was added and the TBH evaporated. The mixture was extracted with EtOAc and the organic phase was washed with water, brine and dried over MgSO₄.

Evaporation gave a crude solid which, without further purification, was immediately taken up in EtOH (200 ml) and treated with hydrazine hydrate (16 ml; 320 mmol). The mixture was stirred for 2 h and then the EtOH was partially evaporated. Addition of CH₂Cl₂ caused precipitation of phthalhydrazide which was filtered and rinsed with CH₂Cl₂. The filtrate was evaporated and the residue was purified by flash chromatography eluting with increasingly polar mixtures of EtOAc and then MeOH/CH₂Cl₂ (0 to 10% MeOH) to give Bc as a pale beige solid (2.53 g).

Yield: 77%

¹H NMR spectrum (DMSO d₆): 1.25 (s, 6H); 1.42 (m, 4H); 1.62 (m, 4H); 2.31 (s, 6H); 2.46 (m, 2H); 2.65 (t, 2H); 4.15 (s, 2H); 4.58 (m, 2H); 7.01 (s, 1H); 7.12 (s, 2H); 11.8 (s br 1H).

MS-ESI: 411 [M+H]⁺

A solution of Bc (1.43 g; 3.48 mmol) in CH₂Cl₂ (30 ml) was treated with diisopropylethylamine (910 μl; 5.22 mmol) and cooled to 0° C. A solution of 2,4-dinitrobenzenesulphonyl chloride (1.02 g; 3.84 mmol) in CH₂Cl₂ (10 ml) was added dropwise and the mixture was allowed to warm to room temperature for 30 min. The mixture was poured into sat. aq. NaHCO₃, extracted with EtOAc and the organic phase was washed with water, brine and dried over MgSO₄. The residue was purified by flash chromatography eluting with increasingly polar mixtures of EtOAc/CH₂Cl₂ (0 to 20% EtOAc) to give Bd as a cream solid (1.1 g).

Yield: 50%

¹H NMR spectrum (DMSO d₆): 1.22 (s, 6H); 1.41 (m, 4H); 1.59 (s, 4H); 2.3 (s, 6H); 2.57 (m, 2H); 3.11 (m, 2H); 4.12 (s, 2H); 4.55 (s, 2H); 7.0 (s, 1H); 7.03 (s, 2H); 8.17 (d, 1H); 8.59 (m, 2H); 8.83 (d, 1H); 11.8 (s br 1H).

MS-ESI: 641 [M+H]⁺

A mixture of Bd (300 mg; 0.43 mmol), 4-(4-hydroxybutyl)-pyridine (84 mg; 0.56 mmol) and triphenylphosphine (495 mg; 1.87 mmol) in THF (10 ml) at 0° C. under argon was treated dropwise with DEAD (300 μl; 1.87 mmol). The mixture was allowed to warm to room temperature for 30 min. when water was added. The THF was evaporated, the mixture extracted with EtOAc and the organic phase washed with water, brine and dried over MgSO₄.

The residue was purified by flash chromatography eluting with increasingly polar mixtures of EtOAc/CH₂Cl₂ (0 to 100% EtOAc) BR1 as a white solid (322 mg).

Yield: 89%

¹H NMR spectrum (DMSO d₆): 1.24 (s, 6H); 1.38 (m, 4H); 1.54 (m, 8H); 2.29 (s, 6H); 2.57 (m, 2H); 2.64 (m, 2H); 3.36 (m, 4H); 4.18 (s, 2H); 4.52 (m, 2H); 7.02 (s, 1H); 7.08 (s, 2H); 7.16 (d, 2H); 8.20 (d, 1H); 8.41 (d, 2H); 8.47 (dd, 1H); 8.91 (d, 1H); 11.8 (s br 1H).

MS-ESI: 774 [M+H]⁺

Starting material Ba was prepared as follows:—

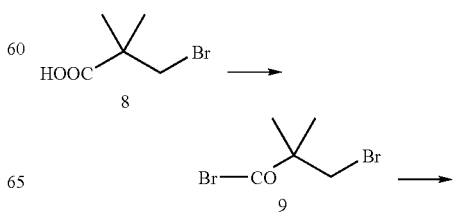

-continued

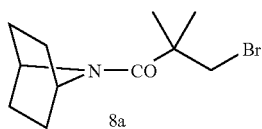

A mixture of 8 (14.48 g; 80 mmol) and oxalyl bromide (43.2 g; 200 mmol) containing one drop of DMF was heated at 50° C. for 2 h and then cooled. The excess of oxalyl bromide was evaporated and the residue azeotroped with toluene to give crude 9 which was taken up in CH$_2$Cl$_2$ (25 ml) and cooled to 0° C. Diisopropylethylamine (14 ml; 80 mmol) was added followed by 2.2.1-azabicycloheptane hydrochloride (5.34 g; 40 mmol). The mixture was allowed to warm to room temperature overnight and was diluted with CH$_2$Cl$_2$, washed with aq. HCl (2N), aq. NaOH (1N), water, brine and dried over MgSO$_4$. The residue was purified by flash chromatography eluting with CH$_2$Cl$_2$ to give Ba as a white solid (7.4 g).

Yield: 71%

$^1$H NMR spectrum (CDCl$_3$): 1.36 (s, 6H); 1.49 (m, 4H); 1.82 (m, 4H); 3.59 (s, 2H); 4.61 (s, 2H).

Examples 3.1-3.5

The following examples were prepared in a similar manner to Example 3,

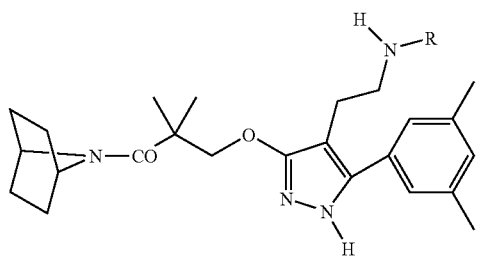

the table shows the R group relating to the above structure, the reaction conditions and characteristics for each example, corresponding to the description of the preparation of Example 3 given above:—

Example 3.1

| R | BR2 mg; mmol | CH$_2$Cl$_2$ ml | Propylamine µl; mmol | Mass mg; Yield | MS-ESI |
|---|---|---|---|---|---|
| ⁓⁓⁓-CH$_2$CH$_2$-(4-pyridyl) | 292; 0.39 | 5 | 320; 3.9 | 161; 80% | 516 [M + H]+ |

Chromato.-MeOH/CH$_2$Cl$_2$ (0 to 10% MeOH)

$^1$H NMR spectrum (DMSO d$_6$): 1.25(s, 6H); 1.41(m, 4H); 1.6(m, 4H); 2.29(s, 6H); 2.55(m, 2H); 2.71(m, 4H); 2.81(m, 2H); 4.15(s, 2H); 4.56(s, 2H); 7.02(s, 1H); 7.10(s, 2H); 7.2(d, 2H); 8.43(dd, 2H); 11.7(s br 1H).

Example 3.2

| R | BR3 mg; mmol | CH$_2$Cl$_2$ ml | Propylamine µl; mmol | Mass mg; Yield | MS-ESI |
|---|---|---|---|---|---|
| ⁓⁓⁓-CH$_2$CH$_2$-(1,2,4-triazol-1-yl) | 123; 0.17 | 3 | 140; 1.67 | 58; 68% | 506 [M + H]+ |

Chromato.-MeOH/CH$_2$Cl$_2$ (0 to 10% MeOH)

$^1$H NMR spectrum (DMSO d$_6$): 1.25(s, 6H); 1.42(m, 4H); 1.61(m, 4H); 2.3(s, 6H); 2.46(m, 2H); 2.64(m, 2H); 2.88(m, 2H); 4.15(s, 2H); 4.19(t, 2H); 4.57(s, 2H); 7.01(s, 1H); 7.09(s, 2H); 7.92(s, 1H); 8.42(s, 1H); 11.9(s br, 1H).

Example 3.3

| R | BR4 mg; mmol | CH₂Cl₂ ml | Propylamine µl; mmol | Mass mg; Yield | MS-ESI |
|---|---|---|---|---|---|
| 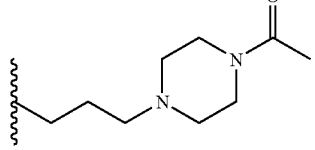 | 96; 0.12 | 3 | 140; 1.67 | 50; 72% | 579 [M + H]⁺ |

Chromato.-EtOAc and then MeOH/CH₂Cl₂ (0 to 10% MeOH)
¹H NMR spectrum (DMSO d₆): 1.26(s, 6H); 1.44(m, 4H); 1.61(m, 6H); 1.97(s, 3H) 2.25(s, 2H); 2.32(s, 6H); 2.4-2.85(m, 14H); 4.16(s, 2H); 4.58(s, 2H); 7.04(s, 1H); 7.11(s, 2H); 11.8(s, 1H).

Example 3.4

| R | BR5 mg; mmol | CH₂Cl₂ ml | Propylamine µl; mmol | Mass mg; Yield | MS-ESI |
|---|---|---|---|---|---|
| 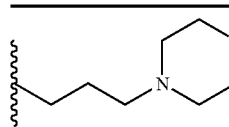 | 167; 0.22 | 3 | 180; 2.2 | 30; 25% | 538 [M + H]⁺ |

Chromato.-EtOAc and then MeOH/CH₂Cl₂ (0 to 10% MeOH)
¹H NMR spectrum (DMSO d₆): 1.26(s, 6H); 1.44(m, 4H); 1.57(m, 2H); 1.62(m, 4H); 2.27(m, 6H); 2.32(s, 6H); 2.5-2.85(m, 6H); 3.52(s, 4H); 4.16(s, 2H); 4.58(s, 2H); 7.03(s, 1H); 7.12(s, 2H); 11.8(s, 1H).

Example 3.5

| R | BR6 mg; mmol | CH₂Cl₂ ml | Propylamine µl; mmol | Mass mg; Yield | MS-ESI |
|---|---|---|---|---|---|
| 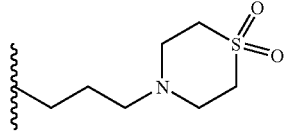 | 194; 0.24 | 3 | 195; 2.4 | 93; 66% | 586 [M + H]⁺ |

Chromato.-EtOAc and then MeOH/CH₂Cl₂ (0 to 10% MeOH)
¹H NMR spectrum (DMSO d₆): 1.26(s, 6H); 1.44(m, 4H); 1.55(m, 2H); 1.61(m, 4H); 2.32(s, 6H); 2.4-2.85(m, 8H); 2.82(s, 4H); 3.04(m, 4H); 4.16(s, 2H); 4.58(s, 2H); 7.03(s, 1H); 7.12(s, 2H); 11.8 (s, 1H).

Intermediates for Examples 3.1-3.5, BR2-BR6 Respectively

Starting materials BR2-6 were prepared as follows, the table showing the reaction conditions and characteristics for each example, corresponding to the description of Example 3 given above:—

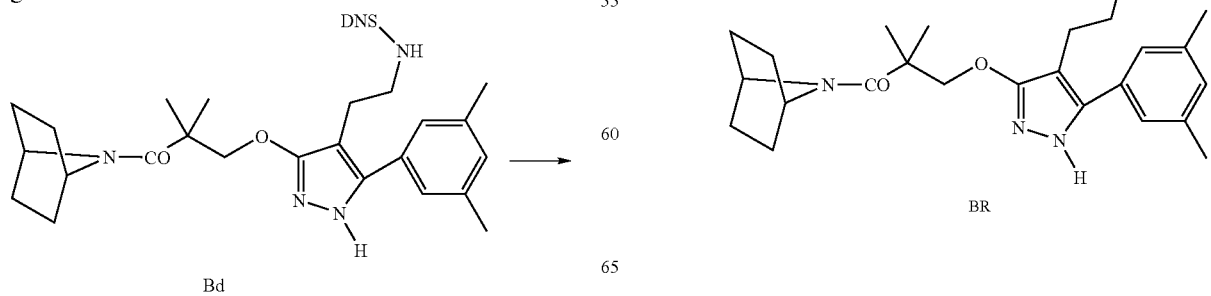

BR2

| R | Bd mg; mmol | Alcohol mg; mmol | PPh₃ mg; mmol | THF ml | DEAD μl; mmol | Mass mg; Yield | MS-ESI |
|---|---|---|---|---|---|---|---|
| 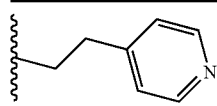 | 300; 0.47 | 70; 0.56 | 495; 1.87 | 10 | 290; 1.84 | 292; 83% | 746 [M + H]⁺ |

Chromato.-EtOAc/CH₂Cl₂ (0 to 100% EtOAc)

BR3

| R | Bd mg; mmol | Alcohol mg; mmol | PPh₃ mg; mmol | THF ml | DEAD μl; mmol | Mass mg; Yield | MS-ESI |
|---|---|---|---|---|---|---|---|
| 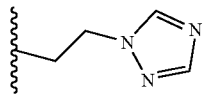 | 150; 0.23 | 32; 0.28 | 362; 1.38 | 5 | 145; 0.92 | 123; 72% | 736 [M + H]⁺ |

Chromato.-EtOAc/CH₂Cl₂ (0 to 100% EtOAc)

BR4

| R | Bd mg; mmol | Alcohol mg; mmol | PPh₃ mg; mmol | THF ml | DEAD μl; mmol | Mass mg; Yield | MS-ESI |
|---|---|---|---|---|---|---|---|
| 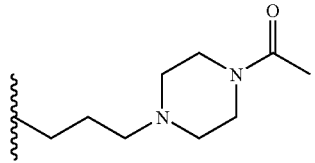 | 150; 0.23 | 53; 0.28 | 362; 1.38 | 5 | 200; 1.26 | 96; 51% | 809 [M + H]⁺ |

Chromato.-EtOAc/CH₂Cl₂ (0 to 100% EtOAc) and then MeOH/CH₂Cl₂ (0 to 10% MeOH)

BR5

| R | Bd mg; mmol | Alcohol mg; mmol | PPh₃ mg; mmol | THF ml | DEAD μl; mmol | Mass mg; Yield | MS-ESI |
|---|---|---|---|---|---|---|---|
| 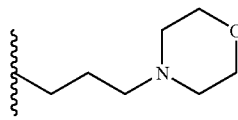 | 200; 0.31 | 54; 0.37 | 490; 1.86 | 5 | 270; 1.72 | 167; 70% | 768 [M + H]⁺ |

Chromato.-EtOAc and then MeOH/CH₂Cl₂ (0 to 10% MeOH)

BR6

| R | Bd mg; mmol | Alcohol mg; mmol | PPh₃ mg; mmol | THF ml | DEAD μl; mmol | Mass mg; Yield | MS-ESI |
|---|---|---|---|---|---|---|---|
| 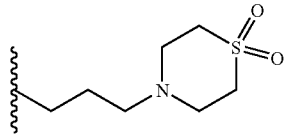 | 200; 0.31 | 72; 0.37 | 490; 1.86 | 5 | 270; 1.72 | 194; 77% | 816 [M + H]⁺ |

Chromato.-EtOAc and then MeOH/CH₂Cl₂ (0 to 10% MeOH).

Example 4

2-[3-(2,2-dimethyl-3-oxo-3-azabicyclo[2.2.1]heptan-7-yl)propoxy)-5-(3,5-dimethylphenyl)-1H-pyrazol-4-yl]-N-[2-(1,3-benzodioxol-5-yl)ethyl]-(2S)-propylamine

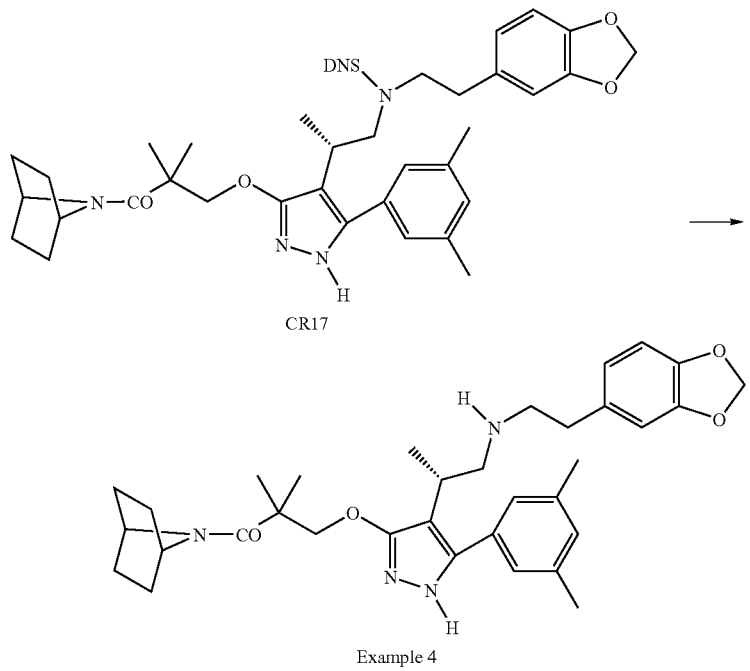

Example 4

A solution of partially purified* Cg17 (4.2 g; from 2.3 mmol of Cf) in CH$_2$Cl$_2$ (30 ml) under nitrogen was treated dropwise with n-propylamine (1.36 ml; 23 mmol) at room temperature. The mixture was stirred at room temperature for 2 h, the solvents evaporated and the residue purified directly by flash chromatography eluting with increasingly polar mixtures of EtOAc and then MeOH/CH$_2$Cl$_2$ (0 to 15% MeOH) to give Example 4 as a beige solid (768 mg). *Contains some Ph$_3$PO Yield: 59% for last two steps.

$^1$H NMR spectrum (DMSO d$_6$): 1.13 (d, 3H); 1.25 (s, 6H); 1.42 (m, 4H); 1.60 (m, 4H); 2.3 (s, 6H); 2.55-2.95 (m, 7H); 4.14 (s, 2H); 4.57 (s, 2H); 5.94 (s, 2H); 6.55 (d, 1H); 6.69 (s, 1H); 6.76 (d, 1H); 7.03 (s, 1H); 7.04 (s, 2H); 11.8 (s br 1H).

MS-ESI: 573 [M+H]$^+$

Starting materials Ce, Cf and CR17 were prepared as follows:—

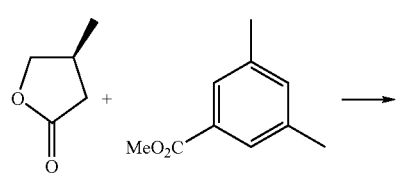

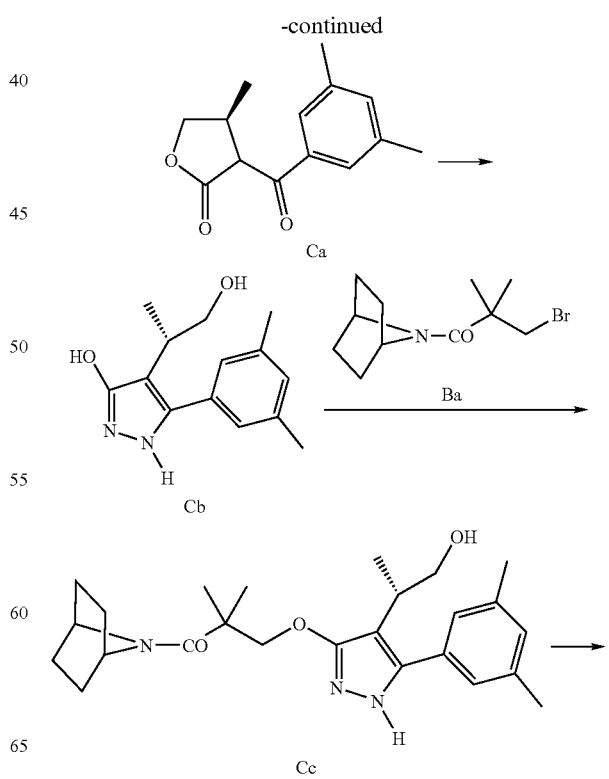

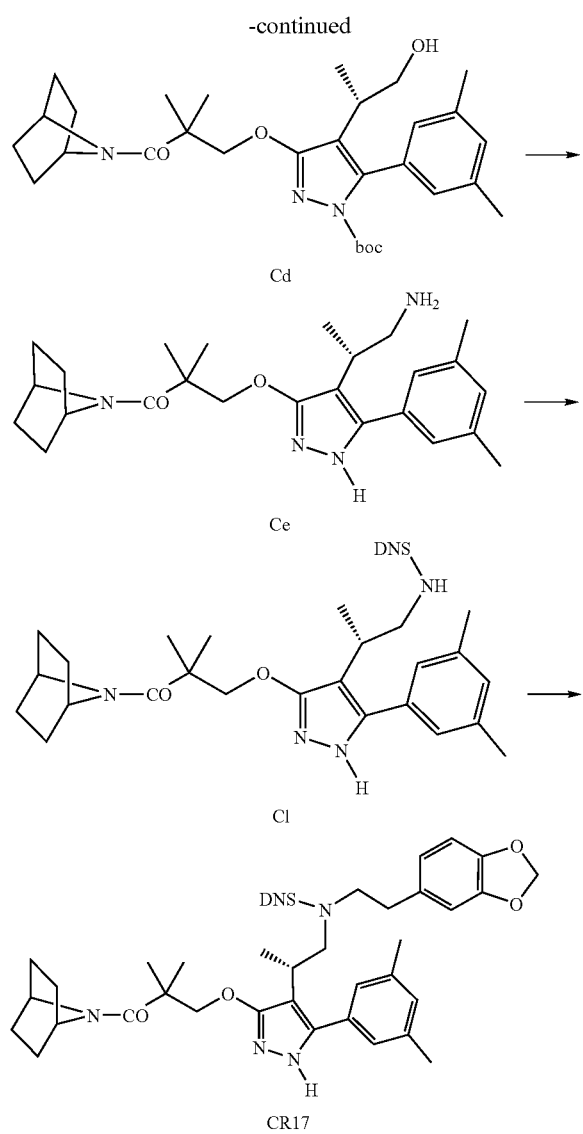

A solution of methyl 3,5-dimethylbenzoate (148 g; 0.9 mol) and 3S-methylbutyrolactone (90 g; 0.9 mol) in THF (2.4 l) under argon was cooled to 0° C. and treated dropwise rapidly with LHMDS (1.35 l; 1.35 mol; 1M in hexanes). The mixture was stirred for 2 h while the temperature was maintained below 10° C. The mixture was poured into dilute HCl (2N, 800 ml) at 0° C. Further dilute HCl (2N) was added until the pH reached 1.6. The THF was evaporated and the residual aqueous phase was extracted with EtOAc. The organic phase was washed with sat. aq. NaHCO₃, brine and dried over MgSO₄. The residue was purified by flash chromatography eluting with increasingly polar mixtures of EtOAc/hexanes (10 to 15% EtOAc) to give Ca as a colourless oil (127.7 g).

Yield: 61%.

$^1$H NMR spectrum (DMSO d₆): 1.09 (td, 3H); 2.36 (s, 6H); 3.05 (m, 1H); 3.93 (t, 1H); 4.50 (t, 1H); 4.78 (d, 1H); 7.36 (s, 1H); 7.67 (s, 2H).

MS-ESI: 233 [M+H]⁺

Compound Ca (127.5 g; 0.55 mol) was dissolved in EtOH (2.0 l) and hydrazine hydrate (27 ml; 0.55 mol) was added. The mixture was stirred overnight at room temperature. Dilute HCl (12N; 12 ml) was added and the mixture stirred for a further 1 h. The precipitate was filtered to give Cb as a white solid (63 g). Crystallisation from the mother liquors yielded further batches of Cb (29 g).

Yield: 68%

$^1$H NMR spectrum (DMSO d₆): 1.15 (d, 3H); 2.23 (s, 6H); 2.77 (m, 1H); 3.53 (d, 2H); 4.77 (br s, 1H); 7.01 (s, 1H); 7.04 (s, 2H); 9.5 (br s, 1H).

MS-ESI: 247 [M+H]⁺

A mixture of Cb (50 g; 0.20 mol) and Ba (60 g; 0.23 mol) in DMA (350 ml) under argon was treated with K₂CO₃ (56 g; 0.41 mol). The mixture was stirred and heated at 80° C. overnight. The mixture was cooled and poured into a stirred mixture of sat. aq. NAHCO₃/H₂O (1:2.5). The precipitate was filtered, washed abundantly with water and dried, to give the alcohol Cc as a pale beige solid. (84.5 g).

Yield: 99%

$^1$H NMR spectrum (DMSO d₆): 1.12 (d, 3H); 1.25 (s, 6H); 1.42 (m, 4H); 1.62 (m, 4H); 2.31 (s, 6H); 2.75 (m, 1H); 3.46 (m, 2H); 4.14 (m, 2H); 4.51 (br s, 1H); 4.58 (m, 2H); 7.03 (s, 1H); 7.06 (s, 2H); 11.9 (br s, 1H).

MS-ESI: 426 [M+H]⁺

A solution of Cc (42 g; 0.1 mol) in CH₂Cl₂ (800 ml) under argon was treated with acetonitrile (3 l) and DMAP (250 mg; cat.). The mixture was stirred and cooled to 0° C. and a solution of BOCOBOC (24 g; 0.11 mol) in acetonitrile (100 ML) was added slowly, dropwise. The mixture was allowed to warm to room temperature until no Cc remained (~1 day) and was poured into water (2 l) and stirred for 4 h. The organic solvents were evaporated. The mixture was extracted with CH₂Cl₂ and the organic phase was washed with water, brine and dried over MgSO₄. The residue was purified by flash chromatography eluting with increasingly polar mixtures of EtOAc/CH₂Cl₂ (20 to 50% EtOAc) to give Cd as a colourless foam (25.5 g).

Yield: 50%

$^1$H NMR spectrum (DMSO d₆): 1.02 (d, 3H); 1.16 (s, 9H); 1.270 (s, 6H); 1.44 (m, 4H); 1.62 (m, 4H); 2.29 (s, 6H); 2.33 (m, 1H); 3.38 (m, 2H); 4.23 (m, 2H); 4.54 (m, 1H); 4.59 (s, 2H); 6.89 (s, 1H); 7.05 (s, 2H).

MS-ESI: 526 [M+H]⁺

A solution of Cd (50.9 g; 97 mmol), phthalimide (17 g; 116 mmol) and triphenyl phosphine (38 g; 145 mmol) in THF (1 l) under argon was cooled to 0° C. and treated rapidly, portionwise with DTAD (33.3 g; 145 mmol). The mixture was allowed to warm to room temperature for 2 h 30 min. Water (500 ml) was added to the mixture and the organic solvent evaporated. The mixture was extracted with CH₂Cl₂ and the organic phase was washed with water, brine and dried over MgSO₄. The residue was purified by flash chromatography eluting with increasingly polar mixtures of EtOAc/CH₂Cl₂ (0 to 15% EtOAc) to give a cream foam (48.4 g) which was dissolved in EtOH (1.5 l). The mixture was treated with hydrazine hydrate (143 ml; 2.95 mol) at room temperature and was stirred for a further 26 h. The precipitate was filtered and the residue purified by flash chromatography eluting with increasingly polar mixtures of MeOH/CH₂Cl₂ (5 to 15% MeOH) to give Ce as a white solid (31.4 g).

Yield: 77%

$^1$H NMR spectrum (DMSO d₆): 1.12 (d, 3H); 1.25 (s, 6H); 1.42 (m, 4H); 1.61 (m, 4H), 2.31 (s, 6H); 2.63 (m, 2H); 2.72 (m, 1H); 4.15 (m, 2H); 4.57 (m, 2H); 7.02 (s, 1H); 7.06 (s, 2H); 8.9 (br s, 1H).

MS-ESI: 425 [M+H]⁺

A solution of Ce (1.5 g; 3.58 mmol) in THF (70 ml) was cooled to 0° C. under argon. DIEA (810 µl; 4.65 mmol) was added followed by a solution of DNOSCl (1.04 g; 3.9 mmol) in THF (20 ml). The mixture was allowed to warm to room temperature for 2 h and was treated with aq. HCl (1N). The mixture was extracted with CH₂Cl₂ and the organic phase was washed with water, brine and dried over MgSO₄. The residue was purified by flash chromatography eluting with increasingly polar mixtures of EtOAc/CH$_2$Cl$_2$ (0 to 100% EtOAc) to give Cf as a cream foam (2.07 g).

Yield: 88%

$^1$H NMR spectrum (DMSO d$_6$): 1.10 (d, 3H); 1.23 (s, 6H); 1.41 (m, 4H); 1.58 (m, 4H); 2.29 (s, 6H); 2.83 (m, 1H); 3.19 (m, 2H); 4.13 (m, 2H); 4.55 (m, 2H); 6.95 (s, 2H); 6.98 (s, 1H); 8.12 (d, 1H); 8.49 (br s, 1H); 8.52 (q, 1H); 8.79 (d, 1H).

MS-ESI: 655 [M+H]$^+$

A mixture of Cf (1.5 g; 2.3 mmol), the corresponding alcohol (575 mg; 3.45 mmol) and triphenylphosphine (3.67 g; 14 mmol) in THF (50 ml) at 0° C. under argon was treated with DTAD (2.12 g; 9.2 mmol). The mixture was allowed to warm to room temperature for 1 h when water was added. The mixture was extracted with CH$_2$Cl$_2$ and the organic phase was washed with water, brine and dried over MgSO$_4$. The residue was purified by flash chromatography eluting with increasingly polar mixtures of EtOAc/hexanes (0 to 50%) and then EtOAc/CH$_2$Cl$_2$ (0 to 100% EtOAc) to give CR17 as a beige solid (4.2 g).

This partially purified intermediate (containing some Ph$_3$PO) was used directly in the final step.

Example 4.1-4.54

The following examples were prepared using the same methodology as Example 4,

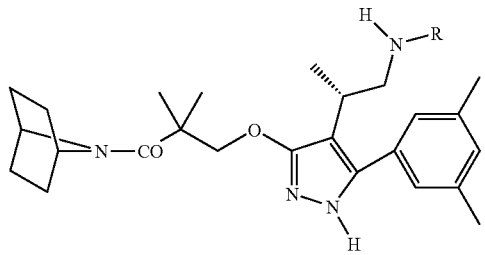

The table shows the R group relating to the above structure, the reaction conditions and characteristics of each example, corresponding to the description of the preparation of Example 4 given above:—

Example 4.1

| R | CR1 mg; mmol Cf | CH$_2$Cl$_2$ ml | Propylamine ml; mmol | Mass mg; Yield | MS-ESI |
|---|---|---|---|---|---|
| ⸺CH$_2$CH$_2$-(4-pyridyl) | 100; 0.13 | 5 | 0.11; 1.3 | 53; 78% | 530 [M + H]$^+$ |

Chromato.-EtOAc and then MeOH/CH$_2$Cl$_2$ (0 to 10% MeOH)
$^1$H NMR spectrum (DMSO d$_6$): 1.12(d, 3H); 1.25(s, 6H); 1.41(m, 4H); 1.60(m, 4H); 2.28(s, 6H); 2.6-2.9(m, 7H); 4.14(s, 2H); 4.57(s, 2H); 7.03(s, 3H); 7.12(d, 2H); 8.39(d, 2H); 11.8(s br 1H).

Example 4.2

| R | CR2 mg; mmol Cf | CH$_2$Cl$_2$ ml | Propylamine ml; mmol | Mass mg; Yield | MS-ESI |
|---|---|---|---|---|---|
| ⸺(CH$_2$)$_4$-(4-pyridyl) | 202; 0.25 | 3 | 0.21; 2.5 | 130; 91% | 558 [M + H]$^+$ |

Chromato.-EtOAc and then MeOH/CH$_2$Cl$_2$ (0 to 10% MeOH)
$^1$H NMR spectrum (DMSO d$_6$): 1.14(d, 3H); 1.25(s, 6H); 1.35(m, 2H); 1.42(m, 4H); 1.53(m, 2H); 1.61 (m, 4H); 2.29(s, 6H); 2.5-2.95(m, 7H); 4.15(s, 2H); 4.57(s, 2H); 7.03(s, 1H); 7.05(s, 2H); 7.17(d, 2H); 8.42(d, 2H) 11.8(s br 1H).

Example 4.3

| R | CR3 mg; mmol Cf | CH$_2$Cl$_2$ ml | Propylamine ml; mmol | Mass mg; Yield | MS-ESI |
|---|---|---|---|---|---|
| ⸺(CH$_2$)$_3$-(4-pyridyl) | 68; 0.09 | 3 | 0.08; 0.88 | 42; 87% | 544 [M + H]$^+$ |

Chromato.-EtOAc and then MeOH/CH$_2$Cl$_2$ (0 to 10% MeOH)
$^1$H NMR spectrum (DMSO d$_6$ -TFAd): 1.25(m, 9H); 1.43(m, 4H); 1.60(m, 4H); 1.97(m, 2H); 2.32(s, 6H); 2.8-3.15(m, 7H); 4.20(s, 2H); 4.55(s, 2H); 7.03(s, 2H); 7.07(s, 1H) 7.96(d, 2H); 8.89(d, 2H); 11.8(s br 1H).

Example 4.4

| R | CR4 mg; mmol Cf | CH₂Cl₂ ml | Propylamine ml; mmol | Mass mg; Yield | MS-ESI |
|---|---|---|---|---|---|
| }~~~~~⌬ (phenyl with pentyl chain) | 514; 0.19 | 3 | 0.165; 2 | 75; 68% | 557 [M + H]+ |

Chromato.-EtOAc
$^1$H NMR spectrum (DMSO d$_6$): 1.12(d, 3H); 1.25(s, 6H); 1.32(m, 2H); 1.42(m, 4H); 1.50;(m, 2H); 1.61 (m, 4H); 2.28(s, 6H); 2.35-2.85(m, 7H); 4.14(s, 2H); 4.57(s, 2H); 7.01(s, 1H); 7.06(s, 2H); 7.15(m, 3H); 7.24(m, 2H); 11.8(s br 1H).

Example 4.5

| R | CR5 mg; mmol Cf | CH₂Cl₂ ml | Propylamine ml; mmol | Mass mg; Yield | MS-ESI |
|---|---|---|---|---|---|
| }~~~~~⌬-OMe (4-methoxyphenyl with pentyl chain) | 1600; 0.5 | 30 | 0.58; 7 | 185; 63% | 587 [M + H]+ |

Chromato.-MeOH/CH₂Cl₂ (0 to 10% MeOH)
$^1$H NMR spectrum (DMSO d6): 1.13(d, 3H); 1.25(s, 6H); 1.35(m, 2H); 1.44(m, 4H); 1.47;(m, 2H); 1.61(m, 4H); 2.29(s, 6H); 2.4-2.9(m, 7H); 3.70(s, 3H); 4.15(s, 2H); 4.57(s, 2H); 6.81(d, 2H); 7.04(m, 5H); 11.8(s br 1H).

Example 4.6

| R | CR6 mg; mmol Cf | CH₂Cl₂ ml | Propylamine ml; mmol | Mass mg; Yield | MS-ESI |
|---|---|---|---|---|---|
| }~~~~~⌬-NO₂ (4-nitrophenyl with pentyl chain) | 230; 0.23 | 5 | 0.19; 2.3 | 103; 56% | xxx [M + H]⁺ |

Chromato.-EtOAc/CH₂Cl₂ (75 to 100% EtOAc) and then MeOH/CH₂Cl₂ (0 to 10% MeOH).
$^1$H NMR spectrum (DMSO d$_6$): 1.14(d, 3H); 1.25(s, 6H); 1.37(m, 2H); 1.42(m, 4H); 1.54(m, 2H); 1.59(m, 4H); 2.28(s, 6H); 2.55-2.95(m, 7H); 4.15(s, 2H); 4.57(s, 2H); 7.02(s, 1H); 7.05(s, 2H); 7.44(d, 2H); 8.14(d, 2H); 11.8(s br 1H)..

Example 4.7

| R | CR7 mg; mmol Cf | CH₂Cl₂ ml | Propylamine ml; mmol | Mass mg; Yield | MS-ESI |
|---|---|---|---|---|---|
| }~~~~-pyrimidinyl (pentyl chain to pyrimidine) | nd*; 0.23 | 5 | 0.19; 2.3 | 48; 37% | 559 [M + H]⁺ |

Chromato.-MeOH/CH₂Cl₂ (0 to 10% MeOH)
$^1$H NMR spectrum (DMSO d$_6$): 1.17(d, 3H); 1.25(s, 6H); 1.42(m, 4H); 1.48(m, 2H); 1.61(m, 4H); 1.71 (m, 2H); 2.3(s, 6H); 2.55-3.0(m, 7H); 4.17(s, 2H); 4.58(s, 2H); 7.04(m, 3H); 7.32(t, 1H); 8.71(d, 2H); 11.8(s br 1H).

Example 4.8

| R | CR8 mg; mmol Cf | CH$_2$Cl$_2$ ml | Propylamine ml; mmol | Mass mg; Yield | MS-ESI |
|---|---|---|---|---|---|
| 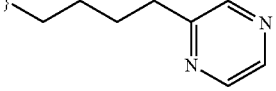 | nd*; 0.23 | 3 | 0.19; 2.3 | 71; 54% | 559 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 6H); 1.42(m, 6H); 1.63(m, 6H); 2.29(s, 6H); 2.55-2.9(m, 7H); 4.16(s, 2H); 4.57(s, 2H); 7.02(s, 1H); 7.05(s, 2H); 8.45(d, 1H); 8.52(m, 2H); 11.8(s br 1H)..

Example 4.9

| R | CR9 mg; mmol Cf | CH$_2$Cl$_2$ ml | Propylamine ml; mmol | Mass mg; Yield | MS-ESI |
|---|---|---|---|---|---|
| 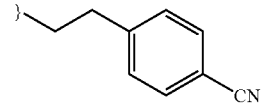 | nd*; 0.38 | 10 | 0.31; 3.8 | 94; 45% | 554 [M + H]$^+$ |

Chromato.-MeOH/CH$_2$Cl$_2$ (0 to 10% MeOH)
$^1$H NMR spectrum (DMSO d6): 1.12(d, 3H); 1.24(s, 6H); 1.41(m, 4H); 1.60(m, 4H); 2.29(s, 6H); 2.6-2.9(m, 7H); 4.15(s, 2H); 4.56(s, 2H); 7.02(s, 3H); 7.31(d, 2H); 7.68(d, 2H); 11.8(s br 1H).

Example 4.10

| R | CR10 mg; mmol Cf | CH$_2$Cl$_2$ ml | Propylamine ml; mmol | Mass mg; Yield | MS-ESI |
|---|---|---|---|---|---|
| 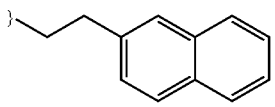 | nd*; 0.23 | 3 | 0.19; 2.3 | 50; 38% | 579 [M + H]$^+$ |

Chromato.-MeOH/CH$_2$Cl$_2$ (0 to 7% MeOH)
$^1$H NMR spectrum (DMSO d$_6$): 1.16(d, 3H); 1.25(s, 6H); 1.40(m, 4H); 1.59(m, 4H); 2.27(s, 6H); 2.55-2.95(m, 7H); 4.16(m, 2H); 4.56(s, 2H); 7.03(s, 1H); 7.04(s, 2H); 7.3(d, 1H); 7.46(m, 2H); 7.62(s, 1H); 7.8(m, 2H); 7.86(d, 1H); 11.8(s br 1H).

Example 4.11

| R | CR11 mg; mmol Cf | CH$_2$Cl$_2$ ml | Propylamine ml; mmol | Mass mg; Yield | MS-ESI |
|---|---|---|---|---|---|
| 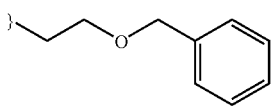 | nd*; 0.23 | 3 | 0.19; 2.3 | 88; 68% | 559 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 6H); 1.42(m, 4H); 1.61(m, 4H); 2.29(s, 6H); 2.6-2.95(m, 5H); 3.45(s, 2H); 4.16(s, 2H); 4.41(s, 2H); 4.56(s, 2H); 7.03(s, 1H); 7.06(s, 2H); 7.2-7.35(m, 6H); 11.8(s br 1H).

Example 4.12

| R | CR12 mg; mmol Cf | CH$_2$Cl$_2$ ml | Propylamine ml; mmol | Mass mg; Yield | MS-ESI |
|---|---|---|---|---|---|
| 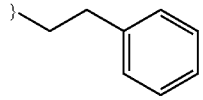 | nd*; 0.46 | 10 | 0.38; 4.6 | 152; 62% | 529 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 6H); 1.42(m, 4H); 1.60(m, 4H); 2.29(s, 6H); 2.45-2.95(m, 7H); 4.15(s, 2H); 4.57(s, 2H); 7.03(s, 1H); 7.04(s, 2H), 7.10(d, 2H); 7.16(t, 1H); 7.24(t, 2H); 11.8(s br 1H).

Example 4.13

| R | CR13 mg; mmol Cf | CH$_2$Cl$_2$ ml | Propylamine ml; mmol | Mass mg; Yield | MS-ESI |
|---|---|---|---|---|---|
| 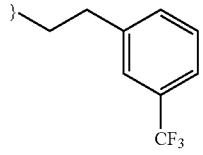 | nd*; 0.38 | 20 | 450; 7.6 | 154; 68% | 597 [M + H]$^+$ |

Chromato.-MeOH/CH$_2$Cl$_2$ (0 to 7% MeOH)
1H NMR spectrum (DMSO d6): 1.12(d, 3H); 1.25(s, 6H); 1.41(m, 4H); 1.6(m, 4H); 2.27(s, 6H); 2.6-2.9(m, 7H); 4.14(m, 2H); 4.56(s, 2H); 7.02(s, 1H); 7.03(s, 2H); 7.45(m, 4H); 11.8(s br 1H).

Example 4.14

| R | CR14 mg; mmol Cf | CH$_2$Cl$_2$ ml | Propylamine ml; mmol | Mass mg; Yield | MS-ESI |
|---|---|---|---|---|---|
| 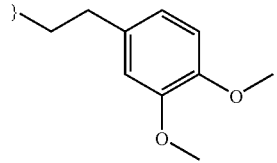 | nd*; 0.25 | 5 | 0.27; 4.5 | 105; 71% | 589 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.13(d, 3H); 1.25(s, 6H); 1.41(m, 4H); 1.60(m, 4H); 2.29(s, 6H); 2.6-2.9(m, 7H); 3.68(s, 3H); 3.70(s, 3H); 4.15(s, 2H); 4.57(s, 2H); 6.60(q, 1H); 6.72(d, 1H); 6.79(d, 1H); 7.03(s, 1H); 7.05(s, 1H); 11.8(s br 1H).

Example 4.15

| R | CR15 mg; mmol Cf | CH$_2$Cl$_2$ ml | Propylamine ml; mmol | Mass mg; Yield | MS-ESI |
|---|---|---|---|---|---|
| 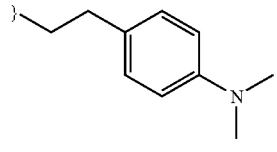 | nd*; 0.25 | 5 | 0.295; 5 | 32; 22% | 572 [M + H]$^+$ |

Chromato.-MeOH/CH$_2$Cl$_2$ (0 to 10% MeOH)
$^1$H NMR spectrum (DMSO d$_6$): 1.16(d, 3H); 1.25(s, 6H); 1.42(m, 4H); 1.60(m, 4H); 2.30(s, 6H); 2.6-2.9(m, 7H); 2.83(s, 6H); 4.16(s, 2H); 4.57(s, 2H); 6.61(d, 2H); 6.92(d, 2H); 7.04(s, 3H); 11.8(s br 1H).

Example 4.16

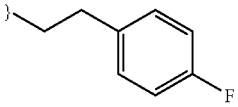

| R | CR16 mg; mmol Cf | CH$_2$Cl$_2$ ml | Propylamine ml; mmol | Mass mg; Yield | MS-ESI |
|---|---|---|---|---|---|
|  | nd*; 0.46 | 10 | 0.380; 4.6 | 149; 59% | 547 [M + H]$^+$ |

Chromato.-EtOAc/CH$_2$Cl$_2$ (0 to 100% EtOAc) and then MeOH/CH$_2$Cl$_2$ (0 to 10% MeOH)
$^1$H NMR spectrum (DMSO d$_6$): 1.13(d, 3H); 1.25(s, 6H); 1.41(m, 4H); 1.60(m, 4H); 2.29(s, 6H); 2.55-2.95(m, 7H); 4.15(s, 2H); 4.57(s, 2H); 7.03(m, 5H); 7.12(m, 2H); 11.8(s br 1H).

Example 4.17

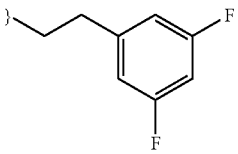

| R | CR18 mg; mmol Cf | CH$_2$Cl$_2$ ml | Propylamine ml; mmol | Mass mg; Yield | MS-ESI |
|---|---|---|---|---|---|
|  | nd*; 0.25 | 5 | 0.27; 4.5 | 61; 43% | 565 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (CDCl$_3$): 1.21(d, 3H); 1.35(d, 6H); 1.44(m, 4H); 1.75(m, 4H); 2.33(s, 6H); 2.6-3.1(m, 7H); 4.26(m, 2H); 4.63 (s, 2H); 6.61(m, 3H); 7.01(s, 3H); 9.1(s br, 1H).

Example 4.18

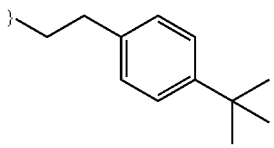

| R | CR19 mg; mmol Cf | CH$_2$Cl$_2$ ml | Propylamine ml; mmol | Mass mg; Yield | MS-ESI |
|---|---|---|---|---|---|
|  | nd*; 0.25 | 5 | 0.27; 4.5 | 53; 36% | 585 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 15H); 1.41(m, 4H); 1.6(m, 4H); 2.29(s, 6H); 2.55-2.95(m, 7H); 4.15(s, 2H); 4.56 (s, 2H); 7.02(d, 2H); 7.03(s, 1H); 7.04(s, 2H); 7.25(d, 2H); 11.8(s br 1H).

Example 4.19

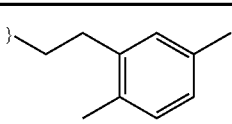

| R | CR20 mg; mmol Cf | CH$_2$Cl$_2$ ml | Propylamine ml; mmol | Mass mg; Yield | MS-ESI |
|---|---|---|---|---|---|
|  | nd*; 0.25 | 5 | 0.27; 4.5 | 40; 29% | 557 [M + H]$^+$ |

Chromato.-MeOH/CH$_2$Cl$_2$ (0 to 10% MeOH)
$^1$H NMR spectrum (DMSO d$_6$): 1.18(d, 3H); 1.25(s, 6H); 1.42(m, 4H); 1.6(m, 4H); 2.16(s, 3H); 2.20(s, 3H); 2.30(s, 6H); 2.5-2.95(m, 7H); 4.17(s, 2H); 4.56(s, 2H); 6.84(s, 1H); 6.88(d, 1H); 6.99(s, 1H); 7.05(s, 3H); 11.8(s br 1H).

Example 4.20

| R | CR21 mg; mmol Cf | CH$_2$Cl$_2$ ml | Propylamine ml; mmol | Mass mg; Yield | MS-ESI |
|---|---|---|---|---|---|
| 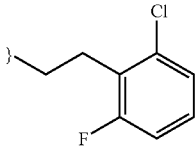 | nd*; 0.25 | 5 | 0.27; 4.5 | 49; 34% | 581 [M + H]$^+$ |

Chromato.-MeOH/CH$_2$Cl$_2$ (0 to 10% MeOH)
$^1$H NMR spectrum (DMSO d$_6$): 1.13(d, 3H); 1.25(s, 6H); 1.42(m, 4H); 1.61(m, 4H); 2.29(s, 6H); 2.55-2.9(m, 7H); 4.15(s, 2H); 4.57(s, 2H); 7.02(s, 1H); 7.04(s, 2H); 7.15(m, 1H); 7.27(m, 2H); 11.8(s br 1H).

Example 4.21

| R | CR22 mg; mmol Cf | CH$_2$Cl$_2$ ml | Propylamine ml; mmol | Mass mg; Yield | MS-ESI |
|---|---|---|---|---|---|
| 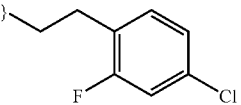 | nd*; 0.25 | 5 | 0.27; 4.5 | 64; 44% | 581 [M + H]$^+$ |

Chromato.-MeOH/CH$_2$Cl$_2$ (0 to 10% MeOH)
$^1$H NMR spectrum (DMSO d$_6$): 1.13(d, 3H); 1.25(s, 6H); 1.42(m, 4H); 1.6(m, 4H); 2.29(s, 6H); 2.55-2.95(m, 7H); 4.15(s, 2H); 4.56(s, 2H); 7.02(s, 1H); 7.04(s, 2H); 7.10(m, 1H); 7.26(m, 1H); 7.35(m, 1H); 11.8(s br 1H).

Example 4.22

| R | CR23 mg; mmol Cf | CH$_2$Cl$_2$ ml | Propylamine ml; mmol | Mass mg; Yield | MS-ESI |
|---|---|---|---|---|---|
| 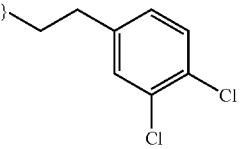 | nd*; 0.25 | 5 | 0.27; 4.5 | 50; 34% | 597 [M + H]$^+$ |

Chromato.-MeOH/CH$_2$Cl$_2$ (0 to 10% MeOH)
$^1$H NMR spectrum (DMSO d$_6$): 1.13(d, 3H); 1.25(s, 6H); 1.42(m, 4H); 1.6(m, 4H); 2.28(s, 6H); 2.55-2.95(m, 7H); 4.16(m, 2H); 4.56(s, 2H); 7.03(s, 3H); 7.11(d, 1H); 7.41(s, 1H) 7.48(d, 1H); 11.8(s br 1H).

Example 4.23

| R | CR24 mg; mmol Cf | CH$_2$Cl$_2$ ml | Propylamine ml; mmol | Mass mg; Yield | MS-ESI |
|---|---|---|---|---|---|
| 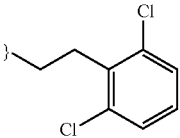 | nd*; 0.25 | 5 | 0.27; 4.5 | 40; 27% | 597 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 6H); 1.41(m, 4H); 1.61(m, 4H); 2.29(s, 6H); 2.55-2.95(m, 7H); 4.15(s, 2H); 4.57(s, 2H); 7.02(s, 1H); 7.05(s, 2H); 7.25(t, 1H); 7.4(d, 2H); 11.8(s br 1H).

Example 4.24

| R | CR25 mg; mmol Cf | CH$_2$Cl$_2$ ml | Propylamine ml; mmol | Mass mg; Yield | MS-ESI |
|---|---|---|---|---|---|
| (pyrrolidine fused dioxole with acetyl group) | nd*; 0.23 | 5 | 540; 9.2 | 50; 37% | 580 [M + H]$^+$ |

Chromato.-MeOH/CH$_2$Cl$_2$ (0 to 10% MeOH)

$^1$H NMR spectrum (DMSO d$_6$): 1.13(d, 3H); 1.25(s, 6H); 1.42(m, 4H); 1.61(m, 4H); 2.31(s, 6H); 2.55-2.95(m, 3H); 3.1-3.75(m, 4H); 3.67(m, 2H); 4.15(s, 2H); 4.57(s, 2H); 4.62(m, 1H); 4.68(m, 1H); 4.76(s, 1H); 4.93(s, 1H); 7.03(s, 1H); 7.06(s, 1H); 11.8(s br 1H).

Example 4.25

| R | CR26 mg; mmol Cf | CH$_2$Cl$_2$ ml | Propylamine ml; mmol | Mass mg; Yield | MS-ESI |
|---|---|---|---|---|---|
| (pyrrolidine fused dioxole with propyl linker) | nd*; 0.23 | 5 | 0.810; 13.2 | 68; 52% | 566 [M + H]$^+$ |

Chromato.-MeOH/CH$_2$Cl$_2$ (0 to 10% MeOH)

$^1$H NMR spectrum (DMSO d$_6$): 1.13(d, 3H); 1.26(s, 6H); 1.42(m, 4H); 1.62(m, 4H); 2.03(m, 2H); 2.31(s, 6H); 2.33(m, 3H); 2.55-2.95(m, 6H); 4.14(s, 2H); 4.49(m, 2); 4.58(s, 2H); 4.71(s, 1H); 4.8(s, 1H); 7.03(s, 1H); 7.06(s, 2H); 11.8(s br 1H).

Example 4.26

| R | CR27 mg; mmol Cf | CH$_2$Cl$_2$ ml | Propylamine ml; mmol | Mass mg; Yield | MS-ESI |
|---|---|---|---|---|---|
| (3-fluorophenethyl) | nd*; 0.26 | 5 | 0.27; 3.3 | 55; 38% | 547 [M + H]$^+$ |

Chromato.-MeOH/CH$_2$Cl$_2$ (0 to 10% MeOH)

$^1$H NMR spectrum (DMSO d$_6$): 1.14(d, 3H); 1.25(s, 6H); 1.42(m, 4H); 1.6(m, 4H); 2.29(s, 6H); 2.55-2.95(m, 7H); 4.15(m, 2H); 4.57(s, 2H); 6.97(m, 3H); 7.03(s, 3H); 7.27(m, 1H); 11.8(s br 1H).

Example 4.27

| R | CR28 mg; mmol Cf | CH$_2$Cl$_2$ ml | Propylamine ml; mmol | Mass mg; Yield | MS-ESI |
|---|---|---|---|---|---|
| (3-chlorophenethyl) | nd*; 0.26 | 5 | 0.27; 3.3 | 40; 27% | 563 [M + H]$^+$ |

Chromato.-MeOH/CH$_2$Cl$_2$ (0 to 10% MeOH)

$^1$H NMR spectrum (DMSO d$_6$): 1.14(d, 3H); 1.25(s, 6H); 1.42(m, 4H); 1.6(m, 4H); 2.29(s, 6H); 2.55-2.95(m, 7H); 4.15(m, 2H); 4.57(s, 2H); 7.03(s, 3H); 7.09(m, 1H); 7.25(m, 3H); 11.8(s br 1H).

Example 4.28

| R | CR29 mg; mmol Cf | CH$_2$Cl$_2$ ml | Propyl-amine ml; mmol | Mass mg; Yield | MS-ESI |
|---|---|---|---|---|---|
| 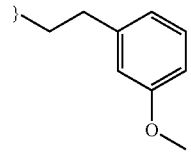 | nd*; 0.26 | 5 | 0.27; 3.3 | 47; 32% | 559 [M + H]$^+$ |

Chromato.-MeOH/CH$_2$Cl$_2$ (0 to 10% MeOH)
$^1$H NMR spectrum (DMSO d$_6$): 1.16(d, 3H); 1.25(s, 6H); 1.42(m, 4H); 1.6 (m, 4H); 2.3(s, 6H); 2.55-2.95(m, 7H); 3.71(s, 3H); 4.16(s, 2H); 4.56(s, 2H); 6.7(m, 3H); 7.04(s, 3H); 7.16(m, 1H); 11.8(s br 1H).

Example 4.29

| R | CR30 mg; mmol Cf | CH$_2$Cl$_2$ ml | Propyl-amine mmol | Mass mg; Yield | MS-ESI |
|---|---|---|---|---|---|
| 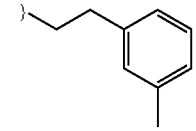 | nd*; 0.26 | 5 | 0.27; 3.3 | 70; 49% | 543 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(s, 6H); 1.42(m, 4H); 1.6 (m, 4H); 2.24(s, 3H); 2.3(s, 6H); 2.55-2.95(m, 7H); 4.16(s, 2H); 4.57(s, 2H); 6.90(m, 2H); 6.98(d, 1H); 7.04(s, 3H); 7.12(t, 1H); 11.8(s br 1H).

Example 4.30

| R | CR31 mg; mmol Cf | CH$_2$Cl$_2$ ml | Propylamine ml; mmol | Mass mg; Yield | MS-ESI |
|---|---|---|---|---|---|
| 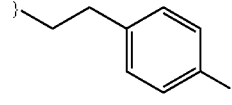 | nd*; 0.26 | 5 | 0.27; 3.3 | 64; 43% | 563 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(m, 6H); 1.42(m, 4H); 1.6(m, 4H); 2.29(s, 6H); 2.5-2.9(m, 7H); 4.16(s, 2H); 4.56(m, 2H); 7.03(s, 3H); 7.14(d, 2H); 7.29(d, 2H); 11.8(s br 1H).

Example 4.31

| R | CR32 mg; mmol Cf | CH$_2$Cl$_2$ ml | Propylamine ml; mmol | Mass mg; Yield | MS-ESI |
|---|---|---|---|---|---|
| 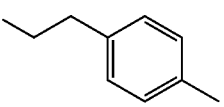 | nd*; 0.26 | 5 | 0.27; 3.3 | 143; 100% | 543 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(m, 6H); 1.42(m, 4H); 1.6(m, 4H); 2.24(s, 3H); 2.29(s, 6H); 2.5-2.95(m, 7H); 4.15(s, 2H); 4.56(m, 2H); 6.98(d, 2H); 7.04(m, 5H); 11.8(s br 1H).

Example 4.32

| R | CR33 mg; mmol Cf | CH$_2$Cl$_2$ ml | Propylamine ml; mmol | Mass mg; Yield | MS-ESI |
|---|---|---|---|---|---|
| 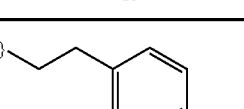 | nd*; 0.26 | 5 | 0.27; 3.3 | 133; 90% | 559 [M + H]$^+$ |

Chromato.-MeOH/CH$_2$Cl$_2$ (0 to 10% MeOH)
$^1$H NMR spectrum (DMSO d$_6$): 1.13(d, 3H); 1.25(m, 6H); 1.42(m, 4H); 1.6(m, 4H); 2.29(s, 6H); 2.5-2.95(m, 7H); 3.70(s, 3H); 4.15(s, 2H); 4.56(m, 2H); 6.79(d, 2H); 7.01;(d, 2H); 7.04(s, 3H); 11.8(s br 1H).

Example 4.33

| R | CR34 mg; mmol Cf | CH$_2$Cl$_2$ ml | Propyl-amine ml; mmol | Mass mg; Yield | MS-ESI |
|---|---|---|---|---|---|
| 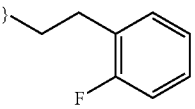 | nd*; 0.26 | 5 | 0.27; 3.3 | 51; 35% | 547 [M + H]$^+$ |

Chromato.-MeOH/CH$_2$Cl$_2$ (0 to 10% MeOH)
$^1$H NMR spectrum (DMSO d$_6$): 1.14(d, 3H); 1.25(m, 6H); 1.42(m, 4H); 1.6 (m, 4H); 2.29(s, 6H); 2.5-2.95(m, 7H); 3.70(s, 3H); 4.16(m, 2H); 4.56(s, 2H); 7.04(s, 3H); 7.09(m, 2H); 7.21;(m, 2H); 11.8(s br 1H).

Example 4.34

Example 4.34 was prepared by a different methodology (opening of epoxide by Ce): see below.

Example 4.35

| R | CR36 mg; mmol Cf | CH$_2$Cl$_2$ ml | Propylamine ml; mmol | Mass mg; Yield | MS-ESI |
|---|---|---|---|---|---|
| 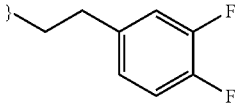 | nd*; 0.25 | 5 | 0.27; 4.5 | 78; 55% | 565 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.13(d, 3H); 1.25(s, 6H); 1.42(m, 4H); 1.61(m, 4H); 2.29(s, 6H); 2.55-2.95(m, 7H); 4.14(m, 2H); 4.57(s, 2H); 6.94(m, 1H); 7.03(s, 3H); 7.15(m, 1H); 7.26(m, 1H); 11.8(s br 1H).

Example 4.36

| R | CR37 mg; mmol Cf | CH$_2$Cl$_2$ ml | Propylamine ml; mmol | Mass mg; Yield | MS-ESI |
|---|---|---|---|---|---|
| 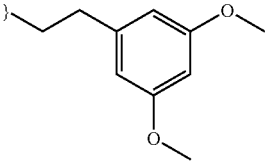 | nd*; 0.25 | 5 | 0.27; 4.5 | 32; 22% | 589 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.14(d, 3H); 1.25(s, 6H); 1.41(m, 4H); 1.60(m, 4H); 2.29(s, 6H); 2.55-2.95(m, 7H); 3.68(s, 6H); 4.15(m, 2H); 4.57(s, 2H); 6.3(m, 3H); 7.03(s, 1H); 7.04(s, 2H); 11.8(s br 1H).

Example 4.37

| R | CR38 mg; mmol Cf | CH$_2$Cl$_2$ ml | Propylamine ml; mmol | Mass mg; Yield | MS-ESI |
|---|---|---|---|---|---|
| 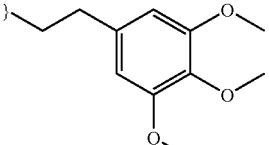 | nd*; 0.25 | 5 | 0.27; 4.5 | 102; 66% | 619 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.14(d, 3H); 1.25(s, 6H); 1.41(m, 4H); 1.60(m, 4H); 2.29(s, 6H); 2.55-2.95(m, 7H); 3.60(s, 3H); 3.69(s, 6H); 4.14(s, 2H); 4.56(s, 2H); 6.42(s, 2H); 7.02(s, 1H); 7.05(s, 2H); 11.8(s br 1H).

Example 4.38

| R | CR39 mg; mmol Cf | CH$_2$Cl$_2$ ml | Propylamine ml; mmol | Mass mg; Yield | MS-ESI |
|---|---|---|---|---|---|
| 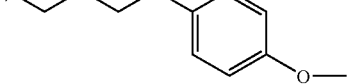 | nd*; 0.25 | 5 | 0.27; 4.5 | 91; 62% | 589 [M + H]$^+$ |

Chromato.-EtOAc/CH2Cl2 (50 to 100% EtOAc) and then MeOH/CH2Cl2 (0 to 10% MeOH)
$^1$H NMR spectrum (DMSO d6): 1.15(d, 3H); 1.25(s, 6H); 1.42(m, 4H); 1.61(m, 4H); 1.78(m, 2H); 2.29(s, 6H); 2.55-2.95(m, 5H); 3.68(s, 3H); 3.88(t, 2H); 4.15(s, 2H); 4.56(s, 2H); 6.80(m, 4H); 7.02(s, 1H); 7.06(s, 2H); 11.8(s br 1H).

Example 4.39

| R | CR40 mg; mmol Cf | CH$_2$Cl$_2$ ml | Propylamine ml; mmol | Mass mg; Yield | MS-ESI |
|---|---|---|---|---|---|
| 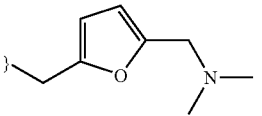 | nd*; 0.25 | 5 | 0.27; 4.5 | 85; 61% | 562 [M + H]$^+$ |

Chromato.-EtOAc/CH$_2$Cl$_2$ (50 to 100% EtOAc) and then MeOH/CH$_2$Cl$_2$ (0 to 10% MeOH).
$^1$H NMR spectrum (DMSO d$_6$): 1.13(d, 3H); 1.25(s, 6H); 1.42(m, 4H); 1.61(m, 4H); 2.08(s, 6H); 2.30 (s, 6H); 2.55-2.95(m, 3H); 3.35(s, 2H); 3.53(s, 2H); 4.14(m, 2H); 4.57(s, 2H); 6.01(d, 1H); 6.10(d, 1H); 7.03(s, 1H); 7.05(s, 2H), 11.8(s br 1H).

Example 4.40

| R | CR41 mg; mmol Cf | CH$_2$Cl$_2$ ml | Propylamine ml; mmol | Mass mg; Yield | MS-ESI |
|---|---|---|---|---|---|
| 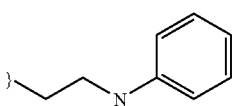 | nd*; 0.25 | 5 | 0.27; 4.5 | 40; 29% | 544 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.14(d, 3H); 1.25(s, 6H); 1.41(m, 4H); 1.61(m, 4H); 2.29(s, 6H); 2.55-2.95(m, 5H); 3.01;(m, 2H); 4.14(s, 2H); 4.56(s, 2H); 5.37(s, 1H); 6.50(m, 3H); 7.04(m, 5H); 11.8(s br 1H).

Example 4.41

| R | CR42 mg; mmol Cf | CH$_2$Cl$_2$ ml | Propylamine ml; mmol | Mass mg; Yield | MS-ESI |
|---|---|---|---|---|---|
| 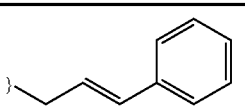 | nd*; 0.25 | 5 | 0.27; 4.5 | 87; 64% | 541 [M + H]$^+$ |

Chromato.-EtOAc/CH$_2$Cl$_2$ (50 to 100% EtOAc) and then MeOH/CH$_2$Cl$_2$ (0 to 10% MeOH)
$^1$H NMR spectrum (DMSO d$_6$): 1.16(d, 3H); 1.20(m, 6H); 1.41(m, 4H); 1.61(m, 4H); 2.30(s, 6H); 2.55-2.95(m, 3H); 3.27(m, 2); 4.13(s, 2H); 4.53(s, 2H); 6.23(m, 1H); 6.42(d, 1H); 7.04(s, 1H); 7.07 (s, 2H); 7.21(t, 1H); 7.30(t, 2H); 7.35(d, 2H); 11.8(s br 1H).

Example 4.42

| R | CR43 mg; mmol Cf | CH$_2$Cl$_2$ ml | Propylamine ml; mmol | Mass mg; Yield | MS-ESI |
|---|---|---|---|---|---|
| ⸺CH$_2$⸺C$_6$H$_4$⸺OCH$_3$ (p-methoxybenzyl) | nd*; 0.25 | 5 | 0.27; 4.5 | 98; 72% | 545 [M + H]$^+$ |

Chromato.-EtOAc/CH$_2$Cl$_2$ (50 to 100% EtOAc) and then MeOH/CH$_2$Cl$_2$ (0 to 10% MeOH)

$^1$H NMR spectrum (DMSO d$_6$): 1.14(d, 3H); 1.20(m, 6H); 1.42(m, 4H); 1.61(m, 4H); 2.31(s, 6H); 2.61(m, 1H); 2.68(m, 1H); 2.85(m, 1H); 3.53(s, 2H); 3.70(s, 3H); 4.12(m, 2H); 4.56(s, 2H); 6.81(d, 2H); 7.03(s, 1H); 7.07(s, 2H); 7.12(d, 2H); 11.8(s br 1H).

Example 4.43

| R | CR44 mg; mmol Cf | CH$_2$Cl$_2$ ml | Propylamine ml; mmol | Mass mg; Yield | MS-ESI |
|---|---|---|---|---|---|
| ⸺CH$_2$CH$_2$⸺C$_6$H$_4$⸺NHC(O)NH⸺iPr | nd*; 0.25 | 5 | 0.27; 3.3 | 100; 63% | 629 [M + H]$^+$ |

Chromato.-EtOAc/CH$_2$Cl$_2$ (0 to 100% EtOAc) and then MeOH/CH$_2$Cl$_2$ (0 to 10% MeOH)

$^1$H NMR spectrum (DMSO d$_6$): 1.08(d, 6H); 1.18(d, 3H); 1.26(s, 6H); 1.42(m, 4H); 1.60(m, 4H); 2.31(s, 6H); 2.55-2.95(m, 7H); 3.73(m, 1H); 4.18(m, 2H); 4.56(s, 2H); 5.95(s, 1H); 6.96(d, 2H); 7.04(s, 3H); 7.25(d, 2H); 8.22 (s, 1H); 11.8(s br 1H).

Example 4.44

Example C45 was prepared by a different methodology (reductive amination of Ce): see below.

Example 4.45

| R | CR46 mg; mmol Cf | CH$_2$Cl$_2$ ml | Propylamine ml; mmol | Mass mg; Yield | MS-ESI |
|---|---|---|---|---|---|
| ⸺CH$_2$CH$_2$⸺C$_6$H$_4$⸺NH$_2$ | 108; 0.14 | 3 | 0.17; 2.0 | 71; 93% | 544 [M + H]$^+$ |

Chromato.-EtOAc and then MeOH/CH$_2$Cl$_2$ (0 to 15% MeOH)

$^1$H NMR spectrum (DMSO d$_6$): 1.14(d, 3H); 1.25(s, 6H); 1.42(m, 4H); 1.61(m, 4H); 2.3(s, 6H); 2.55-2.95(m, 7H); 4.14(s, 2H); 4.57(s, 2H); 4.83(s, 2H); 6.44(d, 2H); 6.74(d, 2H); 7.04(s, 1H); 7.05(s, 2H); 11.8(s br, 1H).

Example 4.46

| R | CR47 mg; mmol | CH₂Cl₂ ml | Propylamine ml; mmol | Mass mg; Yield | MS ESI |
|---|---|---|---|---|---|
| 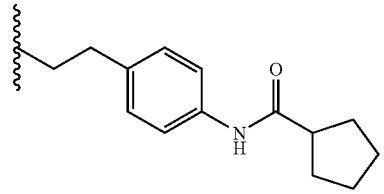 | nd*; 0.14 | 5 | 0.15; 1.8 | 41; 45% | 640 [M + H]⁺ |

Chromato.-EtOAc/CH$_2$Cl$_2$ (0 to 100% EtOAc) and then MeOH/CH$_2$Cl$_2$ (0 to 10% MeOH)
$^1$H NMR spectrum (DMSO d$_6$): 1.18(d, 3H); 1.25(m, 6H); 1.42(m, 4H); 1.5-1.9(m, 12H); 2.31(s, 6H); 2.55-2.95(m, 8H); 4.16(m, 2H); 4.56(s, 2H); 7.03(m, 5H); 7.51(d, 2H); 9.81; (s, 1H); 11.8(s br, 1H).

Example 4.47

| R | CR48 mg; mmol Cf | CH₂Cl₂ ml | Propylamine ml; mmol | Mass mg; Yield | MS-ESI |
|---|---|---|---|---|---|
| 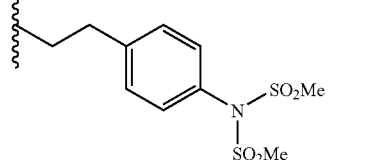 | nd*; 0.15 | 3 | 0.12; 1.5 | 135; 99% | 700 [M + H]⁺ |

Chromato.-EtOAc/CH$_2$Cl$_2$ (0 to 100% EtOAc)
$^1$H NMR spectrum (DMSO d$_6$-TFAd): 1.28(m, 9H); 1.43(m, 4H); 1.62(m, 4H); 2.33(s, 6H); 2.8-3.25(m, 7H); 3.51(s, 6H); 4.23(m, 2H); 4.57(s, 2H); 7.05(s, 2H); 7.08(s, 1H); 7.31(d, 2H); 7.47(d, 2H); 11.8(s br, 1H).

Example 4.48

| R | CR49 mg; mmol Cf | CH₂Cl₂ ml | Propylamine ml; mmol | Mass mg; Yield | MS-ESI |
|---|---|---|---|---|---|
|  | nd*; 0.25 | 3 | 0.15; 2.5 | 80; 60% | 535 [M + H]⁺ |

Chromato.-EtOAc/CH$_2$Cl$_2$ (0 to 100% EtOAc) and then MeOH/CH$_2$Cl$_2$ (0 to 10% MeOH)
$^1$H NMR spectrum (DMSO d$_6$): 1.13(d, 3H); 1.25(s, 6H); 1.42(m, 4H); 1.61(m, 4H); 2.30(s, 6H); 2.55-2.95(m, 7H); 4.15(m, 2H); 4.57(s, 2H); 6.76(d, 1H); 6.90(dd, 1H); 7.02(s, 1H); 7.05(s, 2H); 7.27(d, 1H); 11.76(s br, 1H).

Example 4.49

| R | CR50 mg; mmol Cf | CH₂Cl₂ ml | Propylamine ml; mmol | Mass mg; Yield | MS-ESI |
|---|---|---|---|---|---|
| 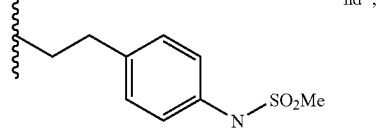 | nd*; 0.6 | 5 | 0.355; 6 | 181; 49% | 622 [M + H]⁺ |

Chromato.-MeOH/CH$_2$Cl$_2$ (0 to 10% MeOH)
$^1$H NMR spectrum (DMSO d$_6$): 1.12(d, 3H); 1.25(s, 6H); 1.41(m, 4H); 1.60(m, 4H); 2.29(s, 6H); 2.55-2.85 (m, 7H); 2.92(s, 3H); 4.14(s, 2H); 4.57(s, 2H); 7.06(m, 7H); 11.74(s br, 1H).

Example 4.50

| R | CR51 mg; mmol Cf | CH$_2$Cl$_2$ ml | Propylamine ml; mmol | Mass mg; Yield | MS-ESI |
|---|---|---|---|---|---|
| (4-(isopropoxycarbonylamino)phenethyl) | nd*; 0.15 | 3 | 0.09; 1.5 | 63; 67% | 630 [M + H]$^+$ |

Chromato.-MeOH/CH$_2$Cl$_2$ (0 to 10% MeOH)
$^1$H NMR spectrum (DMSO d$_6$): 1.16(d, 3H); 1.25(m, 12H); 1.42(m, 4H); 1.60(m, 4H); 2.30(s, 6H); 2.55-2.95(m, 7H); 4.16(m, 2H); 4.5(s, 2H); 4.87; (m, 1H); 7.0(d, 2H); 7.04(s, 3H); 7.34(s, 2H); 9.44(s, 1H); 11.8(s br, 1H).

Example 4.51

| R | CR52 mg; mmol Cf | CH$_2$Cl$_2$ ml | Propylamine ml; mmol | Mass mg; Yield | MS-ESI |
|---|---|---|---|---|---|
| (4-(3-cyclohexylureido)phenethyl) | nd*; 0.11 | 2 | 0.065; 1.1 | 42; 57% | 669 [M + H]$^+$ |

Chromato.-MeOH/CH$_2$Cl$_2$ (0 to 15% MeOH)
$^1$H NMR spectrum (DMSO d$_6$): 1.16(d, 3H); 1.25(s, 6H); 1.25-1.8(m, 18H); 2.31(s, 6H); 2.55-2.95(m, 7H); 3.43(m, 1H); 4.16(m, 2H); 4.56(s, 2H); 6.04(s, 1H); 6.96(d, 2H); 7.04(s, 3H); 7.25(d, 2H); 8.25(s, 1H); 11.86(s br, 1H).

Example 4.52

| R | CR53 mg; mmol Cf | CH$_2$Cl$_2$ ml | Propylamine ml; mmol | Mass mg; Yield | MS-ESI |
|---|---|---|---|---|---|
| (2-cyclohexylethyl) | nd*; 0.4 | 5 | 0.24; 4 | 93; 44% | 535 [M + H]$^+$ |

Chromato.-EtOAc
$^1$H NMR spectrum (DMSO d$_6$): 1.13(d, 3H); 1.25(s, 6H); 1.1-1.7(m, 21H); 2.3(s, 6H); 2.35-2.85(m, 5H); 4.15(s, 2H); 4.57(s, 2H); 7.03(s, 1H); 7.06(s, 2H) 11.8(s br, 1H).

Example 4.53

Example 4.53 was prepared by a different methodology (alkylation of Ce): see below

Example 4.54

| R | CR55 mg; mmol Cf | CH$_2$Cl$_2$ ml | Propylamine ml; mmol | Mass mg; Yield | MS-ESI |
|---|---|---|---|---|---|
| (1-methyl-2-oxo-1,2-dihydroquinolin-6-yl)ethyl | nd*; 0.25 | 5 | 0.15; 2.5 | 64; 42% | 610 [M + H]$^+$ |

Chromato.-EtOAc and then MeOH/CH$_2$Cl$_2$ (0 to 10% MeOH)
$^1$H NMR spectrum (DMSO d$_6$): 1.16(m, 3H); 1.25(s, 6H); 1.41(m, 4H); 1.59(m, 4H); 2.28(s, 6H); 2.55-3.0(m, 7H); 3.60(s, 3H); 4.16(s, 2H); 4.56(s, 2H); 6.6(d, 1H); 7.02(s, 3H); 7.42(m, 3H); 7.81(d, 1H); 11.8(s br, 1H).
*nd = not determined, partially purified CR used directly from previous step.

Example 4.34

2-[3-(2, methyl-3-oxo-3-azabicyclo[2.2.1]heptan-7-ylpropoxy)-5-(3,5-dimethylphenyl)-1H-pyrazol-4-yl]-N-[2-hydroxy-2-phenylethyl]-(2S)-propylamine

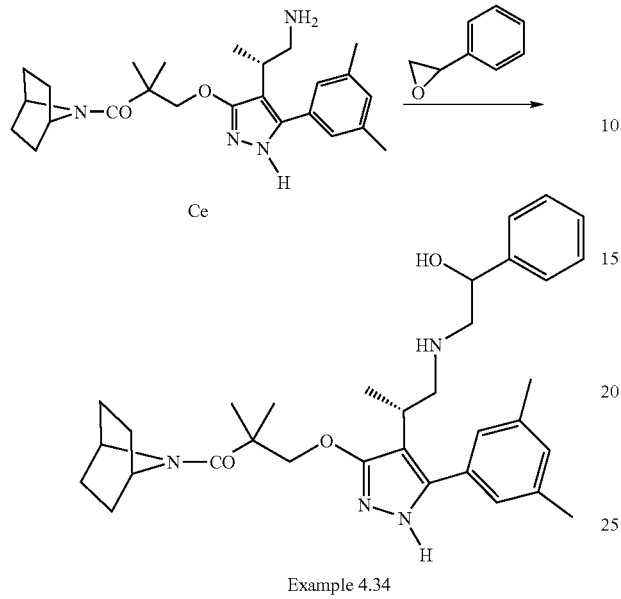

Example 4.34

A solution of Ce (106 mg; 0.25 mmol) in acetonitrile (3 ml) was treated with styrene oxide and the mixture was heated at 60° C. overnight. The solvent was evaporated and the residue purified by flash chromatography eluting with increasingly polar mixtures of MeOH/CH$_2$Cl$_2$ hexanes (0 to 10% MeOH) to give Example 4.34 as a white foam (40 mg).

Yield: 30%.

$^1$H NMR spectrum (DMSO d$_6$): 1.15 (m, 3H); 1.26 (m, 6H); 1.42 (m, 4H); 1.61; (m, 4H); 2.29 (s, 6H); 2.55-2.95 (m, 5H); 4.16 (m, 2H); 4.57 (m, 3H); 7.06 (m, 3H); 7.26 (m, 5H); 11.6 (s br, 1H).

MS-ESI: 545 [M+H]$^+$

Example 4.44

2-[3-(2,2-dimethyl-3-oxo-3-azabicyclo[2.2.1]heptan-7-ylpropoxy)-5-(3,5-dimethylphenyl)-1H-pyrazol-4-yl]-N-[2-methyl-2-phenylethyl]-(2S)-propylamine

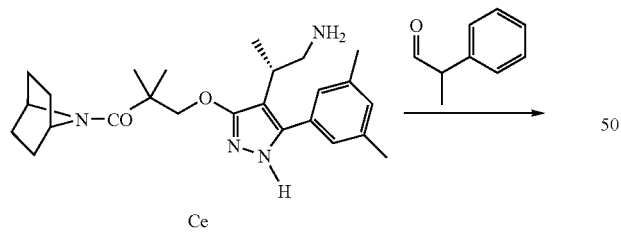

Example 4.44

A solution of Ce (126 mg; 0.3 mmol) and 2-phenyl propionaldehyde (45 µl; 0.3 mmol) in methanol (6 ml) under argon was cooled to 0° C. Sodium cyanoborohydride (39 mg; 0.6 mmol) was added portionwise and the mixture was stirred for 3 h. The methanol was evaporated and the residue taken up in CH$_2$Cl$_2$. The organic phase was washed with sat. aq. NaHCO$_3$, brine and dried over MgSO$_4$. The residue was purified by flash chromatography eluting with increasingly polar mixtures of EtOAc/CH$_2$Cl$_2$ (0 to 100% EtOAc) and then MeOH/CH$_2$Cl$_2$ (0 to 10% MeOH) to give Example 4.44 as a white foam (88 mg).

Yield: 54%.

$^1$H NMR spectrum (DMSO d$_6$): 1.10 (m, 6H); 1.24 (s, 6H); 1.41 (m, 4H); 1.60 (m, 4H); 2.28 (m, 6H); 2.55-2.95 (m, 6H); 4.14 (s, 2H); 4.56 (s, 2H); 7.03 (s, 3H); 7.09 (t, 2H); 7.16 (d, 1H); 7.23 (t, 2H); 11.8 (s br 1H).

MS-ESI: 543 [M+H]$^+$

Example 4.53

2-[3-(2,2-dimethyl-3-oxo-3-azabicyclo[2.2.1]heptan-7-ylpropoxy)-5-(3,5-dimethylphenyl)-1H-pyrazol-4-yl]-N-[1H-1,2,3-benzotriazol-5-ylaminocarbonylmethyl]-(2S)-propylamine

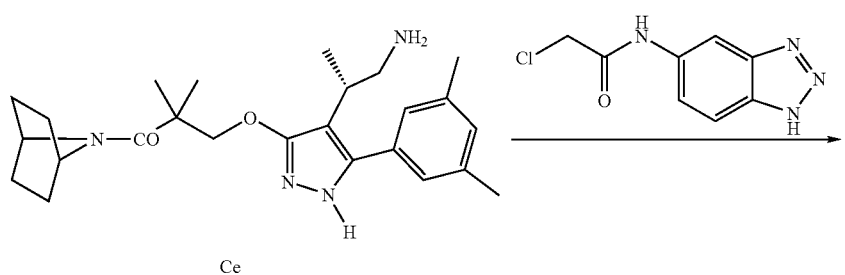

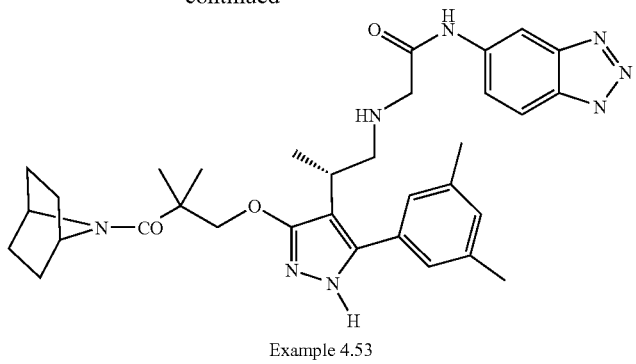

Example 4.53

To a solution of Ce (200 mg; 0.47 mmol) in DMA (1 ml) at 140° C. was added solid N-1H-1,2,3-benzotriazole-5-yl-2-chloroacetamide (98 mg; 0.47 mmol) over 5 min. The reaction mixture was heated at 140° C. for a further 5 min. The resulting orange solution was allowed to cool to room temperature and purified by flash chromatography on silica gel eluting with $CH_2Cl/NH_3$ in MeOH (0 to 5% $NH_3$ in MeOH) to give Example 4.53 (110 mg).

Yield: 37%

$^1$H NMR spectrum (CDCl$_3$): 1.20 (d, 3H); 1.22 (s, 6H); 1.40 (m, 4H); 1.70 (m, 4H); 2.31 (s, 6H); 2.77 (m, 1H); 2.99 (m, 2H); 3.34 (s, 2H), 4.28 (m, 2H); 4.57 (s, 2H); 5.37 (s, 1H); 6.95 (s, 2H); 7.02 (s, 1H); 7.17 (br d, 1H); 7.84 (br d, 1H); 8.26 (s, 1H); 9.50 (br s, 1H); 9.67 (s, 1H).

MS-ESI: 599 [M+]$^+$

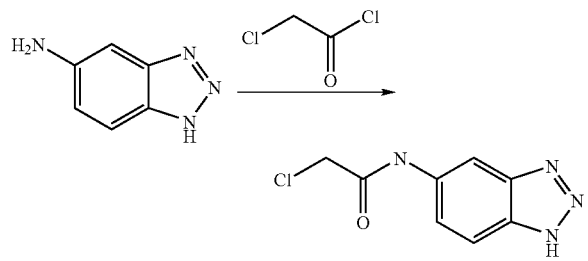

To a stirred solution of 5-aminobenzotriazole (1.00 g; 7.50 mmol) in THF (20 ml) at −10° C., were added triethylamine (0.987 g; 9.75 mmol) and chloroacetyl chloride (0.841 g; 7.50 mmol) dropwise over 5 min. The reaction mixture was allowed to warm to room temperature and stirred overnight.

The resulting precipitate was collected by filtration, washed with $CH_2Cl_2$ and dried to afford N-1H-1,2,3-benzotriazole-5-yl-2-chloroacetamide (1.32 g) as a beige solid.

Yield: 83.5%

$^1$H NMR spectrum (DMSO d$_6$): 4.33 (s, 2H); 7.42 (br d, 1H); 7.91 (br d, 1H); 8.35 (s, 1H).

MS-ESI: 211 [M+H]$^+$

Intermediates for Examples 4.1-4.55, CR1-CR55 Respectively

Starting materials CR1-CR55 were prepared as follows, the table showing the reaction conditions and characteristics for each example, corresponding to the description of Example 4 given above:—

| CR1 | | | | | | |
|---|---|---|---|---|---|---|
| R | Cf mg; mmol | Alcohol mg; mmol | Ph$_3$P mg; mmol | DEAD mg; mmol | Mass mg | MS-ESI |
|  | 200; 0.3 | 44; 0.36 | 470; 1.8 | 170; 1.2 | 188 | 760 [M + H]$^+$ |

Chromato.-EtOAc/CH$_2$Cl$_2$ (0 to 100% EtOAc).

| CR2 | | | | | | |
|---|---|---|---|---|---|---|
| R | Cf mg; mmol | Alcohol mg; mmol | Ph$_3$P mg; mmol | DEAD mg; mmol | Mass mg | MS-ESI |
|  | 200; 0.3 | 56; 0.37 | 470; 1.8 | 170; 1.2 | 202 | 788 [M + H]$^+$ |

Chromato.-EtOAc/CH$_2$Cl$_2$ (50 to 100% EtOAc).

CR3

| R | Cf mg; mmol | Alcohol mg; mmol | Ph₃P mg; mmol | DEAD mg; mmol | Mass mg | MS-ESI |
|---|---|---|---|---|---|---|
| 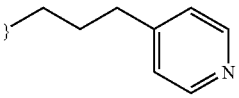 | 80; 0.12 | 20; 0.15 | 192; 0.73 | 70; 0.49 | 68 | 774 [M + H]⁺ |

Chromato.-EtOAc/CH₂Cl₂ (0 to 100% EtOAc).

CR4

| R | Cf mg; mmol | Alcohol mg; mmol | Ph₃P mg; mmol | DEAD mg; mmol | Mass mg | MS-ESI |
|---|---|---|---|---|---|---|
| 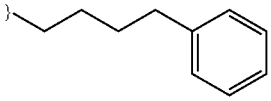 | 130; 0.2 | 36; 0.24 | 300; 1.13 | 100; 0.7 | 514 | 787 [M + H]⁺ |

Chromato.-EtOAc/CH₂Cl₂ (0 to 40% EtOAc)

CR5

| R | Cf mg; mmol | Alcohol mg; mmol | Ph₃P mg; mmol | DTAD mg; mmol | Mass mg | MS-ESI |
|---|---|---|---|---|---|---|
| 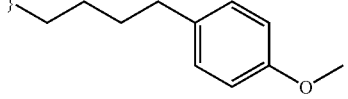 | 327; 0.5 | 100; 0.6 | 786; 3 | 460; 2 | nd* | nd* |

Chromato.-EtOAc/CH₂Cl₂ (0 to 50% EtOAc).

CR6

| R | Cf mg; mmol | Alcohol mg; mmol | Ph₃P mg; mmol | DEAD mg; mmol | Mass mg | MS-ESI |
|---|---|---|---|---|---|---|
| 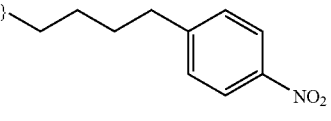 | 150; 0.23 | 53; 0.27 | 361; 1.38 | 0.145; 0.92 | 230 | 832 [M + H]⁺ |

Chromato.-EtOAc/CH₂Cl₂ (0 to 100% EtOAc).

CR7

| R | Cf mg; mmol | Alcohol mg; mmol | Ph₃P mg; mmol | DEAD mg; mmol | Mass mg | MS-ESI |
|---|---|---|---|---|---|---|
| 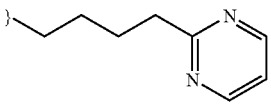 | 150; 0.23 | 42; 0.27 | 361; 1.38 | 0.145; 0.92 | nd* | 789 [M + H]⁺ |

Chromato.-EtOAc

CR8

| R | Cf mg; mmol | Alcohol mg; mmol | Ph₃P mg; mmol | DEAD mg; mmol | Mass mg | MS-ESI |
|---|---|---|---|---|---|---|
|  | 150; 0.23 | 42; 0.27 | 360; 138 | 0.15; 90 | nd* | 789 [M + H]⁺ |

Chromato.-EtOAc/CH₂Cl₂ (0 to 100% EtOAc)

CR9

| R | Cf mg; mmol | Alcohol mg; mmol | Ph₃P mg; mmol | DEAD mg; mmol | Mass mg | MS-ESI |
|---|---|---|---|---|---|---|
|  | nd*; 0.38 | 81; 0.55 | 724; 2.76 | 0.245; 1.55 | 94; 45% | nd* |

Chromato.-EtOAc

CR10

| R | Cf mg; mmol | Alcohol mg; mmol | Ph₃P mg; mmol | DTAD mg; mmol | Mass mg | MS-ESI |
|---|---|---|---|---|---|---|
|  | 150; 0.23 | 47; 0.27 | 361; 1.38 | 212; 0.93 | nd* | 809 [M + H]⁺ |

Chromato.-EtOAc/CH₂Cl₂ (0 to 70% EtOAc).

CR11

| R | Cf mg; mmol | Alcohol mg; mmol | Ph₃P mg; mmol | DTAD mg; mmol | Mass mg | MS-ESI |
|---|---|---|---|---|---|---|
|  | 150; 0.23 | 42; 0.27 | 361; 1.38 | 212; 0.93 | nd* | 789 [M + H]⁺ |

Chromato.-EtOAc/CH₂Cl₂ (0 to 70% EtOAc).

CR12

| R | Cf mg; mmol | Alcohol mg; mmol | Ph₃P mg; mmol | DTAD mg; mmol | Mass mg | MS-ESI |
|---|---|---|---|---|---|---|
| 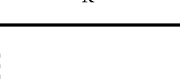 | 300; 0.46 | 73; 0.6 | 723; 2.76 | 423; 1.84 | nd* | nd* |

Chromato.-EtOAc/CH₂Cl₂ (0 to 30% EtOAc).

CR13

| R | Cf mg; mmol | Alcohol mg; mmol | Ph₃P mg; mmol | DTAD mg; mmol | Mass mg | MS-ESI |
|---|---|---|---|---|---|---|
| | 250; 0.38 | 95; 0.5 | 600; 2.28 | 350; 1.52 | nd* | nd* |

Chromato.-EtOAc/CH₂Cl₂ (0 to 40% EtOAc).

CR14

| R | Cf mg; mmol | Alcohol mg; mmol | Ph₃P mg; mmol | DTAD mg; mmol | Mass mg | MS-ESI |
|---|---|---|---|---|---|---|
| 3,4-dimethoxyphenethyl | 164; 0.25 | 55; 0.3 | 362; 1.38 | 212; 0.92 | nd* | nd* |

Chromato.-EtOAc/CH₂Cl₂ (0 to 70% EtOAc)

CR15

| R | Cf mg; mmol | Alcohol mg; mmol | Ph₃P mg; mmol | DTAD mg; mmol | Mass mg | MS-ESI |
|---|---|---|---|---|---|---|
| 4-dimethylaminophenethyl | 164; 0.25 | 49; 0.3 | 362; 1.38 | 212; 0.92 | nd* | nd* |

Chromato.-EtOAc/CH₂Cl₂ (0 to 100% EtOAc)

CR16

| R | Cf mg; mmol | Alcohol mg; mmol | Ph₃P mg; mmol | DTAD mg; mmol | Mass mg | MS-ESI |
|---|---|---|---|---|---|---|
| 4-fluorophenethyl | 300; 0.46 | 84; 0.6 | 723; 2.76 | 423; 1.84 | nd* | 777 [M + H]⁺ |

Chromato.-EtOAc/CH₂Cl₂ (0 to 20 EtOAc).

CR18

| Cgx | Cf mg; mmol | Alcohol mg; mmol | Ph₃P mg; mmol | DTAD mg; mmol | Mass mg | MS-ESI |
|---|---|---|---|---|---|---|
| 3,5-difluorophenethyl | 150; 0.23 | 50; 0.3 | 367; 1.4 | 212; 0.92 | 40 | nd* |

Chromato.-EtOAc/CH₂Cl₂ (0 to 20% EtOAc)

CR19

| R | Cf mg; mmol | Alcohol mg; mmol | Ph₃P mg; mmol | DTAD mg; mmol | Mass mg | MS-ESI |
|---|---|---|---|---|---|---|
| 4-tert-butylphenethyl | 163; 0.25 | 57; 0.32 | 393; 1.5 | 230; 1.0 | nd* | nd* |

Chromato.-EtOAc/CH₂Cl₂ (0 to 20% EtOAc)

CR20

| R | Cf mg; mmol | Alcohol mg; mmol | Ph₃P mg; mmol | DTAD mg; mmol | Mass mg | MS-ESI |
|---|---|---|---|---|---|---|
| 2,5-dimethylphenethyl | 163; 0.25 | 48; 0.32 | 393; 1.5 | 230; 1.0 | nd* | nd* |

Chromato.-EtOAc/CH₂Cl₂ (0 to 20% EtOAc)

CR21

| R | Cf mg; mmol | Alcohol mg; mmol | Ph₃P mg; mmol | DTAD mg; mmol | Mass mg | MS-ESI |
|---|---|---|---|---|---|---|
| 2-chloro-6-fluorophenethyl | 163; 0.25 | 56; 0.32 | 393; 1.5 | 230; 1.0 | nd* | nd* |

Chromato.-EtOAc/CH₂Cl₂ (0 to 20% EtOAc)

CR22

| R | Cf mg; mmol | Alcohol mg; mmol | Ph₃P mg; mmol | DTAD mg; mmol | Mass mg | MS-ESI |
|---|---|---|---|---|---|---|
| ![R group with 2-F, 4-Cl phenyl propyl] | 163; 0.25 | 56; 0.32 | 393; 1.5 | 230; 1.0 | nd* | nd* |

Chromato.-EtOAc/CH₂Cl₂ (0 to 20% EtOAc)

CR23

| R | Cf mg; mmol | Alcohol mg; mmol | Ph₃P mg; mmol | DTAD mg; mmol | Mass mg | MS-ESI |
|---|---|---|---|---|---|---|
| ![R group with 3,4-diCl phenyl propyl] | 163; 0.25 | 61; 0.32 | 393; 1.5 | 230; 1.0 | nd* | nd* |

Chromato.-EtOAc/CH₂Cl₂ (0 to 20% EtOAc)

CR24

| R | Cf mg; mmol | Alcohol mg; mmol | Ph₃P mg; mmol | DTAD mg; mmol | Mass mg | MS-ESI |
|---|---|---|---|---|---|---|
| ![R group with 2,6-diCl phenyl propyl] | 163; 0.25 | 61; 0.32 | 393; 1.5 | 230; 1.0 | nd* | nd* |

Chromato.-EtOAc/CH₂Cl₂ (0 to 20% EtOAc)

CR25

The intermediate CR25 was prepared as follows:—

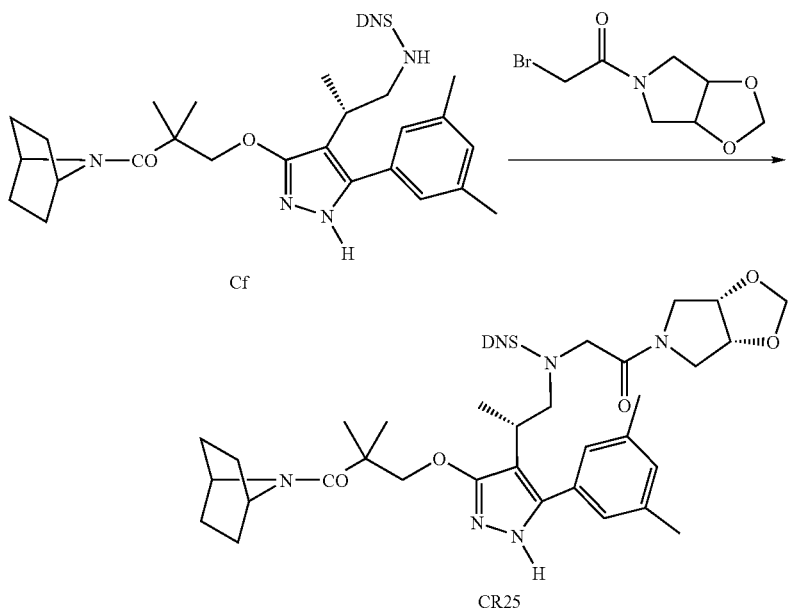

CR25

A solution of Cf (150 mg; 0.23 mmol) in DMF (3 ml) was cooled to 0° C. and treated with potassium t-butoxide (40 mg). The bromomethyl amide (82 mg; 0.35 mmol) was added and the mixture allowed to warm to room temperature for 1 h. The mixture was treated with sat. aq. NaHCO₃ and extracted with CH₂Cl₂ The organic phase was washed with water, brine and dried over MgSO₄. The crude product was used directly in the final step.

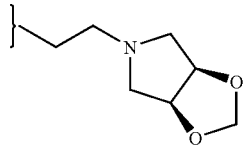

| | CR26 | | | | | |
|---|---|---|---|---|---|---|
| R | Cf mg; mmol | Alcohol mg; mmol | Ph₃P mg; mmol | DTAD mg; mmol | Mass mg | MS-ESI |
| (structure) | 150; 0.23 | 48; 0.3 | 367; 1.4 | 212; 0.92 | nd* | nd* |

Chromato.-EtOAc/CH₂Cl₂ (0 to 20 EtOAc).

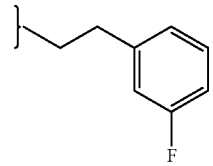

| | CR27 | | | | | |
|---|---|---|---|---|---|---|
| R | Cf mg; mmol | Alcohol mg; mmol | Ph₃P mg; mmol | DTAD mg; mmol | Mass mg | MS-ESI |
| (structure) | 173; 0.26 | 45; 0.32 | 415; 1.58 | 243; 1.06 | nd* | nd* |

Chromato.-EtOAc/CH₂Cl₂ (0 to 20 EtOAc).

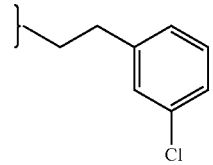

| | CR28 | | | | | |
|---|---|---|---|---|---|---|
| R | Cf mg; mmol | Alcohol mg; mmol | Ph₃P mg; mmol | DTAD mg; mmol | Mass mg | MS-ESI |
| (structure) | 173; 0.26 | 50; 0.32 | 415; 1.58 | 243; 1.06 | nd* | nd* |

Chromato.-EtOAc/CH₂Cl₂ (0 to 20 EtOAc).

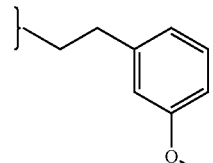

| | CR29 | | | | | |
|---|---|---|---|---|---|---|
| R | Cf mg; mmol | Alcohol mg; mmol | Ph₃P mg; mmol | DTAD mg; mmol | Mass mg | MS-ESI |
| (structure) | 173; 0.26 | 49; 0.32 | 415; 1.58 | 243; 1.06 | nd* | nd* |

Chromato.-EtOAc/CH₂Cl₂ (0 to 20 EtOAc).

CR30

| R | Cf mg; mmol | Alcohol mg; mmol | Ph₃P mg; mmol | DTAD mg; mmol | Mass mg | MS-ESI |
|---|---|---|---|---|---|---|
| 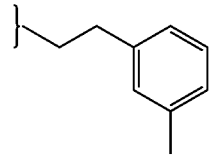 | 173; 0.26 | 44; 0.32 | 415; 1.58 | 243; 1.06 | nd* | nd* |

Chromato.-EtOAc/CH₂Cl₂ (0 to 20 EtOAc).

CR31

| R | Cf mg; mmol | Alcohol mg; mmol | Ph₃P mg; mmol | DTAD mg; mmol | Mass mg | MS-ESI |
|---|---|---|---|---|---|---|
| 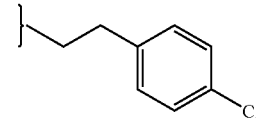 | 173; 0.26 | 50; 0.32 | 415; 1.58 | 243; 1.06 | nd* | nd* |

Chromato.-EtOAc/CH₂Cl₂ (0 to 20 EtOAc).

CR32

| R | Cf mg; mmol | Alcohol mg; mmol | Ph₃P mg; mmol | DTAD mg; mmol | Mass mg | MS-ESI |
|---|---|---|---|---|---|---|
| 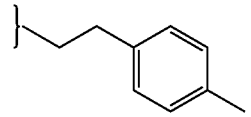 | 173; 0.26 | 44; 0.32 | 415; 1.58 | 243; 1.06 | nd* | nd* |

Chromato.-EtOAc/CH₂Cl₂ (0 to 20 EtOAc).

CR33

| R | Cf mg; mmol | Alcohol mg; mmol | Ph₃P mg; mmol | DTAD mg; mmol | Mass mg | MS-ESI |
|---|---|---|---|---|---|---|
| 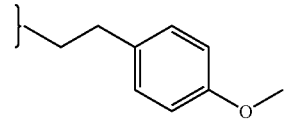 | 173; 0.26 | 49; 0.32 | 415; 1.58 | 243; 1.06 | nd* | nd* |

Chromato.-EtOAc/CH₂Cl₂ (0 to 20 EtOAc).

CR34

| R | Cf mg; mmol | Alcohol mg; mmol | Ph₃P mg; mmol | DTAD mg; mmol | Mass mg | MS-ESI |
|---|---|---|---|---|---|---|
| 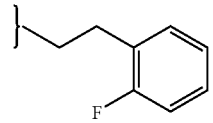 | 173; 0.26 | 45; 0.32 | 415; 1.58 | 243; 1.06 | nd* | nd* |

Chromato.-EtOAc/CH₂Cl₂ (0 to 20 EtOAc).

CR36

| R | Cf mg; mmol | Alcohol mg; mmol | Ph₃P mg; mmol | DTAD mg; mmol | Mass mg | MS-ESI |
|---|---|---|---|---|---|---|
| 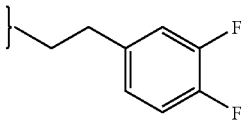 | 164; 0.25 | 52; 0.33 | 393; 1.5 | 230; 1 | nd* | nd* |

Chromato.-EtOAc/CH₂Cl₂ (10 to 50 EtOAc).

CR37

| R | Cf mg; mmol | Alcohol mg; mmol | Ph₃P mg; mmol | DTAD mg; mmol | Mass mg | MS-ESI |
|---|---|---|---|---|---|---|
| 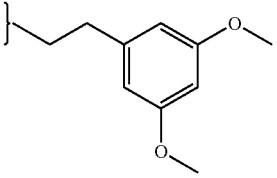 | 164; 0.25 | 60; 0.33 | 393; 1.5 | 230; 1 | nd* | nd* |

Chromato.-EtOAc/CH₂Cl₂ (10 to 50 EtOAc).

CR38

| R | Cf mg; mmol | Alcohol mg; mmol | Ph₃P mg; mmol | DTAD mg; mmol | Mass mg | MS-ESI |
|---|---|---|---|---|---|---|
| 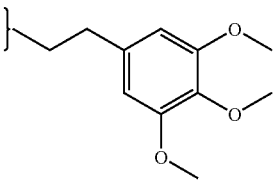 | 164; 0.25 | 70; 0.33 | 393; 1.5 | 230; 1 | nd* | nd* |

Chromato.-EtOAc/CH₂Cl₂ (10 to 50 EtOAc).

CR39

| R | Cf mg; mmol | Alcohol mg; mmol | Ph₃P mg; mmol | DTAD mg; mmol | Mass mg | MS-ESI |
|---|---|---|---|---|---|---|
| 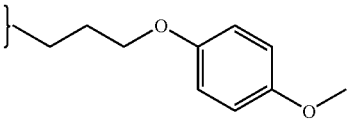 | 164; 0.25 | 60; 0.33 | 393; 1.5 | 230; 1 | nd* | nd* |

Chromato.-EtOAc/CH₂Cl₂ (10 to 50 EtOAc).

CR40

| R | Cf mg; mmol | Alcohol mg; mmol | Ph₃P mg; mmol | DTAD mg; mmol | Mass mg | MS-ESI |
|---|---|---|---|---|---|---|
| 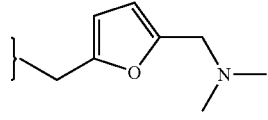 | 164; 0.25 | 63; 0.33 | 393; 1.5 | 230; 1 | nd* | nd* |

Chromato.-EtOAc/CH$_2$Cl$_2$ (10 to 50 EtOAc).

CR41

| R | Cf mg; mmol | Alcohol mg; mmol | Ph₃P mg; mmol | DTAD mg; mmol | Mass mg | MS-ESI |
|---|---|---|---|---|---|---|
| 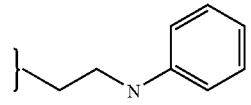 | 164; 0.25 | 45; 0.33 | 393; 1.5 | 230; 1 | nd* | nd* |

Chromato.-EtOAc/CH$_2$Cl$_2$ (10 to 50 EtOAc).

CR42

| R | Cf mg; mmol | Alcohol mg; mmol | Ph₃P mg; mmol | DTAD mg; mmol | Mass mg | MS-ESI |
|---|---|---|---|---|---|---|
| 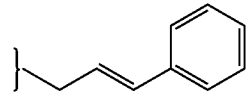 | 164; 0.25 | 44; 0.33 | 393; 1.5 | 230; 1 | nd* | nd* |

Chromato.-EtOAc/CH$_2$Cl$_2$ (10 to 50 EtOAc).

CR43

| R | Cf mg; mmol | Alcohol mg; mmol | Ph₃P mg; mmol | DTAD mg; mmol | Mass mg | MS-ESI |
|---|---|---|---|---|---|---|
| 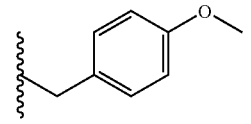 | 164; 0.25 | 46; 0.33 | 393; 1.5 | 230; 1 | nd* | nd* |

Chromato.-EtOAc/CH$_2$Cl$_2$ (10 to 50 EtOAc).

CR44

| R | Cf mg; mmol | Alcohol mg; mmol | Ph₃P mg; mmol | DTAD mg; mmol | Mass mg | MS-ESI |
|---|---|---|---|---|---|---|
| 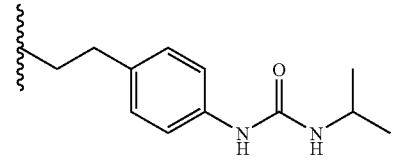 | 164; 0.25 | 75; 0.33 | 393; 1.5 | 230; 1 | nd* | 859 [M + H]⁺ |

Chromato.-EtOAc/CH$_2$Cl$_2$ (0 to 100% EtOAc)

CR45

| R | Cf mg; mmol | Alcohol mg; mmol | Ph₃P mg; mmol | DTAD mg; mmol | Mass mg | MS-ESI |
|---|---|---|---|---|---|---|
| 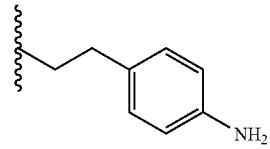 | 410; 0.62 | 130; 0.94 | 975; 3.72 | 570; 2.48 | 458(95%) | 774 [M + H]⁺ |

Chromato.-EtOAc/CH₂Cl₂ (0 to 100% EtOAc)
¹H NMR spectrum (DMSO d₆): 1.16(d, 3H); 1.28(s, 6H); 1.42(m, 4H); 1.60(m, 4H); 2.28(s, 6H); 2.40(m, 2H); 3.06(m, 1H); 3.18(m, 2H); 3.45-3.75(m, 2H); 4.17(dd, 2H); 4.56(s, 2H); 4.86(s, 2H); 6.37(d, 2H); 6.61(d, 2H); 7.01(s, 3H); 8.08 (d, 1H); 8.43(dd, 1H); 8.86(d, 1H); 11.8(s br, 1H).

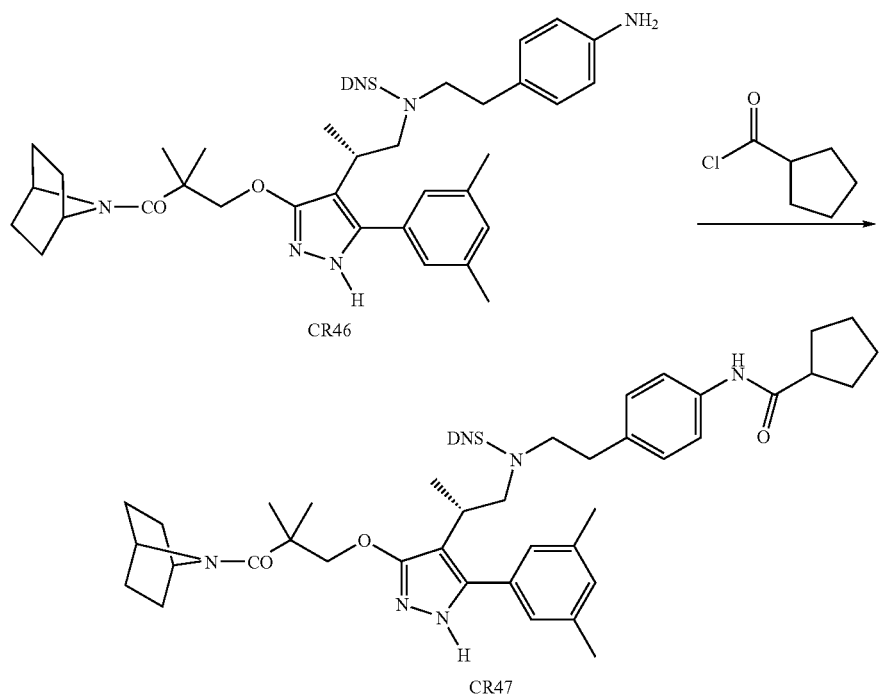

solution of CR46 (108 mg; 0.14 mmol) in CH₂Cl₂ (2 ml) was cooled to 0° C. and treated with DIEA (27 µl; 0.154 mmol). A solution of the acid chloride (14 µl; 0.11 mmol) in CH₂Cl₂ (1 ml) was added and the mixture allowed to warm to room temperature. The crude mixture was deprotected as described for C47 above.

CR48
This intermediate was prepared using a method analogous to the preparation of CR47.

| R | Cg46 mg; mmol | DIEA µl; mmol | Acid chloride µl; mmol | CH₂Cl₂ | Mass mg | MS-ESI |
|---|---|---|---|---|---|---|
| 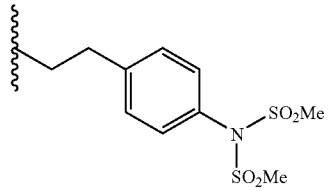 | 120; 0.15 | 29; 0.16 | 30; 0.36 | 3 | nd* | nd* |

Chromato.-EtOAc

CR49

| R | Cf mg; mmol | Alcohol mg; mmol | Ph₃P mg; mmol | DTAD mg; mmol | Mass mg | MS-ESI |
|---|---|---|---|---|---|---|
| 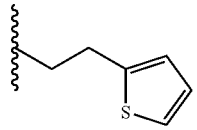 | 164; 0.25 | 50; 0.37 | 393; 1.5 | 230; 1 | nd* | nd* |

Chromato.-EtOAc/CH₂Cl₂ (0 to 50% EtOAc)

CR50
This intermediate was prepared using a method analogous to the preparation of CR47.

| R | CR46 mg; mmol | DIBA μl; mmol | Acid chloride μl; mmol | CH₂Cl₂ | Mass mg | MS-ESI |
|---|---|---|---|---|---|---|
| 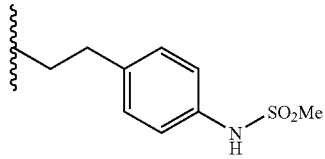 | 630; 0.6 | 315; 1.8 | 95; 1.2 | 50 | nd* | nd* |

Chromato.-EtOAc/CH₂Cl₂ (0 to 100% EtOAc)

CR51
This intermediate was prepared using a method analogous to the preparation of CR47.

| R | CR46 mg; mmol | DIEA μl mmol | Acid chloride μl; mmol | CH₂Cl₂ | Mass mg | MS-ESI |
|---|---|---|---|---|---|---|
| 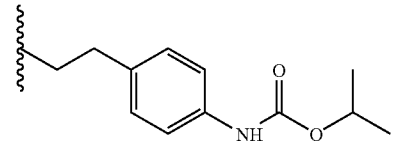 | 120; 0.15 | 100; 0.6 | 300 1M; 0.15 | 3 | nd* | 860 [M + H]⁺ |

Chromato.-EtOAc/CH₂Cl₂ (0 to 50% EtOAc)

CR52
This intermediate was prepared using a method analogous to the preparation of CR47.

| R | CR46 mg; mmol | DIEA μl; mmol | Acid chloride** μl; mmol | CH₂Cl₂ | Mass mg | MS-ESI |
|---|---|---|---|---|---|---|
| 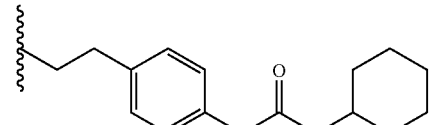 | 88; 0.11 | 100; 0.6 | 50; 0.4 | 10 | nd* | nd* |

Chromato.-EtOAc/CH₂Cl₂ (0 to 50% EtOAc)
**Cyclohexyl isocyanate was used in place of the corresponding acid chloride.

CR53

| R | Cf mg; mmol | Alcohol mg; mmol | Ph₃P mg; mmol | DTAD mg; mmol | Mass mg | MS-ESI |
|---|---|---|---|---|---|---|
| 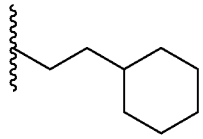 | 262; 0.4 | 102; 0.8 | 629; 2.4 | 368; 1.6 | nd* | nd* |

Chromato.-EtOAc/CH₂Cl₂ (0 to 20% EtOAc)

CR55

| R | Cf mg; mmol | Alcohol mg; mmol | Ph₃P mg; mmol | DTAD mg; mmol | Mass mg | MS-ESI |
|---|---|---|---|---|---|---|
| 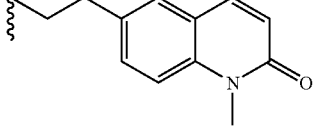 | 164; 0.25 | 70; 0.34 | 393; 1.5 | 230; 1 | nd* | 840 [M + H]⁺ |

Chromato.-EtOAc/CH₂Cl₂ (0 to 20% EtOAc)
*nd = not determined, partially purified Cgx used directly for final step.

Example 5

3-[2,2-dimethyl-3-oxo-3-(pyrrolidin-1-yl)propoxy]-4-[4-(2-pyrrolidin-1-yl-2-oxo-ethyl)piperzin-1-yl-ethyl]-5-(3,5-dimethylphenyl)-1H-pyrazole

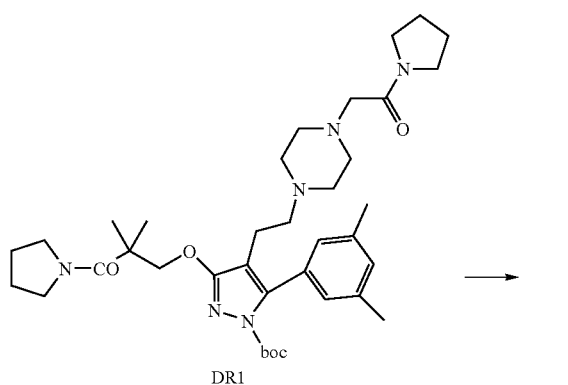

solution of DR1 (350 mg; 0.53 mmol) in pyrrolidine (2 ml) was heated at 45° C. overnight. The pyrrolidine was evaporated and the residue purified by flash chromatography eluting with increasingly polar mixtures of MeOH/CH₂Cl₂ (0 to 7% MeOH) to give Example 5 as a colourless foam (288 mg).

Yield: 97%

$^1$H NMR spectrum (CDCl₃): 1.38 (s, 6H); 1.78 (m, 4H); 1.84 (m, 2H); 1.94 (m, 2H); 2.35 (s, 6H); 2.5-2.7 (m, 12H); 3.10 (s, 2H); 3.47 (t, 4H); 3.58 (m, 4H); 4.32 (s, 2H); 7.03 (s, 1H); 7.27 (s, 2H); 8.8 (s br, 1H).

MS-ESI: 565 [M+H]⁺

The starting material DR1 was prepared as follows:—

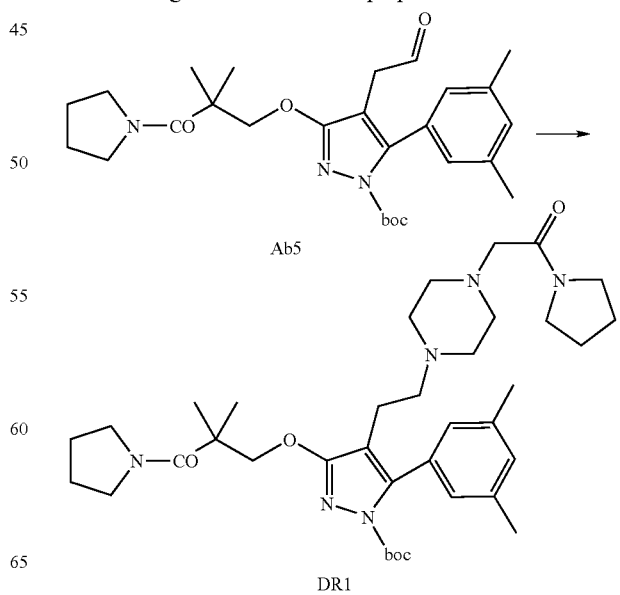

A solution of Ab5 (242 mg; 0.5 mmol) and 4-(4-aminobutyl)-pyridine (125 mg; 0.65 mmol) in DCE (5 ml) was treated with NaBH(OAc)$_3$ (425 mg; 2.0 mmol). The mixture was stirred for 20 h and evaporated. The residue was treated with aq. K$_2$CO$_3$ (10%) and the mixture extracted with EtOAc. The organic phase was washed with water, brine and dried over MgSO$_4$. The solution was evaporated to give pure DR1 as an white solid (350 mg).

Yield: 100%

$^1$H NMR spectrum (CDCl$_3$): 1.20 (s, 9H); 1.36 (s, 6H); 1.74 (s, 4H); 1.84 (m, 2H); 1.92 (m, 2H); 2.31 (s, 6H); 2.4-2.6 (m, 12H); 3.07 (s, 2H); 3.46 (t, 4H); 3.57 (m, 4H); 4.45 (s, 2H); 6.81 (s, 2H); 6.98 (s, 1H).

MS-ESI: 665 [M+H]$^+$

Examples 5.1-5.2

The following Example 5.1 was prepared in a similar manner to Example 5 and Example 5.2 was prepared in a manner similar to Example 2.

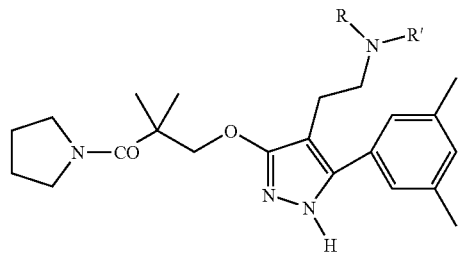

the table shows the NRR' group relating to the above structure, the reaction conditions and characteristics for each example, corresponding to the description of the preparation of Example 5 given above:—

Example 5.1

| —NRR' | DR2 mg; mmol | Pyrrolidine ml; mmol | Prod. Form | Mass mg; Yield | MS-ESI |
|---|---|---|---|---|---|
|  | 85; 0.14 | 2; 2.86 | White glass | 68; 96% | 516 [M + H]$^+$ |

Chromato.-MeOH/CH$_2$Cl$_2$ (7 to 10% MeOH)
$^1$H NMR spectrum (CDCl$_3$): 1.39(s, 6H); 1.70(s, 4H); 1.83(m, 2H); 2.35(s, 6H); 2.5-2.9(m, 7H); 3.0(m, 1H); 3.3(m, 1H); 3.58 (m, 4H); 4.34(dd, 2H); 7.03(s, 1H); 7.04(s, 2H); 7.17(d, 2H); 8.48(d, 2H); 8.9(s br 1H).

Example 5.2

| —NRR' | DR3 mg; mmol | CH$_2$Cl$_2$ | Prod. Form | Mass mg; Yield | MS-ESI |
|---|---|---|---|---|---|
|  | 194; 0.3 | 2 | White solid | 86; 52% | 551 [M + H]$^+$ |

Chromato.-LC/MS H$_2$O/MeCN buffered with ammonium carbonate at pH 8.9 (0 to 100% H$_2$O)
$^1$H NMR spectrum (CDCl$_3$): 1.36(s, 6H); 1.74(m, 4H); 1.83(m, 4H); 2.32(s, 6H); 2.4-2.7(m, 20H); 3.56(m, 4H); 4.30(s, 2H); 7.01(s, 1H); 7.02(s, 2H); 8.8(s br 1H).

Intermediates for Examples 5.1-5.2, DR2-DR3 Respectively

Starting materials DR2-3 were prepared as follows, the table showing the reaction conditions and characteristics for each example, corresponding to the description of DR1 given above:—

Example 6

3-[2,2-dimethyl-3-oxo-3-(azabicyclo[2.2.1]heptan-7-yl)propoxy]-4-[4-(2-pyrrolidin-1-yl-2-oxo-ethyl)piperzin-1-ylethyl]-5-(3,5-dimethylphenyl)-1H-pyrazole

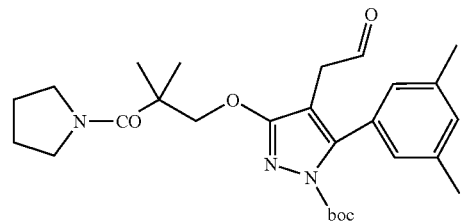

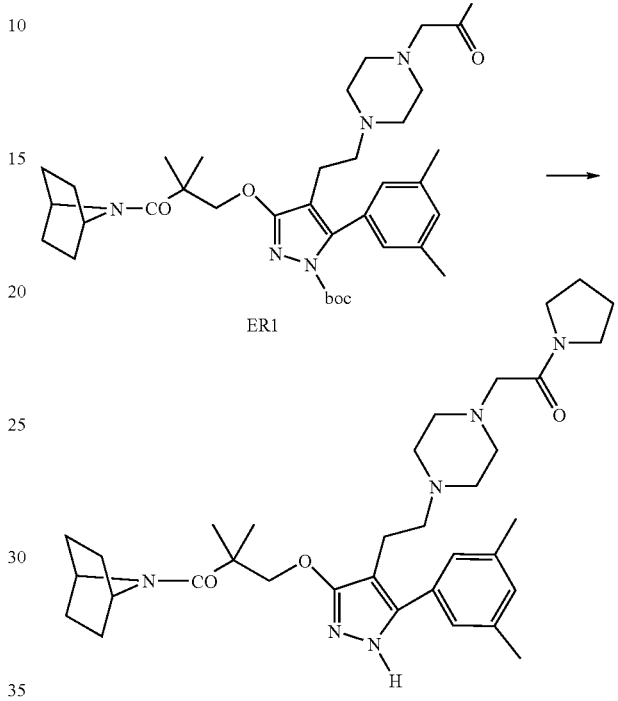

| —NRR' | DR2 Ab5 mg; mmol | Amine mg; mmol | NaBH(OAc)₃ mg; mmol | Mass mg; Yield | MS-ESI |
|---|---|---|---|---|---|
| (pyrrolidin-3-yl-pyridine) | 150; 0.31 | 60; 0.39 | 200; 0.93 | 117; 61% | 616 [M + H]⁺ |

Chromato.-EtOAc then MeOH/CH₂Cl₂ (5% MeOH)
¹H NMR spectrum (CDCl₃): 1.20(s, 9H); 1.37(s, 6H); 1.70(s, 4H); 1.90(m, 2H); 2.30(s, 6H); 2.4-2.7(m, 7H); 2.9(m, 1H); 3.3(m, 1H); 3.56(m, 4H); 4.47(dd, 2H); 6.80(s, 2H); 6.99(s, 1H); 7.15(d, 2H); 8.48(d, 2H).

| —NRR' | DR3 Ab5 mg; mmol | Amine mg; mmol | NaBH₄ mg; mmol | Mass mg; Yield | MS-ESI |
|---|---|---|---|---|---|
| (piperazinyl-ethyl-pyrrolidine) | 265; 0.55 | 110; 0.6 | 38; 0.6 + AcOH 35 μM | 194; 54% | 651 [M + H]⁺ |

Chromato.-Ammonia in MeOH(7N)/CH₂Cl₂ (0 to 10% ammonia in MeOH).

A solution of ER1 (160 mg; 0.23 mmol) in pyrrolidine (1 ml) was heated at 45° C. overnight. The pyrrolidine was evaporated and the residue purified by flash chromatography eluting with increasingly polar mixtures of MeOH/CH$_2$Cl$_2$ (5 to 10% MeOH) to give Example 6 as a white solid (141 mg).

Yield: 100%

$^1$H NMR spectrum (CDCl$_3$): 1.36 (s, 6H); 1.46 (m, 4H); 1.77 (m, 4H); 1.83 (m, 2H); 1.93 (m, 2H); 2.35 (s, 6H); 2.45-2.65 (m, 12H); 3.11 (s, 2H); 3.47 (m, 4H); 4.28 (s, 2H); 4.65 (s, 2H); 7.03 (s, 2H); 7.26 (s, 1H); 8.8 (s br, 1H).

MS-ESI: 591 [M+H]$^+$

Starting material ER1 was prepared as follows:—

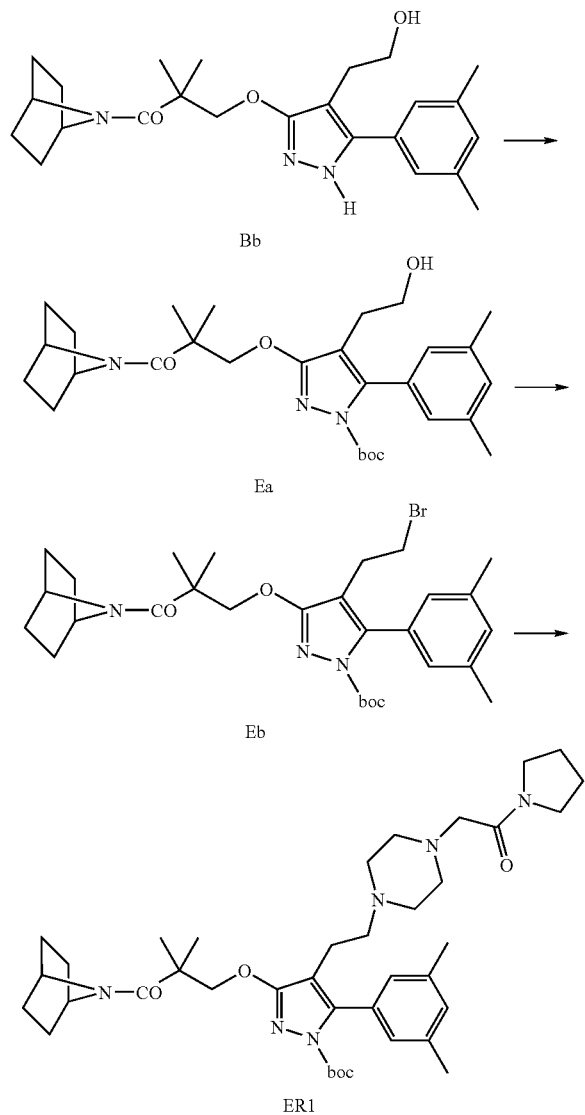

DMAP (100 mg; cat.) was added to a solution of Bb (4.0 g; 9.72 mmol) in a mixture of acetonitrile (175 ml) and CH$_2$Cl$_2$ (40 ml). The mixture was cooled to −10° C. and a solution of (BOC)$_2$O (2.54 g; 11.66 mmol) in CH$_2$Cl$_2$ (50 ml) added dropwise during 1.5 h. The mixture was stirred for a further 2.5 h at −10° C. to −5° C. Water was added and the mixture stirred overnight at room temperature. The mixture was extracted with CH$_2$Cl$_2$ and the organic phase washed with water, brine and dried over MgSO$_4$. The residue was purified by flash chromatography eluting with increasingly polar mixtures of EtOAc/CH$_2$Cl$_2$ (20 to 80% EtOAc) to give the alcohol Ea as colourless crystals (2.4 g).

Yield: 48%

$^1$H NMR spectrum (CDCl$_3$): 1.20 (s, 9H); 1.34 (s, 6H); 1.45 (m, 4H); 1.77 (m, 4H); 2.32 (s, 6H); 2.42 (t, 2H); 3.63 (m, 2H); 4.42 (s, 2H); 4.65 (s, 2H); 6.83 (s, 2H); 7.00 (s, 1H)

MS-ESI: 512 [M+H]$^+$

A solution of Ea (3.7 g; 7.23 mmol) and CBr$_4$ (3.12 g; 9.4 mmol) in CH$_2$Cl$_2$ (150 ml) was cooled to 0° C. under argon. Solid PPh$_3$ (2.84 g; 10.85 mmol) was added portionwise and the mixture allowed to warm to room temperature overnight. The mixture was directly purified by flash chromatography eluting with increasingly polar mixtures of EtOAc/CH$_2$Cl$_2$ (0 to 30% EtOAc) to give the bromide Eb as colourless crystals (3.01 g).

Yield: 73%

$^1$H NMR spectrum (DMSO d$_6$): 1.51 (s, 9H); 1.27 (s, 6H); 1.45 (m, 4H); 1.63 (m, 4H); 2.30 (s, 6H); 2.63 (t, 2H); 3.51 (t, 2H); 4.27 (s, 2H); 4.59 (s, 2H); 6.93 (s, 2H); 7.08 (s, 1H).

MS-ESI: 575 [M+H]$^+$

A mixture of Eb (150 mg; 0.26 mmol) and 1-(pyrrolidinocarbonylmethyl)piperazine (108 mg; 0.548 mmol) in acetonitrile (5 ml) under argon was heated at 80° C. for 16 h. The solvent was evaporated and the residue was purified by flash chromatography eluting with increasingly polar mixtures of MeOH/CH$_2$Cl$_2$ (0 to 7% MeOH) to give ER1 as a beige powder (161 mg).

Yield: 89%

$^1$H NMR spectrum (CDCl$_3$): 1.20 (s, 9H); 1.34 (s, 6H); 1.46 (m, 4H); 1.77 (m, 4H); 1.85 (m, 2H); 1.94 (m, 2H); 2.32 (s, 6H); 2.35-2.6 (m, 12H); 3.01 (s, 2H); 3.46 (m, 4H); 4.42 (s, 2H); 4.65 (s, 2H); 6.82 (s, 2H); 7.00 (s, 1H).

MS-ESI: 691 [M+H]$^+$

Examples 6.1-6.10

The following examples were prepared in a similar manner to Example 6,

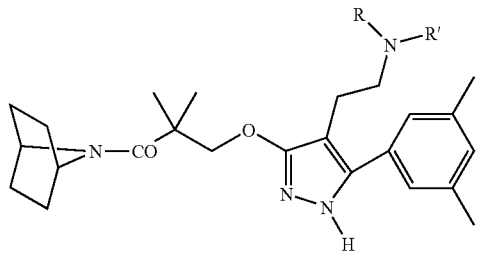

the table shows the NRR' group relating to the above structure, the reaction conditions and characteristics for each example, corresponding to the description of the preparation of Example 6 given above. The final two steps were carried out without purification or characterisation of the intermediates ER:—

Example 6.1

| —NRR' | Eb mg; mmol | Piperazine mg; mmol | Pyrrolidine ml | Mass mg; Yield | MS-ESI |
|---|---|---|---|---|---|
| 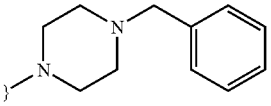 | 172; 0.3 | 116; 0.66 | 4 | 146; 85% | 570 [M + H]$^+$ |

Chromato.-Prep. LC/MS H$_2$O/MeCN buffered with ammonium carbonate at pH 8.9 (60% H$_2$O)
$^1$H NMR spectrum (DMSO d$_6$): 1.24(s, 6H); 1.41(m, 4H); 1.61(m, 4H); 2.30(s, 6H); 2.3-2.6(m, 12H); 3.43(s, 2H); 4.14(s, 2H); 4.56(s, 2H); 7.01(s, 1H); 7.10(s, 2H); 7.3(m, 5H); 11.7(s br 1H).

Example 6.2

| —NRR' | Eb mg; mmol | Piperazine mg; mmol | Pyrrolidine ml | Mass mg; Yield | MS-ESI |
|---|---|---|---|---|---|
| 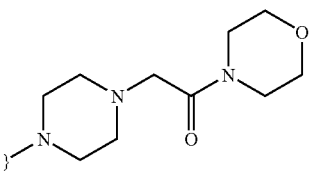 | 115; 0.2 | 94; 0.44 | 3 | 105; 87% | 607 [M + H]$^+$ |

Chromato.-Prep. LC/MS H$_2$O/MeCN buffered with ammonium carbonate at pH 8.9 (80% H$_2$O)
$^1$H NMR spectrum (DMSO d$_6$): 1.25(s, 6H); 1.42(m, 4H); 1.61(m, 4H); 2.31(s, 6H); 2.3-2.6(m, 12H); 3.10(s, 2H); 3.35-3.6(m, 8H); 4.15(s, 2H); 4.57(s, 2H); 7.02(s, 1H); 7.10(s, 2H); 11.7(s br 1H).

Example 6.3

| —NRR' | Eb mg; mmol | Piperazine mg; mmol | Pyrrolidine ml | Mass mg; Yield | MS-ESI |
|---|---|---|---|---|---|
| 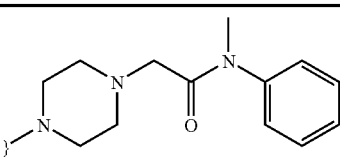 | 115; 0.2 | 103; 0.44 | 3 | 96; 77% | 627 [M + H]$^+$ |

Chromato.-Prep. LC/MS H$_2$O/MeCN buffered with ammonium carbonate at pH 8.9 (80% H$_2$O)
$^1$H NMR spectrum (DMSO d$_6$): 1.25(s, 6H); 1.42(m, 4H); 1.61(m, 4H); 2.30(s, 6H); 2.3-2.6(m, 12H); 2.85(s br, 2H); 3.15(s br, 3H); 4.14(s, 2H); 4.57(s, 2H); 7.01(s, 1H); 7.09(s, 2H); 7.32(m, 3H); 7.41(m, 2H); 11.7(s br 1H).

Example 6.4

| —NRR' | Eb mg; mmol | Piperazine mg; mmol | Pyrrolidine ml | Mass mg; Yield | MS-ESI |
|---|---|---|---|---|---|
| 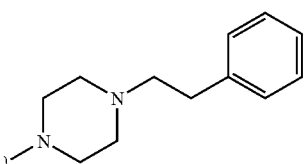 | 115; 0.2 | 84; 0.44 | 3 | 27; 25% | 584 [M + H]$^+$ |

Chromato.-Prep. LC/MS H$_2$O/MeCN buffered with ammonium carbonate at pH 8.9 (60% H$_2$O)
$^1$H NMR spectrum (DMSO d$_6$): 1.25(s, 6H); 1.42(m, 4H); 1.62(m, 4H); 2.31(s, 6H); 2.3-2.6(m, 14H); 2.70(t, 2H); 4.15(s, 2H); 4.56(s, 2H); 7.02(s, 1H); 7.11(s, 2H); 7.17(t, 1H) 7.21(d, 2H); 7.26(t, 2H); 11.7(s br 1H).

Example 6.5

| —NRR' | Eb mg; mmol | Piperazine mg; mmol | Pyrrolidine ml | Mass mg; Yield | MS-ESI |
|---|---|---|---|---|---|
| 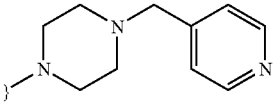 | 115; 0.2 | 78; 0.44 | 3 | 98; 86% | 571 [M + H]$^+$ |

Chromato.-Prep. LC/MS H$_2$O/MeCN buffered with ammonium carbonate at pH 8.9 (80% H$_2$O)
$^1$H NMR spectrum (DMSO d$_6$): 1.25(s, 6H); 1.41(m, 4H); 1.61(m, 4H); 2.30(s, 6H); 2.3-2.6(m, 12H); 3.48(s, 2H); 4.14(s, 2H); 4.57(s, 2H); 7.01(s, 1H); 7.10(s, 2H); 7.30(d, 2H); 8.49(dd, 2H); 11.7(s br 1H).

Example 6.6

| —NRR' | Eb mg; mmol | Piperazine mg; mmol | Pyrrolidine ml | Mass mg; Yield | MS-ESI |
|---|---|---|---|---|---|
| 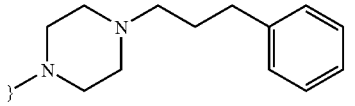 | 115; 0.2 | 90; 0.44 | 3 | 19; 16% | 598 [M + H]$^+$ |

Chromato.-Prep. LC/MS H$_2$O/MeCN buffered with ammonium carbonate at pH 8.9 (60% H$_2$O)
$^1$H NMR spectrum (DMSO d$_6$): 1.25(s, 6H); 1.42(m, 4H); 1.62(m, 4H); 1.69(m, 2H), 2.23(t, 2H); 2.30(s, 6H); 2.3-2.7(m, 14H); 4.14(s, 2H); 4.57(s, 2H); 7.01(s, 1H); 7.10(s, 2H); 7.17(m, 3H); 7.27(t, 2H); 11.7(s br 1H).

Example 6.7

| —NRR' | Eb mg; mmol | Piperazine mg; mmol | Pyrrolidine ml | Mass mg; Yield | MS-ESI |
|---|---|---|---|---|---|
| 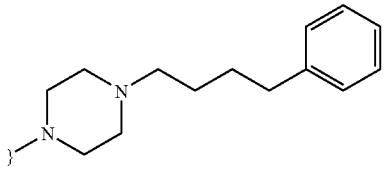 | 115; 0.2 | 96; 0.44 | 3 | 108; 88% | 612 [M + H]$^+$ |

Chromato.-Prep. LC/MS H$_2$O/MeCN buffered with ammonium carbonate at pH 8.9(60% H$_2$O)
$^1$H NMR spectrum (DMSO d$_6$): 1.25(s, 6H); 1.42(m, 6H); 1.54(m, 2H); 1.62(m, 4H); 2.23(t, 2H); 2.30(s, 6H); 2.3-2.6(m, 14H); 4.14(s, 2H); 4.57(s, 2H); 7.01(s, 1H); 7.10(s, 2H); 7.17(m, 3H); 7.27(t, 2H); 11.7(s br 1H).

Example 6.8

| —NRR' | Eb mg; mmol | Piperazine mg; mmol | Pyrrolidine ml | Mass mg; Yield | MS-ESI |
|---|---|---|---|---|---|
| 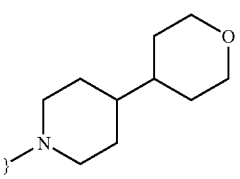 | 115; 0.2 | 75; 0.44 | 3 | 91; 81% | 563 [M + H]$^+$ |

Chromato.-Prep. LC/MS H$_2$O/MeCN buffered with ammonium carbonate at pH 8.9(80% H$_2$O)
$^1$H NMR spectrum (DMSO d$_6$): 0.99(m, 1H); 1.15(m, 3H); 1.27(s, 6H); 1.45(m, 4H); 1.55-1.65(m, 8H); 1.85(t, 2H); 2.32(s, 6H); 2.3-2.6(m, 6H); 2.88(d 2H); 3.25(t, 2H); 3.86(m, 2H); 4.16(s, 2H); 4.59(s, 2H); 7.03(s, 1H); 7.12(s, 2H); 11.86(s br 1H).

Example 6.9

| —NRR' | Eb mg; mmol | Piperazine mg; mmol | Pyrrolidine ml | Mass mg; Yield | MS-ESI |
|---|---|---|---|---|---|
| 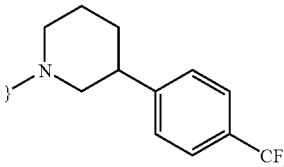 | 230; 0.4 | 223; 0.84 | 10 | 234; 94% | 623 [M + H]$^+$ |

Chromato.-MeOH/CH$_2$Cl$_2$ (0 to 10% MeOH)
$^1$H NMR spectrum (CDCl$_3$) + CD$_3$OD): 1.26(m, 6H); 1.37(m, 4H); 1.60(m, 4H); 1.71(m, 1H); 1.97(m, 2H); 2.1(m, 1H); 2.27(s, 6H); 2.8-3.0(m, 4H); 3.15(m, 2H); 3.31 m, 1H); 3.61(m, 2H); 4.14(dd, 2H); 4.47 (s, 2H); 6.96(s, 3H); 7.36(d, 2H); 7.52(d, 2H); 8.9(s br, 1H).

Example 6.10

| —NRR' | Eb mg; mmol | Piperazine mg; mmol | Pyrrolidine ml | Mass mg; Yield | MS-ESI |
|---|---|---|---|---|---|
| 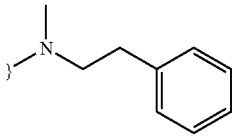 | 230; 0.4 | 113; 0.84 | 10 | 166; 79% | 529 [M + H]$^+$ |

Chromato.-MeOH/CH$_2$Cl$_2$ (0 to 10% MeOH)
$^1$H NMR spectrum (CDCl$_3$): 1.36(s, 6H); 1.43(m, 4H); 1.75(m, 4H); 2.33(s, 6H); 2.39(s, 3H); 2.6-2.8(m, 8H); 4.29(s, 2H); 4.64(s, 2H); 7.02(s, 1H); 7.05(s, 2H); 7.17(m, 3H); 7.26(m, 2H); 8.9(s br 1H).

Example 7

3-[3-(2,2-dimethyl-3-oxo-3-{azabicyclo[2.2.2]oct-2-yl}propoxy)-5-(3,5-dimethylphenyl)-1H-pyrazol-4-yl]-N-[2-(3-methoxyphenyl)ethyl]-(2S)-propylamine

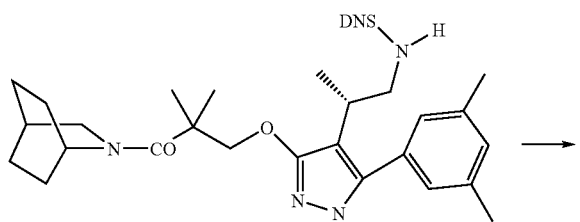

FR

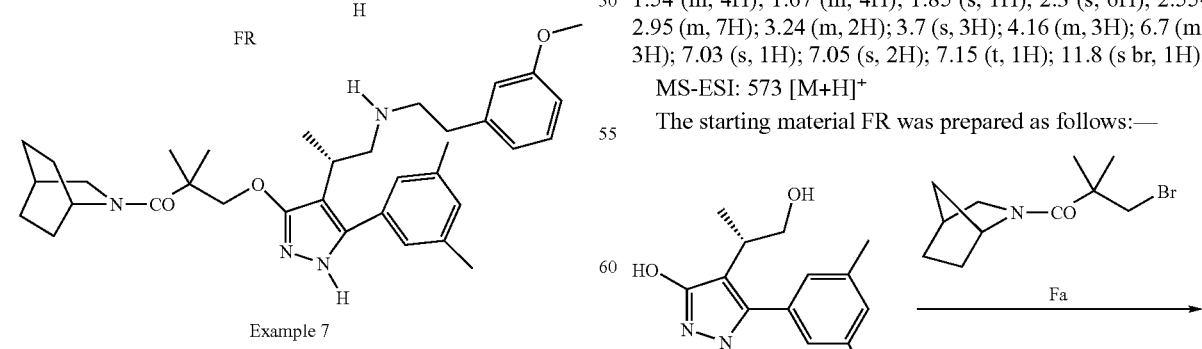

Example 7

A mixture of FR (167 mg; 0.25 mmol), 3-(2-hydroxy-ethyl)-methoxybenzene (50 mg; 0.325 mmol) and triphenylphosphine (393 mg; 1.5 mmol) in THF (5 ml) at 0° C. under argon was treated with DTAD (230 mgl; 1.0 mmol).

The mixture was allowed to warm to room temperature for 1 h when water was added. The mixture was extracted with CH$_2$Cl$_2$ and the organic phase was washed with water, brine and dried over MgSO$_4$. The residue was taken up directly in CH$_2$Cl$_2$ (3 ml) and treated dropwise with n-propylamine (150 µl; 2.5 mmol). The mixture was stirred at room temperature for 1 h and then purified directly by flash chromatography eluting with increasingly polar mixtures of CH$_2$Cl$_2$ and then MeOH/CH$_2$Cl$_2$ (0 to 10% MeOH) to give Example 7 as a white foam (100 mg).

Yield: 70%

$^1$H NMR spectrum (DMSO d$_6$): 1.15 (d, 3H); 1.27 (s, 6H); 1.54 (m, 4H); 1.67 (m, 4H); 1.85 (s, 1H); 2.3 (s, 6H); 2.55-2.95 (m, 7H); 3.24 (m, 2H); 3.7 (s, 3H); 4.16 (m, 3H); 6.7 (m, 3H); 7.03 (s, 1H); 7.05 (s, 2H); 7.15 (t, 1H); 11.8 (s br, 1H).

MS-ESI: 573 [M+H]$^+$

The starting material FR was prepared as follows:—

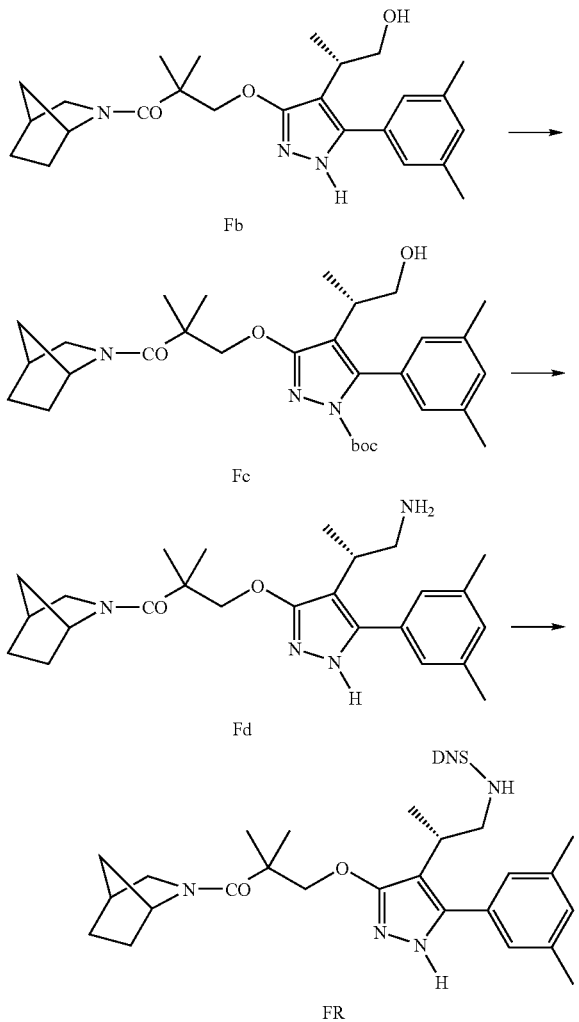

This preparation was exactly analogous to that of Examples 4 and 8

Yields and data are given in the following table:—

| Compound | Yield | MS-ESI | RMN |
|---|---|---|---|
| Fb | 85% | 440 [M+H]⁺ | ¹H NMR spectrum(CDCl₃): 1.19(d, 3H); 1.36(s, 3H); 1.41(s, 3H); 1.65(m, 6H); 1.83(m, 2H); 1.94(s, 1H); 2.23(m, 1H); 2.35(s, 6H); 3.01(m, 1H); 3.42(m, 2H); 3.69(m, 1H); 3.78(m, 1H); 4.11(m, 1H); 4.21(m, 1H); 4.41(m, 1H); 7.03(s, 1H); 7.05(s, 2H); 8.9(s br 1H). |
| Fc | 100% | 540 [M+H]⁺ | ¹H NMR spectrum(CDCl₃): 1.06(d, 3H); 1.19(s, 9H); 1.36(s, 3H); 1.42(s, 3H); 1.56(m, 6H); 1.83(m, 2H); 1.94(s, 1H); 2.25(m, 1H); 2.35(s, 6H); 2.59(m, 1H); 3.41(m, 2H); 3.57(m, 1H); 3.67(m, 1H); 4.11(m, 1H); 4.30(m, 1H); 4.60(m, 1H); 6.84(s, 2H); 7.00(s, 1H). |
| Fd | 85% | 439 [M+H]⁺ | ¹H NMR spectrum(DMSO d₆): 1.16(d, 3H); 1.27(s, 6H); 1.56(m, 4H); 1.68(m, 4H); 1.87(s, 1H); 2.31(s, 6H); 2.36(m, 2H); 2.72(m, 1H); 4.15(m, 3H); 7.02(s, 1H); 7.07(s, 2H); 8.9(s br 1H). |
| FR | 67% | 669 [M+H]⁺ | ¹H NMR spectrum(DMSO d₆): 1.10(d, 3H); 1.25(s, 6H); 1.52(m, 4H); 1.67(m, 4H); 1.83(s, 1H); 2.29(s, 6H); 2.83(m, 1H); 3.19(m, 2H); 4.13(m, 3H); 6.96(s, 2H); 6.98(s, 1H); 8.12(d, 1H); 8.51(br s, 1H); 8.52(q, 1H); 8.79(d, 1H); 11.9(s br 1H). |

A solution of Fd (1.12 g; 2.55 mmol) in CH₂Cl₂ (50 ml) was cooled to 0° C. under argon. DIEA (580 μl; 3.3 mmol) was added followed by a solution of DNOSCl (0.72 g; 2.68 mmol) in CH₂Cl₂ (10 ml). The mixture was allowed to warm to room temperature for 2 h and was treated with aq. HCl (1N). The mixture was extracted with CH₂Cl₂ and the organic phase was washed with water, brine and dried over MgSO₄. The residue was purified by flash chromatography eluting with increasingly polar mixtures of EtOAc/CH₂Cl₂ (0 to 40% EtOAc) to give FR as a yellow foam (1.14 g).

Yield: 67%

¹H NMR spectrum (DMSO d₆): 1.10 (d, 3H); 1.25 (s, 6H); 1.52 (m, 4H); 1.67 (m, 4H); 1.83 (s, 1H); 2.29 (s, 6H); 2.83 (m, 1H); 3.19 (m, 2H); 4.13 (m, 3H); 6.96 (s, 2H); 6.98 (s, 1H); 8.12 (d, 1H); 8.51 (br s, 1H); 8.52 (q, 1H); 8.79 (d, 1H); 11.9 (s br 1H).

MS-ESI: 669 [M+H]⁺

Starting material Fa was prepared as follows:—

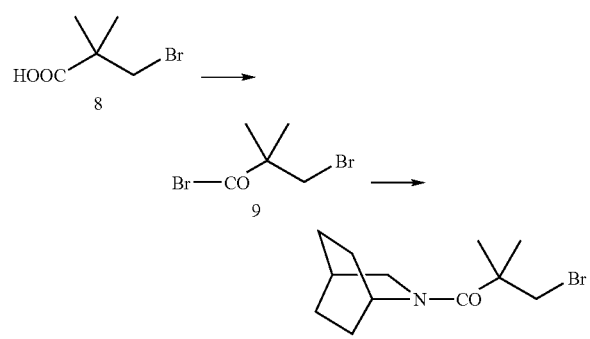

A mixture of 8 (4.0 g; 22 mmol) and oxalyl bromide (9.5 g; 44 mmol) containing one drop of DMF was heated at 50° C. for 2 h and then cooled. The excess of oxalyl bromide was evaporated and the residue azeotroped with toluene to give crude 9 which was taken up directly in CH₂Cl₂ (30 ml) and cooled to 0° C. Diisopropylethylamine (40 ml; 200 mmol) was added followed by 2.2.2-azabicyclooctane (2.95 g; 20 mmol) in CH₂Cl₂ (20 ml). The mixture was allowed to warm to room temperature overnight and was diluted with CH₂Cl₂, washed with aq. HCl (2N), aq. NaOH (1, water, brine and dried over MgSO₄. The residue was evaporated to give Fa as a beige solid (3.75 g).

Yield: 68%

¹H NMR spectrum (CDCl₃): 1.38 (s, 6H); 1.67 (m, 6H); 1.89 (m, 2H); 1.95 (s, 1H); 3.40 (m, 2H); 3.63 (s, 2H) 4.02 (s, 1H).

Example 7.1

The following example was prepared in a similar manner to Example 6,

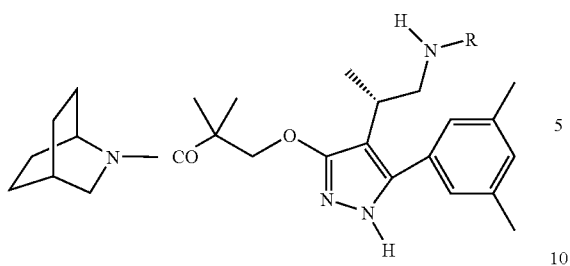

The following example was prepared in a similar manner, the table shows the NRR' group relating to the above structure, the reaction conditions and characteristics for each example, corresponding to the description of the preparation of Example 7 given above:—

Example 7.1

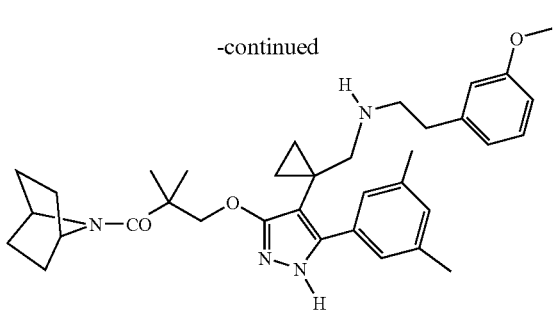

Example 8

Example 8 was prepared in a similar manner to Example 7, the table shows the reaction conditions and characteristics corresponding to the description of the preparation of Example 7 given above:—

| —NRR' | FR mg; mmol | Alcohol mg; mmol | Ph$_3$P mg; mmol | DTAD mg; mmol | nPrNH$_2$ μl; mmol | Mass mg; Yield |
|---|---|---|---|---|---|---|
| ![piperonyl] | 300; 0.45 | 150; 0.9 | 707; 2.7 | 415; 1.8 | 265; 4.5 | 193; 73% |

Chromato.-EtOAc
$^1$H NMR spectrum (DMSO d$_6$): 1.13(d, 3H); 1.27(s, 6H); 1.55(m, 4H); 1.68(m, 4H); 1.86(s, 1H); 2.3(s, 6H); 2.55-2.95(m, 7H); 3.31(m, 2H); 4.14(m, 3H); 5.93(s, 2H); 6.53(dd, 1H); 6.67(d, 1H); 6.74(d, 1H); 7.02(s, 1H); 7.05(s, 2H); 7.15(t, 1H); 11.74(s br, 1H).
MS-ESI: 587 [M + H]$^+$

Example 8

3-[2,2-dimethyl-3-oxo-3-(azabicyclo[2.2.1]heptan-7-yl)propoxy]-4-[1-(3-methoxyphenethylaminomethyl)cycloprop-1-yl]-5-(3,5-dimethylphenyl)-1H-pyrazole

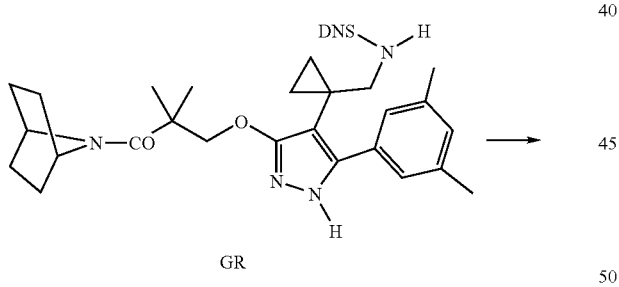

GR

| —NRR' | GR mg; mmol | Alcohol mg; mmol | Ph$_3$P mg; mmol | DTAD mg; mmol | nPrNH$_2$ μl; mmol | Mass mg; Yield |
|---|---|---|---|---|---|---|
| ![methoxyphenethyl] | 166; 0.25 | 50; 0.33 | 393; 1.5 | 230; 1.0 | 270; 10 | 68; 48% |

Chromato.-MeOH/CH$_2$Cl$_2$ (0 to 10% MeOH)
$^1$H NMR spectrum (DMSO d$_6$) : 0.42(m, 2H); 0.70(m, 2H); 1.25(s, 6H); 1.42(m, 4H); 1.62(m, 4H); 2.3(s, 6H); 2.6-2.85(m, 7H); 3.69(s, 3H); 4.14(s, 3H); 4.57(s, 2H); 6.71(m, 3H); 7.03(s, 1H); 7.15(t, 1H); 7.33(s, 2H); 11.74(s br, 1H).
MS-ESI: 571 [M + H]$^+$ Starting material GR was prepared as follows:—

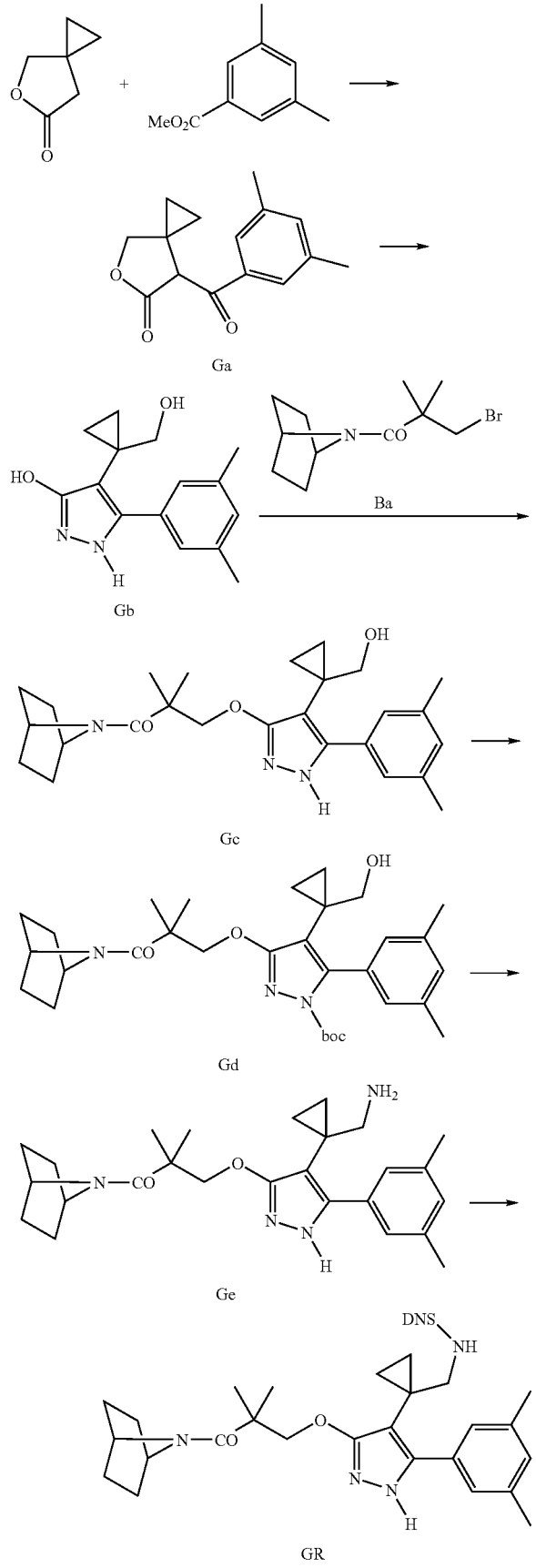

This preparation was exactly analogous to that of examples 4 and 7

Yields and data are given in the following table:—

| Compound | Yield | MS-ESI [M+H]+ | RMN |
|---|---|---|---|
| Ga | 46% | 245 | ¹H NMR spectrum(DMSO d₆): 0.47(m, 1H); 0.64(m, 1H); 0.85(m, 1H); 0.99(m, 1H); 2.35(s, 6H); 4.11(d, 1H); 4.41(d, 1H); 4.76(s, 1H); 7.36(s, 1H); 7.59(s, 2H). |
| Gb | 87% | 259 | ¹H NMR spectrum(DMSO d₆): 0.28(m, 2H); 0.72(m, 2H); 2.29(s, 6H); 3.5(s, 2H); 4.8(s br, 1H); 6.96(s, 1H); 7.34(s, 2H); 9.3(s br, 1H); 11.74(s br, 1H). |
| Gc | 69% | 438 | ¹H NMR spectrum(DMSO d₆): 0.27(m, 2H); 0.70(m, 2H); 1.27(s, 6H); 1.42(m, 4H); 1.64(m, 4H); 2.3(s, 6H); 3.43(d, 2H); 4.14(s, 2H); 4.59(s, 2H); 4.64(t, 1H); 6.99(m, 1H); 7.41(s, 2H); 11.74(s br, 1H). |
| Gd | 60% | 538 | ¹H NMR spectrum(DMSO d₆): 0.17(m, 2H); 0.46(m, 2H); 1.14(s, 9H); 1.29(s, 6H); 1.45(m, 4H); 1.65(m, 4H); 2.3(s, 6H); 3.31(d, 2H); 4.23(s, 2H); 4.59(m, 3H); 7.01(s, 2H); 7.04(s, 1H). |
| Ge | 65% | 437 | ¹H NMR spectrum(DMSO d₆): 0.35(m, 2H); 0.67(m, 2H); 1.27(s, 6H); 1.43(m, 4H); 1.64(m, 4H); 2.3(s, 6H); 2.63(d, 2H); 4.15(s, 2H); 4.58(s, 2H); 6.99(m, 1H); 7.31(s, 2H); 11.74(s br, 1H). |
| GR | 90% | 667 | ¹H NMR spectrum(DMSO d₆): 0.38(m, 2H); 0.8(m, 2H); 1.28(s, 6H); 1.42(m, 4H); 1.62(m, 4H); 2.3(s, 6H); 3.17(m, 2H); 4.14(s, 2H); 4.57(s, 2H); 6.98(m, 1H); 7.27(s, 2H); 7.98(d, 1H); 8.51(dd, 1H); 8.76(d, 1H); 11.74(s br, 1H). |

Example 9

3-[2,2-dimethyl-3-oxo-3-(azabicyclo[2.2.1]heptan-7-yl)propoxy]-4-(4-phenylpiperidin-1-ylmethyl)-5-(3,5-dimethylphenyl)-1H-pyrazole

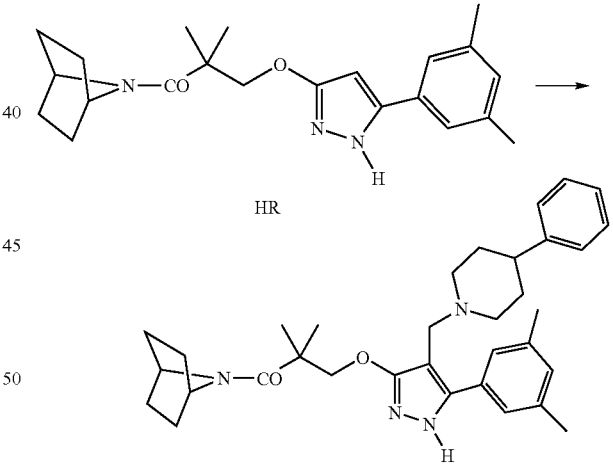

Example 9

A mixture of 4-phenyl piperidine (98 mg; 0.6 mmol) and formaldehyde (0.32 ml; 4.0 mmol; 37 wt % aqueous solution) in water (0.2 ml) and acetic acid (0.2 ml) was stirred for 5 min and treated with HR (74 mg; 0.2 mmol). The mixture was heated at 75° C. for 2 h. The solvents were evaporated, MeOH (0.5 ml), water (0.5 ml) and ammonia in MeOH(7N) (0.6 ml) were added and the mixture stirred for a further 3 h. The solvents were evaporated and the residue was purified by preparative LC/MS chromatography with H₂O/MeCN buffered with ammonium carbonate at pH 8.9 (80% H₂O) to give Example 9 as a white solid (75 mg).

Yield: 69%

¹H NMR spectrum (DMSO d₆): 1.27 (s, 6H); 1.42 (m, 4H); 1.6 (m, 6H); 1.75 (m, 2H); 2.07 (m, 2H); 2.32 (s, 6H); 2.52 (m, 1H); 2.97 (m, 2H); 3.16 (s, 2H); 4.17 (s, 2H); 4.57 (s, 2H); 7.02 (s, 1H); 7.17 (t, 1H); 7.23 (d, 2H); 7.28 (t, 2H) 12.1 (s, 1H).

MS-ESI: 541 [M+H]+

The starting material HR was prepared as follows:—

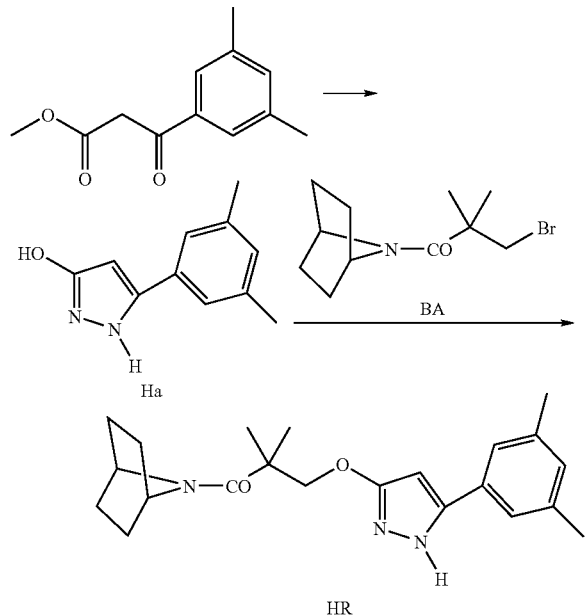

A solution of 4-(3',5'-dimethylphenyl)acetoacetate (12.36 g; 60 mmol) in EtOH (300 ml) was treated with hydrazine hydrate (5.82 ml; 120 mmol) and heated under reflux for 3 h. The EtOH was evaporated and the residue triturated with Et₂O. The precipitate was collected, washed and dried to give Ha as a white powder (9.54 g).

Yield: 85%

$^1$H NMR spectrum (DMSO d$_6$): 2.28 (s, 6H); 5.83 (s, 1H); 6.93 (s, 1H); 7.27 (s, 2H); 9.5 (s br, 1H).

MS-ESI: 189 [M+H]+

A mixture of Ha (3.1 g; 16.5 mmol) and Ba (5.15 g; 19.8 mmol) in DMA (40 ml) under argon was treated with K$_2$CO$_3$ (4.56 g; 33.0 mmol). The mixture was stirred and heated at 70° C. for 5 h. The mixture was poured into sat. aq. NaHCO$_3$, extracted with EtOAc and the organic phase was washed with water, brine and dried over MgSO$_4$. The solid residue was recrystallised from toluene to give BR as a pale yellow solid (2.96 g).

Yield: 49%

$^1$H NMR spectrum (DMSO d$_6$): 1.24 (s, 6H); 1.41 (m, 4H); 1.63 (m, 4H; 2.29 (s, 6H); 4.09 (s, 2H); 4.57 (s, 2H); 6.08 (s, 1H) 6.97 (s, 1H); 7.31 (s, 2H).

MS-ESI: 368 [M+H]+

Examples 9.1-9.12

The following examples were prepared in a similar manner to Example 9,

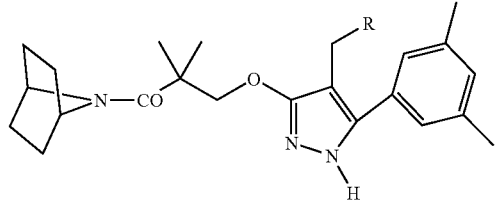

the table shows the R group relating to the above structure, the reaction conditions and characteristics for each example, corresponding to the description of the preparation of Example 9 given above:—

Example 9.1

| R | HR mg; mmol | Formaldehyde; ml; mmol | Amine mg; mmol | Prod. Form | Mass mg; Yield | MS-ESI |
|---|---|---|---|---|---|---|
| ⟩-N(piperazine)N-(CH₂)₄-Ph | 74; 0.20 | 0.25; 3.0 | 131; 0.6 | White solid | 65; 54% | 598 [M + H]+ |

Chromato.-Preparative LC/MS chromatography with H$_2$O/MeCN buffered with ammonium carbonate at pH 8.9(60% H$_2$O).
$^1$H NMR spectrum (DMSO d$_6$): 1.25(s, 6H); 1.41(m, 6H); 1.53(m, 2H); 1.58(m, 4H); 2.29(s, 6H); 2.3-2.65(m, 12H); 3.01(s, 2H); 4.15(s, 2H); 4.56(s, 2H); 7.00(s, 1H); 7.17(m, 3H); 7.25(m, 2H); 7.44(s, 2H); 11.9(s br, 1H).

Example 9.2

| R | HR mg; mmol | Formaldehyde; ml; mmol | Amine mg; mmol | Prod. Form | Mass mg; Yield | MS-ESI |
|---|---|---|---|---|---|---|
| MeN(CH₂)₃Ph | 148; 0.40 | 0.32; 4.0 | 270; 2.0 | White solid | 81; 39% | 529 [M + H]+ |

Chromato.-Preparative LC/MS chromatography with H$_2$O/MeCN buffered with ammonium carbonate at pH 8.9(60% H$_2$O).
$^1$H NMR spectrum (DMSO d$_6$): 1.23(s, 6H); 1.41(m, 4H); 1.60(m, 4H); 1.73(m, 2H); 2.1(s, 3H); 2.27(s, 6H); 2.35(m, 2H) 2.5-2.7(m, 2H); 3.14(s, 2H); 4.14(s, 2H); 4.56(s, 2H); 6.99(s, 1H); 7.12(m, 3H); 7.23(m, 2H); 7.44(s, 2H); 11.9(s br, 1H).

Example 9.3

| R | HR mg; mmol | Formaldehyde; ml; mmol | Amine mg; mmol | Prod. Form | Mass mg; Yield | MS-ESI |
|---|---|---|---|---|---|---|
| 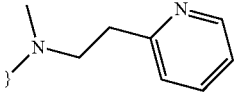 | 80; 0.20 | 0.25; 3.0 | 82; 0.6 | White solid | 27; 26% | 516 [M + H]$^+$ |

Chromato.-Preparative LC/MS chromatography with H$_2$O/MeCN buffered with ammonium carbonate at pH 8.9 (100 to 0% H$_2$O).

Example 9.4

| R | HR mg; mmol | Formaldehyde; ml; mmol | Amine mg; mmol | Prod. Form | Mass mg; Yield | MS-ESI |
|---|---|---|---|---|---|---|
| 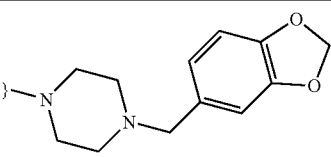 | 80; 0.20 | 0.25; 3.0 | 132; 0.6 | White solid | 26; 22% | 600 [M + H]$^+$ |

Chromato.-Preparative LC/MS chromatography with H$_2$O/MeCN buffered with ammonium carbonate at pH 8.9(100 to 0% H$_2$O).

Example 9.5

| R | HR mg; mmol | Formaldehyde; ml; mmol | Amine mg; mmol | Prod. Form | Mass mg; Yield | MS-ESI |
|---|---|---|---|---|---|---|
| 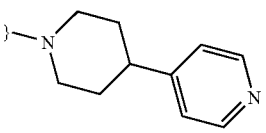 | 80; 0.20 | 0.25; 3.0 | 97; 0.6 | White solid | 37; 34% | 542 [M + H]$^+$ |

Chromato.-Preparative LC/MS chromatography with H$_2$O/MeCN buffered with ammonium carbonate at pH 8.9(100 to 0% H$_2$O).

Example 9.6

| R | HR mg; mmol | Formaldehyde; ml; mmol | Amine mg; mmol | Prod. Form | Mass mg; Yield | MS-ESI |
|---|---|---|---|---|---|---|
| 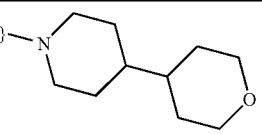 | 80; 0.20 | 0.25; 3.0 | 102; 0.6 | White solid | 21; 19% | 549 [M + H]$^+$ |

Chromato.-Preparative LC/MS chromatography with H$_2$O/MeCN buffered with ammonium carbonate at pH 8.9(100 to 0% H$_2$O).

Example 9.7

| R | HR mg; mmol | Formaldehyde; ml; mmol | Amine mg; mmol | Prod. Form | Mass mg; Yield | MS-ESI |
|---|---|---|---|---|---|---|
| 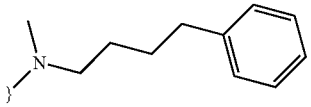 | 148; 0.40 | 0.16; 2.0 | 298; 2.0 | White solid | nd*; nd* | 543 [M + H]$^+$ |

Chromato.-Preparative LC/MS chromatography with $H_2O$/MeCN buffered with ammonium carbonate at pH 8.9(60% $H_2O$).
$^1$H NMR spectrum (DMSO $d_6$): 1.24(s, 6H); 1.42(m, 6H); 1.54(m, 2H); 1.61(m, 4H); 2.06(s, 3H); 2.25(s, 6H); 2.31(m, 2H); 2.5-2.65(m, 2H); 3.12(s, 2H); 4.16(s, 2H); 4.56(s, 2H); 6.98(s, 1H); 7.13(m, 3H); 7.22(m, 2H); 7.42(s, 2H); 11.9(s br, 1H).

Example 9.8

| R | HR mg; mmol | Formaldehyde; ml; mmol | Amine mg; mmol | Prod. Form | Mass mg; Yield | MS-ESI |
|---|---|---|---|---|---|---|
| 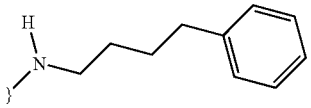 | 148; 0.40 | 0.16; 2.0 | 298; 2.0 | gum | nd*; nd* | 529 [M + H]$^+$ |

Chromato.-Preparative LC/MS chromatography with $H_2O$/MeCN buffered with ammonium carbonate at pH 8.9(60% $H_2O$).
$^1$H NMR spectrum (DMSO $d_6$): 1.24(s, 6H); 1.42(m, 6H); 1.57(m, 6H); 2.28(s, 6H); 2.5-2.6(m, 4H); 3.45(s, 2H); 4.16 (s, 2H); 4.55(s, 2H); 6.99(s, 1H); 7.14(m, 3H); 7.25(m, 2H); 7.30(s, 2H); 11.9(s br, 1H).

Example 9.9

| R | HR mg; mmol | Formaldehyde; ml; mmol | Amine mg; mmol | Prod. Form | Mass mg; Yield | MS-ESI |
|---|---|---|---|---|---|---|
| 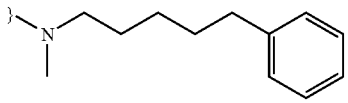 | 74; 0.20 | 0.08; 1.0 | 253; 1.0 | gum | 26; 24% | 543 [M + H]$^+$ |

Chromato.-Preparative LC/MS chromatography with $H_2O$/MeCN buffered with ammonium carbonate at pH 8.9(80% $H_2O$).
$^1$H NMR spectrum (DMSO $d_6$): 1.24(s, 6H); 1.29(m, 2H); 1.42(m, 6H); 1.53(m, 2H); 1.57(m, 4H); 2.29(s, 6H); 2.5-2.6(m, 4H); 3.46(s, 2H); 4.16(s, 2H); 4.56(s, 2H); 7.01(s, 1H); 7.15(m, 3H); 7.25(m, 2H); 7.30(s, 2H); 11.9(s br, 1H).

Example 9.10

| R | HR mg; mmol | Formaldehyde; ml; mmol | Amine mg; mmol | Prod. Form | Mass mg; Yield | MS-ESI |
|---|---|---|---|---|---|---|
| 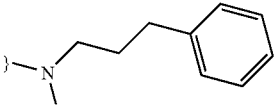 | 74; 0.20 | 0.08; 1.0 | 162; 1.2 | White solid | 42; 20% | 529 [M + H]$^+$ |

Chromato.-Preparative LC/MS chromatography with $H_2O$/MeCN buffered with ammonium carbonate at pH 8.9 (80% $H_2O$).
$^1$H NMR spectrum (DMSO $d_6$): 1.24(s, 6H); 1.41(m, 4H); 1.59(m, 4H); 1.69(m, 2H); 2.29(s, 6H); 2.3-2.65(m, 4H); 3.45(s, 2H); 4.16(s, 2H); 4.56(s, 2H); 7.01(s, 1H); 7.157(m, 3H); 7.23(m, 2H); 7.31(s, 2H); 11.9(s br, 1H).

Example 9.11

| R | HR mg; mmol | Formaldehyde; ml; mmol | Amine mg; mmol | Prod. Form | Mass mg; Yield | MS-ESI |
|---|---|---|---|---|---|---|
| 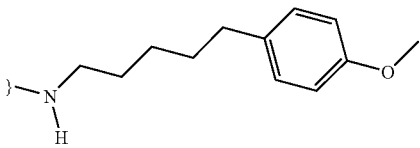 | 74; 0.20 | 0.08; 1.0 | 232; 1.2 | gum | 47; 41% | 573 [M + H]$^+$ |

Chromato.-Preparative LC/MS chromatography with H$_2$O/MeCN buffered with ammonium carbonate at pH 8.9(60% H$_2$O).
$^1$H NMR spectrum (DMSO d$_6$): 1.24(s, 6H); 1.28(m, 2H); 1.41(m, 6H); 1.49(m, 2H); 1.60(m, 4H); 2.30(s, 6H); 2.3-2.65(m, xH); 3.44 (s, 2H); 3.70(s, 3H); 4.16(s, 2H); 4.56(s, 2H); 6.81(d, 2H); 7.01(s, 1H); 7.04(d, 2H); 7.30(m, 2H); 11.9(s br, 1H).

Example 9.12

| R | HR mg; mmol | Formaldehyde; ml; mmol | Amine mg; mmol | Prod. Form | Mass mg; Yield | MS-ESI |
|---|---|---|---|---|---|---|
| 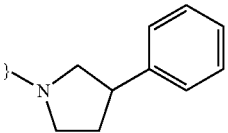 | 74; 0.20 | 0.08; 3.0 | 97; 0.6 | White solid | 74; 69% | 541 [M + H]$^+$ |

Chromato.-Preparative LC/MS chromatography with H$_2$O/MeCN buffered with ammonium carbonate at pH 8.9(60% H$_2$O).
$^1$H NMR spectrum (DMSO d$_6$): 1.34(m, 6H); 1.45(m, 5H); 1.75(m, 4H); 1.9(m, 1H); 2.31(m, 1H); 2.35(s, 6H); 2.5(m, 1H); 2.59(m, 2H); 2.68(m, 3H); 3.39(dd, 2H); 4.28(s, 2H); 4.65(s, 2H); 7.02(s, 1H); 7.16(m, 3H); 7.25(m, 2H); 7.34(s, 2H); 8.9(s br, 1H).

Example 10

2-[3-(2,2-dimethyl-3-{azabicyclo[2.2.1]heptan-7-yl}propoxy)-5-(3,5-dimethylphenyl)-1H-pyrazol-4-yl]-N-[2-(1,3-benzodioxol-5-yl)ethyl]-(2S)-propylamine

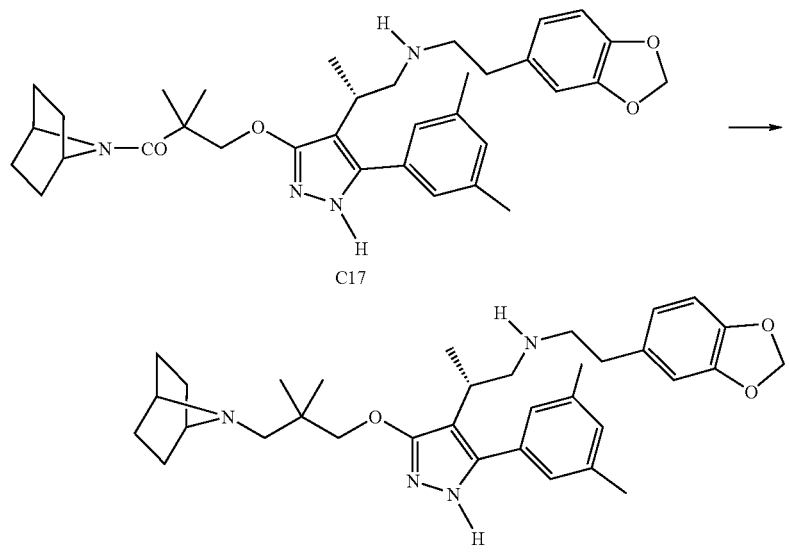

Example 10

A solution of Example 4 (123 mg; 0.21 mmol) in THF (3 ml) under argon was treated with a solution of LiAlH₄ (420 μl; 0.42 mmol; 1M solution in THF). The mixture was heated at 60° C. for 1 h. The mixture was treated with an excess of Glaubers' Salt (Na₂SO₄. 10H₂O), filtered and evaporated. The residue was purified by flash chromatography eluting with increasingly polar mixtures of MeOH/CH₂Cl₂ (5 to 15% MeOH) to give Example 10 as a white solid (80 mg).

Yield: 68%

¹H NMR spectrum (DMSO d₆): 0.93 (s, 6H); 1.18 (d, 3H); 1.2 (m, 4H); 1.59 (m, 4H); 2.19 (s, 2H); 2.3 (s, 6H); 2.55-2.95 (m, 7H); 3.07 (s, 2H); 3.86 (s, 2H); 5.94 (s, 2H); 6.53 (d, 1H); 6.66 (s, 1H); 6.74 (d, 1H); 7.04 (s, 1H); 7.05 (s, 2H); 11.7 (s br 1H).

MS-ESI: 559 [M+H]⁺

Example 11

2-[3-(2,2-dimethyl-3-hydroxypropoxy)-5-(3,5-dimethylphenyl)-1H-pyrazol-4-yl]-N-[2-(1,3-benzodioxol-5-yl)ethyl]-(2S)-propylamine

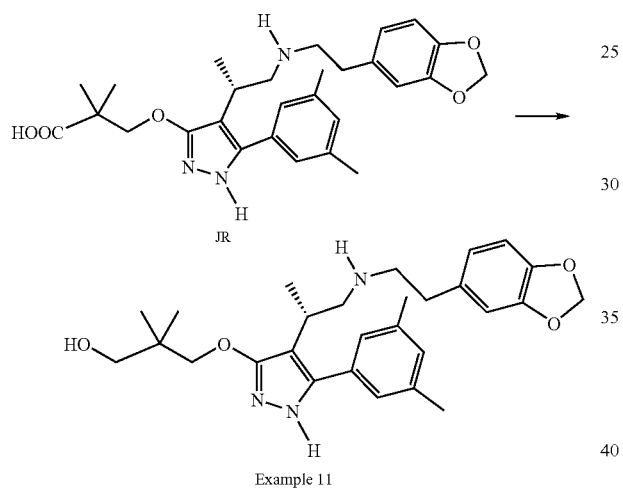

A solution of JR (109 mg; 0.17 mmol) in THF (2 ml) under argon was treated with a solution of LiAlH₄ (350 ul; 0.35 mmol; 1M solution in THF). The mixture was heated at 60° C. for 1 h. The mixture was treated with an excess of Glaubers Salt (Na₂SO₄.10H₂O), filtered and evaporated. The residue was purified by flash chromatography eluting with increasingly polar mixtures of MeOH/CH₂Cl₂ (0 to 15% MeOH) to give Example 11 as a white solid (68 mg).

Yield: 84%

¹H NMR spectrum (DMSO d₆): 0.92 (s, 6H); 1.17 (d, 3H); 2.3 (s, 6H); 2.5-2.9 (m, 7H); 3.27 (s, 2H); 3.86 (s, 2H); 4.61 (t br, 1H); 5.94 (s, 2H); 6.53 (d, 1H); 6.67 (s, 1H); 6.74 (d, 1H); 7.03 (s, 1H); 7.04 (s, 2H); 11.7 (s br 1H).

MS-ESI: 480 [M+H]⁺

Starting material JR was prepared as follows:—

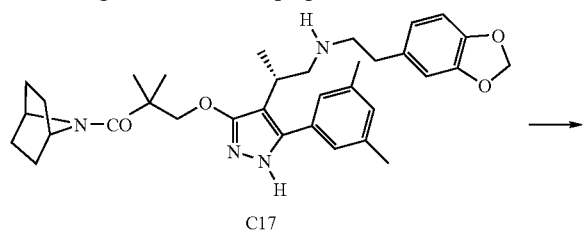

C17

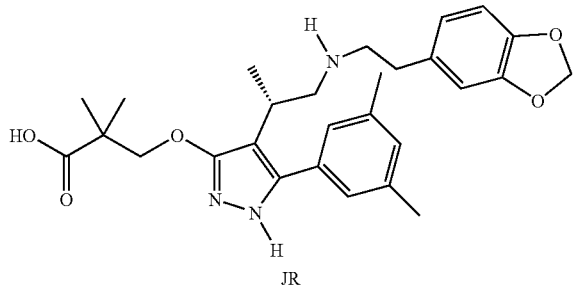

JR

A solution of Example 4 (205 mg; 0.35 mmol) in acetonitrile (2 ml) was treated with c.HCl (1 ml) and the mixture was stirred at room temperature for 2 h. The mixture was concentrated, extrated with CH₂Cl₂ and the organic phase was washed with water, brine and dried over MgSO₄. The residue a was obtained as a yellow solid (218 mg). It was used directly in the final step of the synthesis of Example 11.

Yield: 80%

¹H NMR spectrum (DMSO 4): 1.24 (m, 9H); 2.33 (s, 6H); 2.78 (m, 2H); 2.95 (m, 2H); 3.14 (m, 3H); 4.13 (m, 2H); 5.98 (s, 2H); 6.62 (d, 1H); 6.76 (s, 1H); 6.84 (d, 1H); 7.05 (s, 2H); 7.07 (s, 2H); 8.6 (s br, 1H); 11.7 (s br 1H).

MS-ESI: 494 [M+H]⁺

Example 12

2-[3-(2,2-dimethyl-3-oxo3-isopropoxy-propoxy)-5-(3,5-ditnethylphenyl)-1H-pyrazol-4-yl]-N-[2-(1,3-benzodioxol-5-yl)ethyl]-(2S)-propylamine

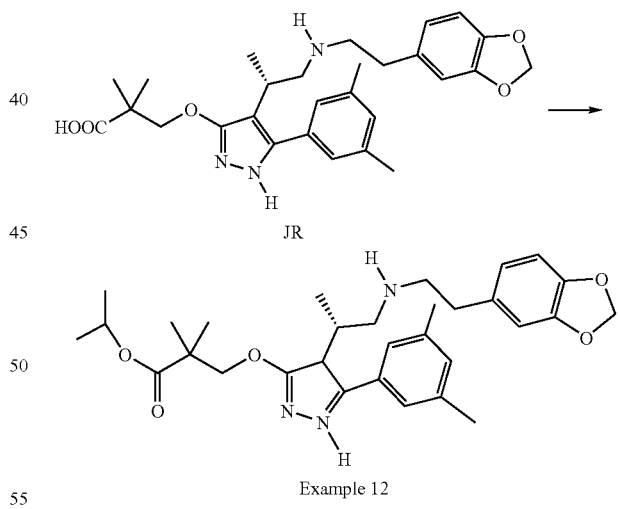

A solution of JR (109 mg; 0.17 mmol) in CH₂Cl₂ (1 ml) was added to a solution of EDCl (37 mg; 0.19 mmol) and DMAP (5 mg; cat.) in iPrOH (5 ml). H₂SO₄ (5 drops; cat.) was added and the mixture was heated under reflux overnight over molecular sieves. The mixture was concentrated and extracted with CH₂Cl₂/water and the organic phase was washed with water, brine and dried over MgSO₄. The residue was purified by flash chromatography eluting with increasingly polar mixtures of MeOH(CH₂Cl₂ (0 to 10% MeOH) to give Example 12 as a yellow gum (59 mg).

Yield: 65%

$^1$H NMR spectrum (DMSO d$_6$): 1.16 (m, 6H); 1.24 (m, 9H); 2.32 (s, 6H); 2.8 (m, 2H); 2.95 (m, 2H); 3.15 (m, 3H); 4.16 (dd, 2H); 4.88 (m, 1H); 5.98 (s, 2H); 6.62 (d, 1H); 6.74 (s, 1H); 6.83 (d, 1H); 7.04 (s, 2H); 7.07 (s, 2H); 11.7 (s br 1H).

MS-ESI: 536 [M+H]$^+$

Therapeutic Uses

Compounds of Formula (I) are provided as medicaments for antagonising gonadotropin releasing hormone (GnRH) activity in a patient, eg, in men and/or women. To this end, a compound of Formula (I) can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of uroidnase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-floated like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay Using Rat Pituitary GnRH Receptor

The assay is performed as follows:—

1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.

2. Rapidly filter and repeatedly wash through a glass fibre filter.

3. Determine the radioactivity of membrane bound radioligands using a gamma counter.

From this data, the IC$_{50}$ of the test compound can be determined as the concentration of the compound required to inhibit radio-ligand binding to GnRH receptors by 50%.

Compounds according to the present invention have activity at a concentration from 1 nM to 5 μM.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150-200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS).

The glands are further processed by:—
1. Centrifugation at 250×g for 5 minutes;
2. Aspiration of the HBSS solution;
3. Transfer of the glands to a petri dish before mincing with a scalpel;
4. Transfer of the minced tissue to a centrifuge tube by suspending the tissue three successive times in 10 ml aliquots of IBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;
8. Re-suspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase;
10. Pooling of the cell suspensions and dilution to a concentration of $3\times10^5$ cells/ml;
11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 µM.

The invention claimed is:

1. A compound 2-[3-(2,2-dimethyl-3-oxo-3-{azabicyclo[2.2.1]heptan-7-yl}propoxy)-5-(3,5-dimethyiphenyl)-1H-pyrazol-4-yl]-N-[2-(1,3-benzodioxol-5-yl)ethyl]-(2S)-propylamine or a salt, or in-vivo hydrolyzable ester thereof.

2. A pharmaceutical formulation comprising a compound, or salt, or in-vivo hydrolyzable ester thereof, according to claim 1 and a pharmaceutically acceptable diluent or carrier.

3. A method of antagonising gonadotropin releasing hormone activity in a patient, the method comprising administering a compound, or salt, or in-vivo hydrolysable ester thereof, according to claim 1 to a patient.

4. A process for the preparation of a compound of Formula (I) as defined in claim 1, comprising a process selected from (a) to (h) as follows:

(a) Reaction of a compound of formula XXXII with a compound of formula H—$R^{5'}$ to form a compound of Formula (I),

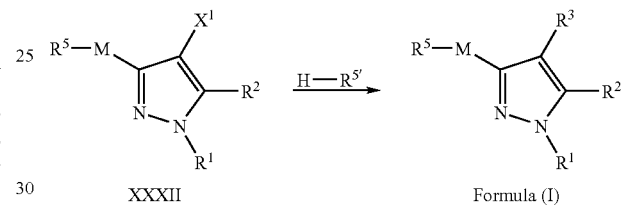

wherein $X^1$ is selected from:

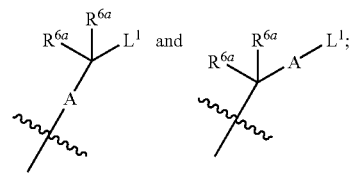

$L^1$ is a displaceable group; and
H—$R^{5'}$ is selected from:

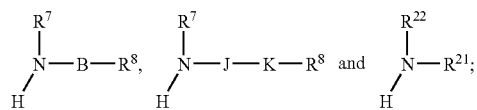

(b) Reaction of a compound of formula XXXIII with a compound of formula H—$R^{5''}$ to form a compound of Formula (I),

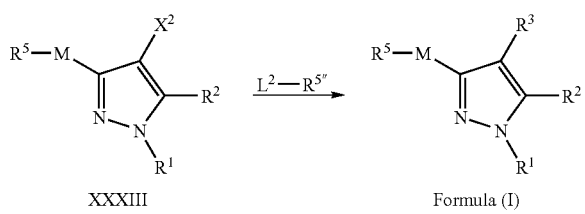

wherein $X^2$ is selected from:

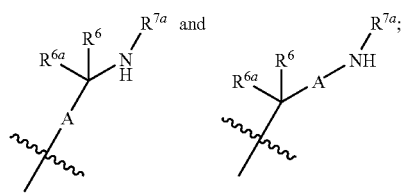

$L^2$ is a displaceable group and $R^{7a}$ is selected from the definition of $R^7$ or $R^{22}$ above, and
$L^2$-$R^{5'''}$ is selected from:
$L^2$-B—$R^8$, $L^2$-J-K—$R^8$ and $L^2$-$R^{21}$ (c) For compounds of Formula (I) wherein $R^3$ is a group of Formula (IIa), (IIb), (IIc) or (IId) and $R^7$ is other than part of a heterocyclic ring or hydrogen, reaction of a compound of Formula (I) wherein $R^3$ is a group of Formula (IIa), (IIb), (IIc) or (IId) and $R^7$ is hydrogen with a group of formula $L^3$-$R^{7a}$, wherein $R^{7a}$ is as defined above for $R^7$ with the exclusion of hydrogen and $L^3$ is a displaceable group;

(d) For compounds of Formula (I) wherein $R^3$ is a group of Formula (IIe) or (IIf) and $R^{21}$ is other than hydrogen, reaction of a compound of Formula (I) wherein $R^3$ is a group of Formula (IIe) or (IIf) and $R^{21}$ is hydrogen with a group of formula $L^4$-$R^{21a}$, wherein $R^{21a}$ is as defined above for $R^{21}$ with the exclusion of hydrogen and $L^4$ is a displaceable group;

(e) For compounds of Formula (I) wherein $R^3$ is a group of Formula (IIe) or (IIf) and $R^{22}$ is other than hydrogen, reaction of a compound of Formula (I) wherein $R^3$ is a group of Formula (IIe) or (IIf) and $R^{22}$ is hydrogen with a group of formula $L^5$-$R^{22a}$, wherein $R^{22a}$ is as defined above for $R^{22}$ with the exclusion of hydrogen and $L^5$ is a displaceable group;

(f) For compounds of Formula (I) wherein $R^3$ is a group of Formula (IIc) or (IId) and the group

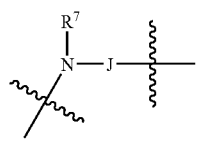

together forms an optionally substituted nitrogen-containing heterocyclic ring containing 4-7 carbons atoms, reaction of a compound of Formula XXXIVa or XXXIVb, with a compound of Formula $L^6$-K—$R^8$, wherein $L^3$ is a displaceable group

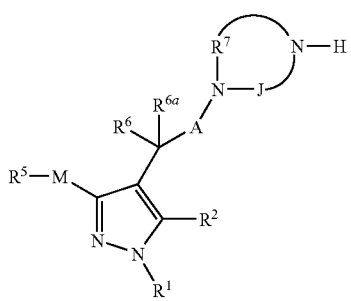
XXXIVa

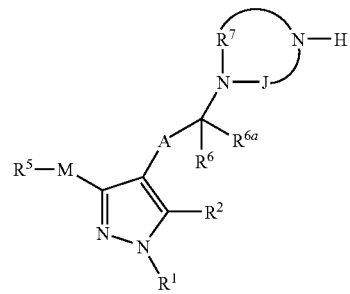
XXXIVb (g) For compounds of Formula (I) wherein $R^3$ is a group of Formula (IIc) or (IId), reaction of a compound of Formula XXXVa or XXXVb, with a compound of Formula $L^7$-K''—$R^8$, wherein $L^7$ is a displaceable group, and wherein the groups K' and K'' comprise groups which when reacted together form K,

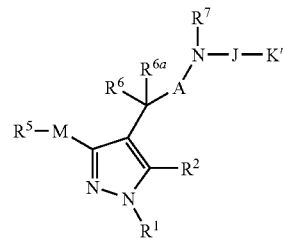
XXXVa

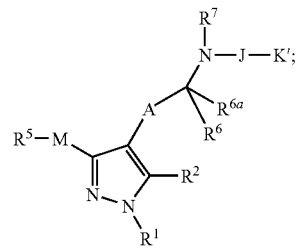
XXXVb (h) reaction of a compound of Formula XXXVI with a compound of the formula $L^8$-$R^5$, wherein $L^8$ is a displaceable group

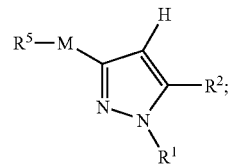
XXXVI and thereafter if necessary:
i) converting a compound of the Formula (I) into another compound of the Formula (I);
ii) removing any protecting groups;
iii) forming a salt, or in-vivo hydrolyzable ester.

5. A compound of Formula (I),

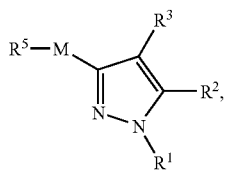

Formula (I)

or a salt, or in-vivo hydrolyzable ester thereof, wherein
$R^1$ hydrogen;
$R^2$ is 3,5-dimethylphenyl;
M is —$CH_2$—O—;
$R^5$ is 2,2-dimethyl-3-oxo-3-{azabicyclo[2.2.1]heptan-7-yl}propoxy;
$R^3$ is Formula (IIb),

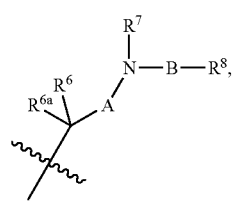

Formula (IIb)

wherein,
$R^6$ is hydrogen;
$R^{6a}$ is methyl;
$R^7$ is hydrogen;
$R^8$ is 1,3-benzodioxol-5-yl;
A is methylene; and
B is selected from ethylene and butylene.

6. A compound of Formula (I),

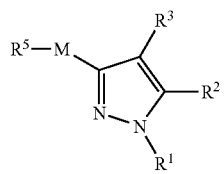

Formula (I)

wherein
$R^1$ is selected from: hydrogen, optionally-substituted $C_{1-6}$alkyl, optionally substituted aryl or optionally-substituted aryl$C_{1-6}$alkyl;
$R^2$ is optionally-substituted phenyl;
$R^3$ is selected from a group of Formula (IIa) to Formula (IIf):

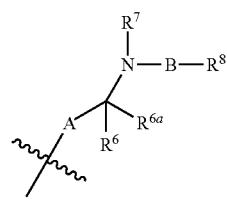

Formula (IIa)

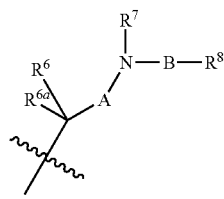

Formula (IIb)

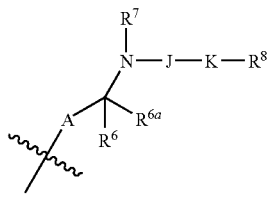

Formula (IIc)

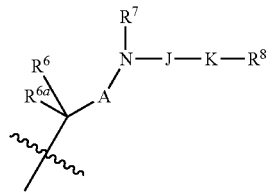

Formula (IId)

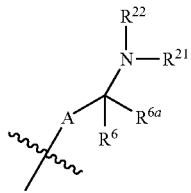

Formula (IIe)

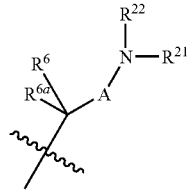

Formula (IIf)

$R^5$ is a group of Formula (III):

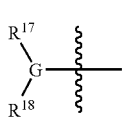

Formula (III)

$R^1$ and $R^{6a}$ are independently selected from hydrogen, fluoro, optionally substituted $C_{1-6}$alkyl or $R^6$ and $R^{6a}$ taken together and the carbon atom to which they are attached form a carbocyclic ring of 3-7 atoms
$R^7$ is selected from: hydrogen, optionally-substituted $C_{1-6}$alkyl, optionally-substituted aryl$C_{1-6}$alkyl, optionally-substituted aryl, optionally substituted heterocyclyl, optionally substituted heterocyclyl$C_{1-6}$alkyl, $R^9OC_{1-6}$alkyl-, $R^9R^{10}NC_{1-6}$alkyl-, $R^9R^{10}NC(O)C_{1-6}$alkyl, —C($NR^9R^{10}$)=NH;
or when $R^3$ is a group of Formula (IIc) or (IId) $R^7$ is of the formula -J-K—R;
$R^8$ is selected from:
(i) hydrogen, $C_{1-6}$alkyl, $C_{2-6}$alkenyl, $C_{2-6}$alkynyl, halo$C_{1-6}$alkyl, $C_{1-4}$alkoxy$C_{1-4}$alkyl, hydroxy, hydroxy$C_{1-6}$alkyl, cyano, N—$C_{1-4}$alkylamino, N,N-di-$C_{1-4}$alkylamino, $C_{1-6}$alkyl-$S(O_n)$—, —O—$R^b$, $NR^bR^c$, —C(O)—$R^b$, —C(O)O—$R^b$, —$CONR^bR^c$, NH—C(O)—$R^b$ or —$S(O_n)NR^bR^c$, where $R^b$ and $R^c$ are independently selected from hydrogen and $C_{1-4}$alkyl optionally substituted with hydroxy, amino, N—$C_{1-4}$alkylamino, N,N-di-$C_{1-4}$alkylamino, HO—$C_{2-4}$alkyl-NH— or HO—$C_{2-4}$alkyl-N($C_{1-4}$alkyl)-;

(ii) nitro when B is a group of Formula (IV) and X is CH and p is 0;

(iii) $C_{3-7}$cycloalkyl, aryl or aryl$C_{1-6}$alkyl each of which is optionally substituted by $R^{12}$, $R^{13}$ and $R^{14}$;

(iv) -(Q)-aryl, -(Q)-heterocyclyl, -aryl-(Q)-aryl, each of which is optionally substituted by $R^{12}$, $R^{13}$ and $R^{14}$ wherein -(Q)- is selected from E, F or a direct bond;

(v) heterocyclyl or heterocyclyl$C_{1-6}$alkyl each of which is optionally substituted by up to 4 substituents independently selected from $R^{12}$, $R^{13}$ and $R^{14}$;

(vi) a group selected from $R^{12}$, $R^{13}$ and $R^{14}$;

$R^9$ and $R^{10}$ are independently selected from: hydrogen, hydroxy, optionally substituted $C_{1-6}$alkyl, optionally substituted aryl, optionally substituted aryl$C_{1-6}$alkyl, an optionally substituted carbocyclic ring of 3-7 atoms, optionally substituted heterocyclyl, optionally substituted heterocyclyl$C_{1-6}$alkyl or $R^9$ and $R^{10}$ taken together can form an optionally substituted ring of 3-9 atoms or $R^9$ and $R^{10}$ taken together with the carbon atom to which they are attached form a carbonyl group;

$R^{11}$ is selected from: hydrogen, optionally substituted $C_{1-6}$alkyl, or $N(R^9R^{10})$;

$R^{12}$ is selected from: hydrogen, hydroxy, $R^{17}R^{18}N(CH_2)_{cc}$—, $R^{17}R^{18}NC(O)(CH_2)_{cc}$—, optionally substituted $C_{1-6}$alkyl-$C(O)N(R^9)(CH_2)_{cc}$—, optionally substituted $C_{1-6}$alkyl-$SO_2N(R^9)$—, optionally substituted aryl-$SO_2N(R^9)$—, $C_{1-3}$perfluoroalkyl-$SO_2N(R^9)$—; optionally substituted $C_{1-6}$alkyl-$N(R^9)SO_2$—, optionally substituted aryl-$N(R^9)SO_2$—, $C_{1-3}$perfluoroalkyl-N$(R^9)SO_2$— optionally substituted $C_{1-6}$alkanoyl-$N(R^9)SO_2$—; optionally substituted aryl-$C(O)N(R^9)SO_2$—, optionally substituted $C_{1-6}$alkyl-$S(O_n)$—, optionally substituted aryl-$S(O_n)$—, $C_{1-3}$perfluoroalkyl-, $C_{1-3}$perfluoroalkoxy, optionally substituted $C_{1-6}$alkoxy, carboxy, halo, nitro or cyano;

$R^{13}$ and $R^{14}$ are independently selected from: hydrogen, hydroxy, oxo, optionally substituted $C_{1-6}$alkyl, optionally substituted $C_{1-6}$alkanoyl, optionally substituted $C_{2-6}$alkenyl, cyano, nitro, $C_{1-3}$perfluoroalkyl-, $C_{1-3}$perfluoroalkoxy, optionally substituted aryl, optionally substituted aryl $C_{1-6}$alkyl, $R^9O(CH_2)_s$—, $R^9(O)O(CH_2)_s$—, $R^9OC(O)(CH_2)_s$—, $R^{16}S(O_n)(CH_2)_s$—, $R^9R^{10}NC(O)(CH_2)_s$— or halo;

$R^{15}$ is selected from: hydrogen, optionally substituted $C_{1-6}$alkyl, $R^{19}OC(O)$—, $R^9R^{10}NC(O)$—, $R^9C(O)$—, $R^9S(O_n)$—;

$R^{16}$ is selected from: hydrogen, $C_{1-6}$alkyl, $C_{1-3}$perfluoroalkyl or optionally-substituted aryl;

$R^{17}$ is independently selected from: hydrogen, hydroxy, cyano or optionally substituted $C_{1-6}$alkyl;

$R^{18}$ is a group of formula $R^{18a}$—$C(R^9R^{10})_{0-1}$— wherein $R^{18a}$ is selected from: $R^{19}OC(O)$—, $R^9R^{10}NC(O)$—, $R^9R^{10}N$—, $R^9C(O)$—, $R^9C(O)N(R^{10})$—, $R^9R^{10}NC(O)$—, $R^9R^{10}NC(O)N(R^{10})$—, $R^9SO_2N(R^{10})$—, $R^9R^{10}NSO_2N(R^{10})$—, $R^9C(O)O$—, $R^9OC(O)$—, $R^9R^{10}NC(O)O$—, $R^9O$—, $R^9S(O_n)$—, $R^9R^{10}NS(O_n)$—, hydrogen, optionally substituted $C_{1-6}$alkyl, optionally substituted heterocyclyl;

or $R^{17}$ and $R^{18}$ when taken together form an optionally substituted carbocyclic ring of 3-7 atoms or optionally substituted heterocyclyl;

$R^{19}$ is selected from: hydrogen, optionally substituted $C_{1-6}$alky, optionally substituted aryl, optionally substituted aryl$C_{1-6}$alkyl, optionally substituted $C_{3-7}$cycloalkyl, optionally substituted heterocyclyl or optionally substituted heterocyclyl$C_{1-6}$alkyl;

$R^{21}$ and $R^{22}$ are independently selected from hydrogen, optionally substituted $C_{1-6}$alkyl, optionally substituted $C_{3-7}$cycloalkyl, optionally substituted heterocyclyl, optionally substituted heterocyclyl$C_{1-6}$alkyl, optionally substituted $C_{3-6}$alkenyl, optionally substituted $C_{3-6}$alkynyl, —$(C_{1-5}alkyl)_{aa}$-$S(O_n)$—$(C_{1-5}alkyl)_{bb}$-; $R^9R^{10}NC_{2-6}$alkyl, $R^9OC_{2-6}$alkyl or $R^9R^{10}NC(O)C_{2-6}$alkyl, with the proviso that $R^9$ and $R^{10}$ independently or taken together are not optionally substituted aryl or optionally substituted aryl$C_{1-6}$alkyl; or $R^{21}$ and $R^{22}$ taken together form an optionally substituted non-aromatic heterocyclic ring;

A is selected from a direct bond, optionally substituted $C_{1-5}$alkylene, carbonyl or —C(O)—$C(R^dR^d)$—, wherein $R^d$ is independently selected from a direct bond hydrogen and $C_{1-2}$alkyl;

B is $C_{1-6}$alkylene, $C_{3-6}$alkenylene, —$(C_{1-5}alkyl)_{aa}$-O—$(C_{1-5}alkyl)_{bb}$-, —$(C_{1-5}alkyl)_{aa}$-C(O)—$(C_{1-5}alkyl)_{bb}$-, —$(CH_2)_{s1}$—$C(O)N(R^9)$—, or the group

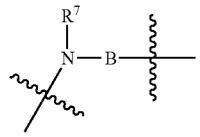

forms an optionally substituted saturated $C_{4-7}$heterocyclic ring, wherein aa and bb are independently 0 or 1 and wherein the combined length of $(C_{1-5}alkyl)_{aa}$, $(C_{1-5}alkyl)_{bb}$ is less than or equal to $C_5$alkyl and wherein $C_{1-6}$alkylene is optionally substituted by hydroxy.

E is —O—, —$S(O_n)$, —C(O)—, —$NR^{15}$— or —$C(R^9R^{10})_q$;

F is -$E(CH_2)_r$—;

G is selected from: hydrogen, halo, N, O, $S(O_n)$, C(O), $C(R^9R^{10})_r$, optionally substituted $C_{2-6}$alkenylene, optionally substituted $C_{2-6}$alkynylene or a direct bond to $R^{18}$, J is a group of the formula: —$(CH_2)_s$-L-$(CH_2)_s$— wherein when s is greater than 0, the alkylene group is optionally substituted, or the group

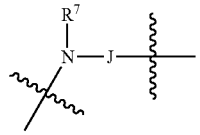

together forms an optionally substituted heterocyclic ring containing 4-7 carbons atoms;

K is selected from: a direct bond, —$(CH_2)_{s1}$—, —$(CH_2)_{s1}$—O—$(CH_2)_{s2}$—, —$(CH_2)_{s1}C(O)$—$(CH_2)_{s2}$—, —$(CH_2)_{s1}S(O_n)$—$(CH_2)_{s2}$—, —$(CH_2)_{s1}N(R^{18})$—$(CH_2)_{s2}$—, —$(CH_2)_{s1}$—$C(O)N(R^9)$—$(CH_2)_{s2}$—, —$(CH_2)_{s1}$—$N(R^9)C(O)$—$(CH_2)_{s2}$—, —$(CH_2)_{s1}$—$N(R^9)C(O)N(R^9)$—$(CH_2)_{s2}$—, —$(CH_2)_{s1}$—OC(O)—$(CH_2)_{s2}$—, —$(CH_2)_{s1}$—C(O)O—$(CH_2)_{s2}$—, —$(CH_2)_{s1}$—$N(R^9)C(O)O$—$(CH_2)_{s2}$—, —$(CH_2)_{s1}$—$OC(O)N(R^9)$—$(CH_2)_{s2}$—, —$(CH_2)_{s1}$—$OS(O_n)$—$(CH_2)_{s2}$—, or —$(CH_2)_{s1}$—$S(O_n)$—O—$(CH_2)_{s2}$—

$-(CH_2)_{s1}-S(O)_2N(R^9)-(CH_2)_{s2}-$, $-(CH_2)_{s1}-N(R^9)S(O)_2-(CH_2)_{s2}-$; wherein the $-(CH_2)_{s1}-$ and $-(CH_2)_{s2}-$ groups are independently optionally substituted by hydroxy or $C_{1-4}$alkyl;

L is selected from optionally substituted aryl or optionally substituted heterocyclyl;

M is $-(CH_2)-O-$;

n is an integer from 0 to 2;
p is an integer from 0 to 4;
q is an integer from 0 to 4;
r is an integer from 0 to 4;
s is an integer from 0 to 4;
s1 and s2 are independently selected from an integer from 0 to 4, and s1+s2 is less than or equal to 4;
t is an integer from 0 to 4;
aa and bb are independently 0 or 1;and
cc is an integer between 0 to 2;

with the proviso that
(i) when G is hydrogen or halo, then $R^{17}$ and $R^{18}$ are both absent;
(ii) when G is O, $S(O_n)$, C(O) or $C(R^{11}R^{12})_t$ then G is substituted by a single group independently selected from the definition of $R^{17}$ or $R^{18}$ and when G is a direct bond to $R^{18}$ then G is substituted by a single group selected from $R^{18}$;
(iii) when $R^3$ is a group of Formula (IIb), B is a group of Formula (IV), $R^8$ is selected from group (i) or (ii) above, $R^{11}$ is a group of the formula $N(R^{10}R^{11})$ and $R^1$, $R^2$ and $R^5$ are as defined above then $R^4$ cannot be hydrogen;
(iv) $R^3$ cannot be unsubstituted pyridyl or unsubstituted pyrimidinyl; and
(v) when $R^3$ is pyrazolyl substituted by phenyl or pyrazolyl substituted by phenyl and acetyl, $R^5$-M is hydroxyl or acetyloxy, $R^2$ is unsubstituted phenyl, then cannot be hydrogen or acetyl;
or a salt, or in-vivo hydrolyzable ester thereof.

7. The compound of claim 6, wherein $R^1$ is hydrogen.

8. The compound of claim 6, wherein $R^3$ is selected from a group of Formula (IIa) or Formula (IIb).

9. The compound of claim 8, wherein B is optionally substituted $C_{1-6}$alkylene.

10. The compound of claim 6, wherein $R^3$ is selected from a group of Formula (IIc) or Formula (IId).

11. The compound of claim 10 wherein the group

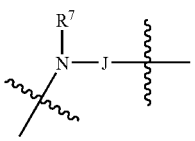

together forms an optionally substituted heterocyclic ring containing 4-7 carbons atoms.

12. The compound according to claim 11 wherein K is selected from:
$-(CH_2)_s-$, $-(CH_2)_s-O-(CH_2)_s-$, $-(CH_2)_s-C(O)-(CH_2)_s-$, $-(CH_2)_s-N(R^{18})-(CH_2)_s-$, $-(CH_2)_s-C(O)N(R^{18})-(CH_2)_s-$, $-(CH_2)_s-N(R^{18})C(O)-(CH_2)_s-$, $-(CH_2)_s-S(O)_2N(R^{18})-(CH_2)_s-$, or $-(CH_2)_s-NHS(O)_2-(CH_2)_s-$.

13. The compound of claim 8 wherein $R^8$ is selected from:
(i) hydrogen, $C_{1-6}$alkyl, $C_{2-6}$alkenyl, halo$C_{1-6}$alkyl, hydroxy, cyano, $C_{1-6}$alkylS($O_n$)—, $-O-R^b$, $C_{1-4}$alkoxy$C_{1-4}$alkyl, $-C(O)-R^b$, $C(O)O-R^b$, $-NH-C(O)-R^b$, N,N-di-$C_{1-4}$alkylamino, $-S(O_n)NR^bR^c$ where $R^b$ and $R^c$ are independently selected from hydrogen and $C_{1-6}$alkyl, and n is 0, 1 or 2;

(ii) -(Q)-aryl, optionally substituted by up to 3 groups selected from $R^{12}$, $R^{13}$ and $R^{14}$;
(iii) $C_{4-7}$heterocyclyl, optionally substituted by up to 3 groups selected from $R^{12}$, $R^{13}$ and $R^{14}$, or
(iv) $C_{3-7}$carbocyclyl, optionally substituted by up to 3 groups selected from $R^{12}$, $R^{13}$ and $R^{14}$.

14. The compound of claim 6 wherein $R^5$ is a group of Formula (III) wherein the group of Formula (III) is selected from any one of III-a to III-l;

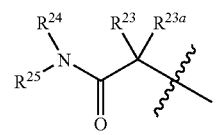

III-a

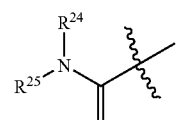

III-b

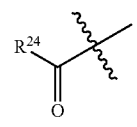

III-c

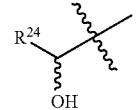

III-d

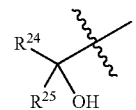

III-e

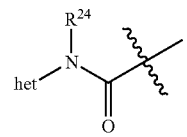

III-f

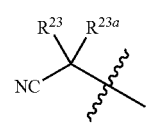

III-g

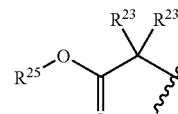

III-h

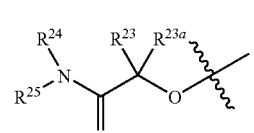

III-i

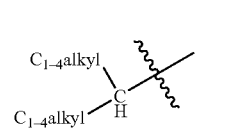

III-j

-continued

III-k

[Structure III-k: R$^{25}$—O—CH$_2$—C(R$^{23}$)(R$^{23a}$)—]

III-l

[Structure III-l: R$^{25}$—N(R$^{24}$)—CH$_2$—C(R$^{23}$)(R$^{23a}$)—O—]

wherein:
het represents an optionally substituted 3- to 8- membered heterocyclic ring containing from 1 to 4 heteroatoms independently selected from O, N and S;
R$^{23}$ and R$^{23a}$ are independently selected from hydrogen, fluoro or optionally substituted C$_{1-8}$alkyl; or R$^{23}$ and R$^{23a}$ together with the carbon to which they are attached form an optionally substituted 3 to 7-membered cycloalkyl ring
R$_{24}$ is selected from hydrogen, optionally substituted C$_{1-8}$alkyl, optionally substituted aryl, —R$^d$—Ar, where R$^d$ represents C$_{1-8}$alkylene and Ar represents optionally substituted aryl, and optionally substituted 3- to 8-membered heterocyclic ring optionally containing from 1 to 3 further heteroatoms independently selected from O, N and S;
R$_{25}$ is selected from hydrogen; optionally substituted C$_{1-8}$alkyl and optionally substituted aryl;
or where the group of Formula (III) represents a group of Formula III-a, III-b or III-i, then the group NR$^{24}$(—R$^{25}$) represents an optionally substituted 3- to 8- membered heterocyclic ring optionally containing from 1 to 3 further heteroatoms independently selected from O, N and S;
or where the group of Formula (III) represents structure III-e, R$^{24}$ and R$^{25}$ together with the carbon to which they are attached represents an optionally substituted 3- to 8-membered heterocyclic ring optionally containing from 1 to 4 heteroatoms independently selected from O, N and S.

15. The compound of claim 6 wherein the optional substituents on R$^2$ are selected from cyano, NR$^e$R$^f$, optionally substituted C$_{1-8}$alkyl, optionally substituted C$_{1-8}$alkoxy or halo wherein R$^e$ and R$^f$ are independently selected from hydrogen, C$_{1-6}$alkyl or aryl.

16. The compound of claim 4 selected from:
2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylethyl]-(2S)-propylamine;
2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-pyrid-4-ylbutyl]-(2S)-propylamine;
2-[3-(2,2-dimethyl-3-oxo-3-{azabicyclo[2.2.1]heptan-7-yl}propoxy)-5-(3,5-dimethylphenyl)-1H-pyrazol-4-yl]-N-[4-(4-methoxyphenyl)butyl]-(2S)-propylamine;
2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(43-trifluoromethylphenyl)ethyl]-(2S)-propylamine;
2-[3-(2,2-dimethyl-3-oxo-3-{azabicyclo[2.2.1]heptan-7-yl}propoxy)-5-(3,5-dimethylphenyl)-1H-pyrazol-4-yl]-N-[2-(4-fluorophenyl)ethyl]-(2S)-propylamine;
2-[3-(2,2-dimethyl-3-oxo-3-{azabicyclo[2.2.1]heptan-7-yl}propoxy)-5-(3,5-dimethyiphenyl)-1H-pyrazol-4-yl]-N-[2-(3-methoxyphenyl)ethyl]-(2S)-propylamine;
2-[3-(2,2-dimethyl-3-oxo-3-{azabicyclo[2.2.1]heptan-7-yl}propoxy)-5-(3,5-dimethyiphenyl)-1H-pyrazol-4-yl]-N-[2-(4-methoxyphenyl)ethyl]-(2S)-propylamine;
2-[3-(2,2-dimethyl-3-oxo-3-{azabicyclo[2.2.1]heptan-7-yl}propoxy)-5-(3,5-dimethyiphenyl)-1H-pyrazol-4-yl]-N-[2-(4-methylsulphonylaminophenyl)ethyl]-(2S)-propylamine; and
2-[3-(2,2-dimethyl-3-oxo-3-{azabicyclo[2.2.2]oct-2-yl}propoxy)-5-(3,5-dimethyiphenyl)-1H-pyrazol-4-yl]-N-[2-(1,3-benzodioxol-5-yl)ethyl]-(2S)-propylamine;
or a salt, or in-vivo hydrolyzable ester thereof.

17. A pharmaceutical formulation comprising a compound, or salt, or in-vivo hydrolyzable ester thereof, according to claim 4 and a pharmaceutically acceptable diluent or carrier.

* * * * *